US010081612B2

(12) United States Patent
Sokolovskii et al.

(10) Patent No.: US 10,081,612 B2
(45) Date of Patent: *Sep. 25, 2018

(54) PROCESS FOR PRODUCTION OF HEXANETRIOL FROM 5-HYDROXYMETHYLFURFURAL

(71) Applicant: Rennovia Inc., Santa Clara, CA (US)

(72) Inventors: Valery Sokolovskii, Santa Clara, CA (US); Mayya Lavrenko, Campbell, CA (US); Alfred Hagemeyer, Sunnyvale, CA (US); Eric L. Dias, Belmont, CA (US); James A. W. Shoemaker, Gilroy, CA (US); Vincent J. Murphy, San Jose, CA (US)

(73) Assignee: ARCHER-DANIELS-MIDLAND COMPANY, Decatur, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/417,110

(22) Filed: Jan. 26, 2017

(65) Prior Publication Data

US 2017/0298036 A1 Oct. 19, 2017

Related U.S. Application Data

(63) Continuation of application No. 14/957,551, filed on Dec. 2, 2015, now Pat. No. 9,586,920.

(60) Provisional application No. 62/086,651, filed on Dec. 2, 2014.

(51) Int. Cl.
| | |
|---|---|
| C07D 307/28 | (2006.01) |
| C07D 307/12 | (2006.01) |
| C07C 29/60 | (2006.01) |
| C07D 307/42 | (2006.01) |
| C07C 29/17 | (2006.01) |
| C07C 29/132 | (2006.01) |
| C07C 29/10 | (2006.01) |
| C07C 29/09 | (2006.01) |
| B01J 8/04 | (2006.01) |

(52) U.S. Cl.
CPC .............. *C07D 307/28* (2013.01); *B01J 8/04* (2013.01); *C07C 29/09* (2013.01); *C07C 29/103* (2013.01); *C07C 29/132* (2013.01); *C07C 29/172* (2013.01); *C07C 29/60* (2013.01); *C07D 307/12* (2013.01); *C07D 307/42* (2013.01); *B01J 2208/027* (2013.01)

(58) Field of Classification Search
CPC .................................................. C07D 307/28
USPC ........................................................ 549/502
See application file for complete search history.

(56) References Cited

U.S. PATENT DOCUMENTS

| | | | |
|---|---|---|---|
| 2,082,025 | A | 6/1937 | Peters, Jr. |
| 2,750,394 | A | 6/1956 | Peniston |
| 2,754,330 | A | 7/1956 | Schreyer |
| 2,917,520 | A | 12/1959 | Cope |
| 2,929,823 | A | 3/1960 | Garber et al. |
| 3,040,062 | A | 6/1962 | Hales |
| 3,070,633 | A | 12/1962 | Utne et al. |
| 3,083,236 | A | 3/1963 | Utne et al. |
| 3,118,912 | A | 1/1964 | Smith |
| 3,215,742 | A | 11/1965 | Horlenko |
| 3,268,588 | A | 8/1966 | Horlenko |
| 3,270,059 | A | 8/1966 | Winderl |
| 3,985,814 | A | 10/1976 | Dougherty |
| 4,064,172 | A | 12/1977 | Dewdney et al. |
| 4,339,387 | A | 7/1982 | Fléeche et al. |
| 4,400,468 | A | 8/1983 | Faber |
| 4,533,743 | A | 8/1985 | Medeiros et al. |
| 4,590,283 | A | 5/1986 | Gaset et al. |
| 4,740,605 | A | 4/1988 | Rapp |
| 4,912,237 | A | 3/1990 | Zeitsch |
| 4,971,657 | A | 11/1990 | Avignon et al. |
| 5,151,543 | A | 9/1992 | Ziemecki |
| 5,969,194 | A | 10/1999 | Hara et al. |
| 6,331,651 | B1 | 12/2001 | Ostermaier |
| 6,426,438 | B1 | 7/2002 | Fischer et al. |
| 6,518,440 | B2 | 2/2003 | Lightner |
| 6,706,932 | B1 | 3/2004 | Konishi et al. |
| 6,743,928 | B1 | 6/2004 | Zeitsch |
| 7,449,609 | B2 | 11/2008 | Haunert et al. |
| 7,579,490 | B2 | 8/2009 | Sanborn et al. |
| 7,994,347 | B2 | 8/2011 | Lilga et al. |
| 8,367,851 | B2 | 2/2013 | Lilga et al. |
| 8,742,144 | B2 | 6/2014 | Lilga et al. |
| 8,846,984 | B2 | 9/2014 | Allgeier et al. |
| 8,846,985 | B2 | 9/2014 | Allgeier et al. |
| 8,853,458 | B2 | 10/2014 | Dias et al. |
| 8,859,826 | B2 | 10/2014 | Allgeier et al. |

(Continued)

FOREIGN PATENT DOCUMENTS

| | | |
|---|---|---|
| CA | 2097812 A1 | 6/1992 |
| CN | 104209120 A | 12/2014 |

(Continued)

OTHER PUBLICATIONS

Besson et al., "Conversion of Biomass into Chemicals over Metal Catalysts", Chem. Rev., vol. 114, No. 3. 2014, pp. 1827-1870.

Buntara et al., "Caprolactam from Renewable Resources: Catalytic Conversion of 5-Hydroxymethylfurfural into Caprolactone", Angewandte Chemie Intertional Edition, vol. 50, 2011, pp. 7083-7087.

(Continued)

Primary Examiner — Taofiq A Solola
(74) Attorney, Agent, or Firm — Morrison & Foerster LLP

(57) ABSTRACT

Industrial scale conversions of 5-hydroxymethylfurfural to commodity chemicals such as 1,2,6-hexanetriol and 1,6-hexanediol by chemocatalytic conversions using hydrogen and a heterogeneous reduction catalyst are provided. The reactions are suitable for use in continuous flow reactors. Methods of carrying out the conversions are provided, as are product and catalyst compositions.

46 Claims, 13 Drawing Sheets

(56) References Cited

U.S. PATENT DOCUMENTS

| | | | |
|---|---|---|---|
| 8,884,036 | B2 | 11/2014 | De Silva et al. |
| 8,889,912 | B2 | 11/2014 | Allgeier et al. |
| 8,889,922 | B2 | 11/2014 | Allgeier et al. |
| 8,962,894 | B2 | 2/2015 | Allgeier et al. |
| 9,018,423 | B2 | 4/2015 | Allgeier et al. |
| 9,035,109 | B2 | 5/2015 | Dias et al. |
| 9,181,157 | B2 | 11/2015 | Allgeier et al. |
| 9,518,005 | B2 | 12/2016 | Dias et al. |
| 9,783,473 | B2 | 10/2017 | Dias et al. |
| 2003/0144552 | A1 | 7/2003 | Boschat et al. |
| 2006/0014988 | A1 | 1/2006 | Fischer et al. |
| 2006/0128844 | A1 | 6/2006 | Sanborn et al. |
| 2007/0112225 | A1 | 5/2007 | Sirch et al. |
| 2007/0287845 | A1 | 12/2007 | Lilga et al. |
| 2007/0288449 | A1 | 12/2007 | Datta et al. |
| 2008/0207958 | A1 | 8/2008 | Haunert et al. |
| 2009/0177018 | A1 | 7/2009 | Suzuki et al. |
| 2010/0317069 | A1 | 12/2010 | Burk et al. |
| 2011/0201848 | A1 | 8/2011 | Ii et al. |
| 2013/0172578 | A1 | 7/2013 | Allgeier et al. |
| 2013/0172580 | A1 | 7/2013 | Ritter et al. |
| 2013/0172629 | A1 | 7/2013 | Allgeier et al. |
| 2013/0184495 | A1 | 7/2013 | Dias et al. |
| 2013/0231505 | A1 | 9/2013 | Allgeier et al. |
| 2013/0289311 | A1 | 10/2013 | Allgeier et al. |
| 2013/0289312 | A1 | 10/2013 | Allgeier et al. |
| 2013/0289318 | A1 | 10/2013 | Allgeier et al. |
| 2013/0289319 | A1 | 10/2013 | Allgeier et al. |
| 2013/0331606 | A1 | 12/2013 | Dias et al. |
| 2014/0051872 | A1 | 2/2014 | Blank et al. |
| 2014/0275638 | A1 | 9/2014 | Huber et al. |
| 2014/0309461 | A1 | 10/2014 | Yoshida et al. |
| 2014/0343323 | A1 | 11/2014 | Dias et al. |
| 2015/0099903 | A1 | 4/2015 | Allgeier et al. |
| 2016/0023975 | A1 | 1/2016 | Allgeier et al. |
| 2016/0068469 | A1 | 3/2016 | Dias et al. |
| 2016/0068470 | A1 | 3/2016 | Dias et al. |

FOREIGN PATENT DOCUMENTS

| | | |
|---|---|---|
| EP | 2390247 A1 | 11/2011 |
| FR | 2663933 A1 | 1/1992 |
| FR | 2664273 A1 | 1/1992 |
| FR | 2669635 A1 | 5/1992 |
| GB | 591858 | 9/1947 |
| GB | 600871 | 4/1948 |
| GB | 876463 | 9/1961 |
| JP | 2008-143798 A | 6/2008 |
| JP | 2009-46417 A | 3/2009 |
| WO | 93/16034 A1 | 8/1993 |
| WO | 96/18603 A1 | 6/1996 |
| WO | 2007/146836 A1 | 12/2007 |
| WO | 2011/149339 A1 | 12/2011 |
| WO | 2013/101968 A1 | 7/2013 |
| WO | 2013/101969 A1 | 7/2013 |
| WO | 2013/101970 A1 | 7/2013 |
| WO | 2013/101977 A1 | 7/2013 |
| WO | 2013/109477 A1 | 7/2013 |
| WO | 2013/163540 A1 | 10/2013 |
| WO | 2013/163547 A1 | 10/2013 |
| WO | 2013/163556 A1 | 10/2013 |
| WO | 2013/163561 A1 | 10/2013 |
| WO | 2014/004867 A1 | 1/2014 |
| WO | 2014/152366 A1 | 9/2014 |
| WO | 2015/168327 A1 | 11/2015 |
| WO | 2017/075391 A1 | 5/2017 |
| WO | 2017/075425 A1 | 5/2017 |

OTHER PUBLICATIONS

Buntara et al., "Catalyst Studies on the Ring Opening of Tetrahydrofuran-Dimethanol to 1, 2, 6-Hexanetriol", Catalysis Today, vol. 210, 2013, pp. 106-116.

Buntara et al., "From 5-Hydroxymethylfurfural (HMF) to Polymer Precursors: Catalyst Screening Studies on the Conversion of 1,2,6-Hexanetriol to 1,6-Hexanediol", Top Catal, vol. 55, 2012, pp. 612-619.

Chatterjee et al., "Selective Hydrogenation of 5-Hydroxymethylfurfural to 2, 5-bis-(Hydroxymethyl)Furan using Pt/MCM-41 in an Aqueous Medium: A Simple Approach", Green Chem., vol. 16. 2014, pp. 4734-4739.

Chen et al., "Chemoselective Hydrogenolysis of Tetrahydropyran-2-Methanol to 1,6-Hexanediol over Rhenium-Modified Carbon-Supported Rhodium Catalysts", ChemCatChem, vol. 2, No. 5, 2010, pp. 547-555.

Chia et al., "Selective Hydrogenolysis of Polyols and Cyclic Ethers over Bifunctional Surface Sites on Rhodium-Rhenium Catalysts", Journal of the American Chemical Society, vol. 133, 2011, pp. 12675-12689.

Connolly et al., "Efficient Synthesis of 8-Oxa-3-aza-Bicyclo[3.2.1] Octane Hydrochloride", Organic Process Research & Development, vol. 14, 2010, pp. 459-465.

International Preliminary Report on Patentability received for PCT Patent Application No. PCT/US2015/063544, dated Jun. 15, 2017, 11 pages.

International Search Report and Written Opinion received for PCT Patent Application No. PCT/US2013/021315, dated Apr. 12, 2013, 15 pages.

International Search Report and Written Opinion received for PCT Patent Application No. PCT/US2015/063544, dated Sep. 29, 2016, 16 pages.

Invitation to Pay Additional Fee received for PCT Patent Application No. PCT/US2015/063544, mailed on Apr. 1, 2016, 6 pages.

Koso et al., "Chemoselective Hydrogenolysis of Tetrahydrofurfuryl Alcohol to 1,5-Pentanediol", Chemical. Communication, 2009, pp. 2035-2037.

Koso et al., "Promoting Effect of Mo on the Hydrogenolysis of Tetrahydrofurfuryl Alcohol to 1, 5-Pentanediol over Rh/SiO2", Journal of Catalysis, vol. 267, 2009, pp. 89-92.

Nakagawa et al., "Catalytic Reduction of Biomass-Derived Furanic Compounds with Hydrogen", ACS Catalysis, vol. 3, 2013, pp. 2655-2668.

Nakagawa et al., "Total Hydrogenation of Furan Derivatives over Silica-Supported Ni-Pd Alloy Catalyst", Catalysis Communications, vol. 12, 2010, pp. 154-156.

Non-Final Office Action received for U.S. Appl. No. 14/957,551, dated Jul. 8, 2016, 16 pages.

Notice of Allowance received for U.S. Appl. No. 13/739,975, dated Feb. 19, 2014, 9 pages.

Notice of Allowance received for U.S. Appl. No. 13/739,975, dated May 30, 2014, 7 pages.

Notice of Allowance received for U.S. Appl. No. 14/957,551, dated Oct. 27, 2016, 5 pages.

Putten et al., "Hydroxymethylfurfural, A Versatile Platform Chemical Made from Renewable Resources", Chemical Reviews, vol. 113, No. 3. 2013, pp. 1499-1597.

Schiavo et al., "Hydrogénation Catalytique du 5-Hydroxymethylfurfural en Milieu Aqueux", Bull Soc Chim Fr, vol. 128, 1991, pp. 704-711.

Schiavo et al., "Catalytic Hydrogenation 5-Hydroxymethylfurfural in Aqueous Medium", Bull Soc Chim Fr, vol. 128, 1991, pp. 704-711, (Translation).

Schiavo et al., "Hydrogenation Catalytique en Mileu Aquaux du 5-Hydroxymethylfural el des Sucres Precurseurs = Catalytic Hydrogenation in Aqueous Medium 5-Hydroxymethylfurfural and Precursor Sugars", 1991, 1 page.

PROCESS FOR PRODUCTION OF HEXANETRIOL FROM 5-HYDROXYMETHYLFURFURAL

CROSS-REFERENCE TO RELATED APPLICATIONS

This application is a continuation application of U.S. patent application Ser. No. 14/957,551, filed Dec. 2, 2015, now U.S. Pat. No. 9,586,920, which claims priority benefit to U.S. Provisional Patent Application Ser. No. 62/086,651, filed Dec. 2, 2014, the disclosure of each of which is herein incorporated by reference in its entirety.

STATEMENT OF RIGHTS TO INVENTIONS MADE UNDER FEDERALLY SPONSORED RESEARCH

Not applicable.

BACKGROUND OF THE INVENTION

Commodity chemicals are typically manufactured through the operation of continuous chemical conversion processes. Continuous conversion technology typically employs the use of continuous flow reactors, which offer certain advantages, such as the ability to prepare large volumes of chemicals (e.g., commodity chemicals) and lower capital and operational expenditures as compared to methods of production that do not employ continuous conversion technology. Continuous flow reactors can be used for a variety of transformations and can be operated in the gas or liquid phase.

5-Hydroxymethylfurfural ("HMF") is a platform chemical producible from biorenewable resources, particularly carbohydrate-containing feedstocks. The potential of HMF for the production of various compounds useful for fuel, fine chemical, and polymer applications, such as 5-alkoxymethylfurfural, 2,5-furandicarboxylic acid, 5-hydroxymethylfuroic acid, 2,5-bishydroxymethylfuran, 2,5-dimethylfuran, bis(5-methylfurfuryl)ether, levulinic acid, adipic acid, 1,6-hexanediol, caprolactone and caprolactam, has grown with the development of efficient processes for chemically converting HMF on a large-scale (van Putten et al. 2013 *Chem Rev* 113:1499-1597). However, the purity of HMF derived from a carbohydrate source limits the commercial viability of such processes. HMF is typically prepared from fructose in the presence of a mineral acid (de Vries et al. 2013 *Chem Rev* 113:1499-1597). This process produces side products such as humins, which are believed to be condensation products from the reaction constituents and can be oligomeric or polymeric in form. Accordingly, HMF feedstock can contain trace amounts of mineral acids and/or trace amounts of oligomeric or polymeric species which may affect the production of HMF conversion products, which are products produced directly or indirectly from the conversion of HMF.

The conversion of HMF to 2,5-bishydroxymethylfuran, 1,6-hexanediol, and other HMF conversion products via reduction using hydrogen and a heterogeneous catalyst has been reported. See, for example, Schiavo et al. 1991 *Bull Soc Chim Fr* 128:704-711; U.S. Pat. No. 7,994,347; U.S. Pat. No. 8,367,851; U.S. Pat. No. 8,742,144; U.S. Pat. No. 3,070,633; U.S. Pat. No. 3,083,236; U.S. Pat. No. 7,579,490; EP Patent No. 2390247; International Publication No. WO 2011/149339; Buntara et al. 2013 *Catal Today* 210:106-116; Buntara et al. 2011 *Angew Chem Int Ed* 50:7083-7087; International Publication No. WO 2013/163540; U.S. Pat. No. 3,040,062, Connolly et al. 2010 *Org Process Res Dev* 14:459-465, Nakagawa 2010 *Catal Commun* 12:154-156, International Publication Nos. WO 2014/152366 and WO 2013/109477, and Besson et al. 2014 *Chem Rev* 114:1827-1870. These processes are typically liquid-phase and, while many produce an HMF conversion product, there remain drawbacks that limit their use. First, batch mode conversions produce limited volumes of product, and commodity chemicals, which are needed in large volumes, cannot be produced as cost effectively using a batch mode. Second, reactions carried out using continuous conversion technology are similarly limited if the reactions employ any of: (i) low feedstock concentrations (if the feed concentration is too low, too much energy and expense will be necessary to recover the target product from the liquid phase); (ii) catalysts that are unstable under the reaction conditions needed for industrial application (such as catalysts that are not stable under many continuous hours on-stream in a continuous flow reactor); or (iii) catalysts that do not have the requisite selectively to produce a sufficient volume of the target HMF conversion product (high selectivity to the desired reaction product is desirable as it minimizes the costs associated with the purification of the product as fewer side products need to be removed). The limitations of current methods demonstrate the need for alternative methods of converting HMF to target HMF conversion products, such as commodity and specialty chemicals, on a commercial scale.

BRIEF SUMMARY OF THE INVENTION

The present invention addresses one or more of the limitations of current processes for producing conversion products from HMF. Significantly, the present disclosure provides processes for producing conversion products from HMF on a commercial/industrial scale.

The present disclosure describes continuous conversion processes in which HMF is a feedstock in a liquid phase continuous flow reactor and the transformation of at least a portion of HMF to a conversion product is carried out in a manner which is conducive to producing the conversion product on a commercial scale (for example, at least 5 kTa). The transformations detailed herein may occur in one or more steps and produce one or more intermediate products in the overall transformation of HMF to the desired, or target, conversion product. In one aspect, the target conversion product is 1,2,6-hexanetriol (HTO). In one aspect, the target conversion product is 1,6-hexanediol (HDO). In one variation, HTO is produced from HMF via transformation of HMF to the intermediate 2,5-bis-hydroxymethylfuran (BHMF) and the transformation of BHMF to HTO. In another variation, HTO is produced from HMF via transformation of HMF to the intermediate BHMF, the transformation of BHMF to the intermediate 2,5-bis-hydroxymethyltetrahydrofuran ("BHMTHF") and the transformation of BHMTHF to HTO. For any transformation in which HTO is a target conversion product obtained from HMF feedstock, the HTO obtained may be further transformed to HDO. For any transformation in which an intermediate is employed in the conversion of the HMF feedstock to a target conversion product, at least a portion of the intermediate in one variation may be isolated, e.g., if the intermediate is itself a target product. It is also understood that the transformations detailed herein may occur as a series of sequential transformations with HMF as the feedstock (e.g., HMF conversion to BHMF, which BHMF may be converted directly to HTO or indirectly to HTO via conversion to BHMTHF which is then converted to HTO, which HTO may be converted to HDO), or that any single transformation (e.g., BHMF to HTO) may occur in isolation, or that a series of transformations may occur starting with a feedstock other than HMF (e.g., BHMF as a feedstock in the conversion to HTO either directly or via conversion to BHMTHF, which BHMTHF may be converted to HTO, which HTO may be converted to HDO).

In one variation, the conversion of HMF to a target conversion product is carried out in a continuous flow reactor in a manner that is conducive to production of the target conversion product on an industrial scale, wherein at least one of conditions (1)-(4) apply: (1) the HMF feedstock concentration is at or greater than about 5, 10, 12 or 15 weight percent; (2) the transformation of HMF employs the use of at least one heterogeneous reduction catalyst that is stable over the desired on-stream period (e.g., at least one heterogeneous reduction catalyst is employed that is stable over an on-stream period of at least 150, 300, 500, 1,000, 2,000, 3,000, 4,000, 5,000, 6,000, 7,000, 8,000, 9,000, 10,000 hours or more); (3) the transformation of HMF employs the use of at least one heterogeneous reduction catalyst that is selective for the desired transformation (e.g., at least one heterogeneous reduction catalyst is employed that is at least 85%, 90%, 95%, or 99% selective for the desired transformation); and (4) the transformation of HMF employs the use of at least one heterogeneous reduction catalyst that yields the desired transformation in an acceptable amount for commercial production (e.g., at least one heterogeneous reduction catalyst is employed that provides the desired transformation product in at least 80%, 85%, 90%, 95%, or 99% yield). In some variations, at least two, three or all of conditions (1)-(4) apply. In one aspect, all of conditions (1)-(4) apply and conditions (2)-(4) apply to each transformation carried out in the continuous flow reactor, including, e.g., the transformation of HMF to BHMF, the transformation of BHMF to HTO either directly or via conversion to BHMTHF, which BHMTHF is transformed to HTO, and, where applicable, the transformation of BHMTHF to HTO and the transformation of HTO to HDO.

The present invention is directed to industrially scalable processes for catalytically converting HMF to HTO, HDO and other HMF conversion products. The processes feature high feedstock concentrations, conditions promoting long-term catalyst stability and productivity, and high conversion and selectivity to the target molecules.

In one aspect, the invention provides a process for preparing 2,5-bis-hydroxymethylfuran (BHMF) from 5-hydroxymethylfurfural (HMF). One embodiment comprises feeding 5-hydroxymethylfurfural (HMF) to a continuous flow reactor for an on-stream period of at least 150 hours; reacting the 5-hydroxymethylfurfural (HMF) with hydrogen in the continuous flow reactor in the presence of organic solvent and a heterogeneous reduction catalyst comprising at least one metal selected from the group consisting of Ni, Co, Cu, Ag, Pt, Pd, Fe and Ru or a combination thereof; and forming 2,5-bis-hydroxymethylfuran (BHMF) with at least about 90% selectivity and at least about 85% 5-hydroxymethylfurfural (HMF) conversion. In one variation, 2,5-bis-hydroxymethylfuran (BHMF) is formed with at least about 90% selectivity and at least about 90% 5-hydroxymethylfurfural (HMF) conversion. In another variation, 2,5-bis-hydroxymethylfuran (BHMF) is formed with at least about 90% selectivity and at least about 95% 5-hydroxymethylfurfural (HMF) conversion. In another variation, 2,5-bis-hydroxymethylfuran (BHMF) is formed with at least about 95% selectivity and at least about 90% 5-hydroxymethylfurfural (HMF) conversion. In another variation, 2,5-bis-hydroxymethylfuran (BHMF) is formed with at least about 95% selectivity and at least about 95% 5-hydroxymethylfurfural (HMF) conversion. In another variation, 2,5-bis-hydroxymethylfuran (BHMF) is formed over an on-stream period of at least 150 hours. Another variation comprises feeding 5-hydroxymethylfurfural (HMF) to a continuous flow reactor for an on-stream period of between about 150 hours and 10,000 hours or between about 500 hours and 10,000 hours or between about 1,000 hours and 10,000 hours or between about 5,000 hours and 10,000 hours. In another variation, 2,5-bis-hydroxymethylfuran (BHMF) is formed over an on-stream period of between about 150 hours and 10,000 hours or between about 500 hours and 10,000 hours or between about 1,000 hours and 10,000 hours or between about 5,000 hours and 10,000 hours. In another variation, the organic solvent contains less than about 25 weight % water. In another variation, the organic solvent contains less than about 10 weight % water. In another variation, the organic solvent contains less than about 5 weight % water. In still another variation, the organic solvent is substantially free of water. In another variation, the organic solvent contains water. In another variation, an organic solvent contains up to about 50 weight % water. In another variation an organic solvent contains up to about 25 weight % water or up to about 10 weight % water. In one variation, the 5-hydroxymethylfurfural (HMF) is fed to the continuous flow reactor through a guard bed comprising a transition metal. In another variation, the guard bed comprises at least one transition metal selected from the group consisting of Ag, Zn, Cu, Fe, Ni, Co and Pb or a salt or combination thereof. In another variation, the concentration of 5-hydroxymethylfurfural (HMF) is about or greater than about 5 weight percent in organic solvent. In such a variation, the concentration of HMF in the HMF feedstock is about or greater than about 5 weight percent. In another variation, the concentration of 5-hydroxymethylfurfural (HMF) is between about 5 weight percent and 25 weight percent in organic solvent. In still another variation, the concentration of 5-hydroxymethylfurfural (HMF) is about or greater than about 10 weight percent in organic solvent. In another variation, the concentration of 5-hydroxymethylfurfural (HMF) is between about 10 weight percent and 25 weight percent in organic solvent. Another embodiment comprises feeding 5-hydroxymethylfurfural (HMF) through a guard bed comprising a transition metal to a continuous flow reactor; reacting the 5-hydroxymethylfurfural (HMF) with hydrogen in the continuous flow reactor in the presence of organic solvent and a heterogeneous reduction catalyst comprising at least one metal selected from the group consisting of Ni, Co, Cu, Ag, Pt, Pd, Fe and Ru or a combination thereof; and forming 2,5-bis-hydroxymethylfuran (BHMF). In one variation, the guard bed comprises at least one transition metal selected from the group consisting of Ag, Zn, Cu, Fe, Ni, Co and Pb or a salt or combination thereof. In a further variation, the guard bed comprises at least one transition metal selected from the group consisting of Ag, Zn, Cu and Pb or a salt or combination thereof. In another variation, the concentration of 5-hydroxymethylfurfural (HMF) is greater than about 5 weight percent in organic solvent. In such an embodiment, the HMF feedstock fed to the continuous flow reactor comprises HMF in greater than about 5 weight percent in organic solvent, such as about any of 6, 10, 12 and 15 weight percent HMF in organic solvent or between about 5 to about 25 or between about 10 to about 25 weight percent HMF in organic solvent. In another variation, the concentration of 5-hydroxymethylfurfural (HMF) is between about 5 weight percent and 25 weight percent in organic solvent. In another variation, the concentration of 5-hydroxymethylfurfural (HMF) is about or greater than about 10 weight percent in organic solvent. In another variation, the concentration of 5-hydroxymethylfurfural (HMF) is between about 10 weight percent and 25 weight percent in organic solvent. In another variation, the concentration of 5-hydroxymethylfurfural (HMF) is about or greater than about 12 weight percent in organic solvent. In another variation, the concentration of 5-hydroxymethylfurfural (HMF) is between about 12 weight percent and 20 weight percent in organic solvent. In another variation, the 5-hydroxymethylfurfural (HMF) is fed to the continuous flow reactor for an on-stream period of at least 150 hours. In another variation, the 5-hydroxymethylfurfural (HMF) is fed to the continuous flow reactor for an on-stream period of at least any one of 300, 500, 1,000, 3,000, 6,000, 8,000 hours or more. In another variation, the 2,5-bis-hydroxymethylfuran (BHMF) is formed over an on-stream period of at least any one of 300, 500, 1,000, 3,000, 6,000, 8,000 hours or more. Another variation comprises feeding 5-hydroxymethylfurfural (HMF) to a continuous flow reactor for an on-stream period of between about 150 hours and 10,000 hours or between about 500 hours and 10,000 hours or between about 1,000 hours and 10,000 hours or between about 5,000 hours and 10,000 hours. In another variation, 2,5-bis-hydroxymethylfuran (BHMF) is formed over an on-stream period of between about 150 hours and 10,000 hours or between about 500 hours and 10,000 hours or between about 1,000 hours and 10,000 hours or between about 5,000 hours and 10,000 hours. In another variation, the 2,5-bis-hydroxymethylfuran (BHMF) is formed with at least about 90% selectivity and at least 85% 5-hydroxymethylfurfural (HMF) conversion. In another variation, the 2,5-bis-hydroxymethylfuran (BHMF) is formed with at least about 90% selectivity and at least 90% 5-hydroxymethylfurfural (HMF) conversion. In another variation, the 2,5-bis-hydroxymethylfuran (BHMF) is formed with at least about 90% selectivity and at least 95% 5-hydroxymethylfurfural (HMF) conversion. In another variation, the 2,5-bis-hydroxymethylfuran (BHMF) is formed with at least about 95% selectivity and at least 85% 5-hydroxymethylfurfural (HMF) conversion. In another variation, the 2,5-bis-hydroxymethylfuran (BHMF) is formed with at least about 95% selectivity and at least 90% 5-hydroxymethylfurfural (HMF) conversion. In another variation, the 2,5-bis-hydroxymethylfuran (BHMF) is formed with at least about 95% selectivity and at least 95% 5-hydroxymethylfurfural (HMF) conversion.

Another embodiment comprises feeding 5-hydroxymethylfurfural (HMF) to a continuous flow reactor at a concentration of greater than 6 weight percent in organic solvent for an on-stream period of at least 150 hours; reacting the 5-hydroxymethylfurfural (HMF) with hydrogen in the continuous flow reactor in the presence of the organic solvent and a heterogeneous reduction catalyst comprising at least one metal selected from the group consisting of Ni, Co, Cu, Ag, Pt, Pd, Fe and Ru or a combination thereof; and forming 2,5-bis-hydroxymethylfuran (BHMF) over the on-stream period of at least 150 hours. In one variation, the concentration of 5-hydroxymethylfurfural (HMF) is about or greater than about 10 weight percent in organic solvent. In another variation, the concentration of 5-hydroxymethylfurfural (HMF) is between about 10 weight percent and 25 weight percent in organic solvent. In one variation, a concentration of 5-hydroxymethylfurfural (HMF) is about or greater than about 12 weight percent. In another variation, the concentration of 5-hydroxymethylfurfural (HMF) is between about 12 weight percent and 20 weight percent in organic solvent. In another variation, the 5-hydroxymethylfurfural (HMF) is fed to the continuous flow reactor for an on-stream period of at least any one of 300, 500, 1,000, 3,000, 6,000, 8,000 hours or more. In another variation, the 2,5-bis-hydroxymethylfuran (BHMF) is formed over an on-stream period of at least any one of 300, 500, 1,000, 3,000, 6,000, 8,000 hours or more. Another variation comprises feeding 5-hydroxymethylfurfural (HMF) to a continuous flow reactor for an on-stream period of between about 150 hours and 10,000 hours or between about 500 hours and 10,000 hours or between about 1,000 hours and 10,000 hours or between about 5,000 hours and 10,000 hours. In another variation, 2,5-bis-hydroxymethylfuran (BHMF) is formed over an on-stream period of between about 150 hours and 10,000 hours or between about 500 hours and 10,000 hours or between about 1,000 hours and 10,000 hours or between about 5,000 hours and 10,000 hours. In another variation, the 5-hydroxymethylfurfural (HMF) is fed to the continuous flow reactor through a guard bed, which may in one variation comprise a transition metal. In another variation, the guard bed comprises at least one transition metal selected from the group consisting of Ag, Zn, Cu, Fe, Ni, Co and Pb or a salt or combination thereof. In still another variation, the 2,5-bis-hydroxymethylfuran (BHMF) is formed with at least about 90% selectivity and at least 85% 5-hydroxymethylfurfural (HMF) conversion. In still another variation, the 2,5-bis-hydroxymethylfuran (BHMF) is formed with at least about 90% selectivity and at least 90% 5-hydroxymethylfurfural (HMF) conversion. In another variation, the 2,5-bis-hydroxymethylfuran (BHMF) is formed with at least about 95% selectivity and at least 85% 5-hydroxymethylfurfural (HMF) conversion. In another variation, the 2,5-bis-hydroxymethylfuran (BHMF) is formed with at least about 95% selectivity and at least 90% 5-hydroxymethylfurfural (HMF) conversion. In another variation, the 2,5-bis-hydroxymethylfuran (BHMF) is formed with at least about 95% selectivity and at least 95% 5-hydroxymethylfurfural (HMF) conversion. In another variation, the organic solvent is selected from the group consisting of alcohols, esters, ethers and mixtures thereof. In another variation, the organic solvent contains water. In another variation, the organic solvent is an alcohol. In a further variation, the alcohol is selected from the group consisting of ethanol, n-propanol, isopropanol, n-butanol, t-butanol, iso-butanol and sec-butanol. In another variation, the organic solvent is an ester. In a further variation, the ester is selected from the group consisting of ethyl acetate, propyl acetate and butyl acetate. In another variation, the organic solvent is an ether. In a further variation, the ether is selected from the group consisting of dioxane, dioxolane, glyme, diglyme, triglyme and tetraglyme.

In one variation, the heterogeneous reduction catalyst contains two metals selected from the group consisting of Ni, Co, Cu, Ag, Pt, Pd, Fe and Ru. In one variation, the heterogeneous reduction catalyst comprises a combination of metals selected from the group consisting of Pt—Au, Co—Cu, Ni—Cu, Ag—Ni, Ag—Co and Ag—Ru. In another variation, the heterogeneous reduction catalyst further comprises a modifier. In a further variation, the modifier is selected from the group consisting of Au, W, Cu, Zn, Mo, Sb, Bi and Pb. In one variation, the heterogeneous reduction catalyst comprises two metals selected from the group consisting of Ni, Co, Cu, Ag, Pt, Pd, Fe and Ru and a modifier selected from the group consisting of Au, W, Cu, Zn, Mo, Sb, Bi and Pb, such as a heterogeneous reduction catalyst comprising Co—Cu(Zn). In another variation, the heterogeneous reduction catalyst comprises three metals selected from the group consisting of Ni, Co, Cu, Ag, Pt, Pd, Fe and Ru, such as a heterogeneous reduction catalyst selected from the group consisting of Ni—Co—Cu, Ag—Co—Cu, and Ni—Co—Ag. In another variation, the heterogeneous reduction catalyst comprises three metals selected from the group consisting of Ni, Co, Cu, Ag, Pt, Pd, Fe, Sc, Ti, V, Mn, Zn and Ru. In another variation, the heterogeneous reduction catalyst further comprises a catalyst support. In one variation, the catalyst support is selected from the group consisting of carbons, aluminas, zirconias, silicas, alumina-silicas, titanias, alumina-titanias, silicon carbides and mixed phases thereof. In yet another variation, the 5-hydroxymethylfurfural (HMF) is reacted with hydrogen at a temperature in a range of about 50° C. to about 150° C. and at a pressure in a range of about 50 psi to about 2000 psi.

A further embodiment comprises feeding 5-hydroxymethylfurfural (HMF) through a guard bed comprising a transition metal to a continuous flow reactor at a concentration of greater than about 5 weight percent in organic solvent for an on-stream period of at least 150 hours; reacting the 5-hydroxymethylfurfural (HMF) with hydrogen in the continuous flow reactor in the presence of the organic solvent and a heterogeneous reduction catalyst comprising at least one metal selected from the group consisting of Ni, Co, Cu, Ag, Pt, Fe and Ru or a combination thereof; and forming 2,5-bis-hydroxymethylfuran (BHMF) with at least about 90% selectivity and at least 85% 5-hydroxymethylfurfural (HMF) conversion over the on-stream period of at least 150 hours.

In another aspect, the invention provides a process for preparing 2,5-bis-hydroxymethyltetrahydrofuran (BHMTHF) from 2,5-bis-hydroxymethylfuran (BHMF) comprising reacting 2,5-bis-hydroxymethylfuran (BHMF), which may be obtained from any one of the above processes or other processes detailed throughout, with hydrogen in a continuous flow reactor in the presence of an organic solvent and a heterogeneous reduction catalyst comprising at least one metal selected from the group consisting of Ni, Co, Cu, Ag, Pt, Pd and Ru or a combination thereof; and forming 2,5-bis-hydroxymethyltetrahydrofuran (BHMTHF). In one variation, the heterogeneous reduction catalyst used in the reaction of 2,5-bis-hydroxymethylfuran (BHMF) with hydrogen is the same as or different from the heterogeneous reduction catalyst used in the reaction of 5-hydroxymethylfurfural (HMF) with hydrogen. In another variation, the temperature and pressure in the reaction of 2,5-bis-hydroxymethylfuran (BHMF) with hydrogen are the same as or different from the temperature and pressure in the reaction of 5-hydroxymethylfurfural (HMF) with hydrogen. In still another variation, the reactor used in the reaction of 2,5-bis-hydroxymethylfuran (BHMF) with hydrogen is the same as or different from the reactor used in the reaction of 5-hydroxymethylfurfural (HMF) with hydrogen.

In another aspect, the invention provides a process for preparing 1,2,6-hexanetriol (HTO) from 2,5-bis-hydroxymethyltetrahydrofuran (BHMTHF) comprising reacting 2,5-bis-hydroxymethyltetrahydrofuran (BHMTHF), which may be obtained from the above process for preparing 2,5-bis-hydroxymethyltetrahydrofuran (BHMTHF) from 2,5-bis-hydroxymethylfuran (BHMF) or any other processes detailed throughout, with hydrogen in a continuous flow reactor in the presence of an aqueous or organic solvent and a heterogeneous reduction catalyst comprising Pt; and forming 1,2,6-hexanetriol (HTO). In some variations, the solvent is an aqueous solvent. In some variations, the solvent is an organic solvent. In some variations the solvent is 100% water. In some variations, the solvent is a mixture of water and organic solvent. In some variations, the solvent is substantially free of water. In one variation, the heterogeneous reduction catalyst further comprises a modifier selected from the group consisting of Mo, La, Sm, Y, W and Re. In another variation, the heterogeneous reduction catalyst further comprises a catalyst support. In one variation, the catalyst support is selected from the group consisting of acidic ion-exchange resin, aluminas (including gamma alumina, fluorinated alumina, silica promoted alumina), zirconias (including sulfate or tungstate promoted zirconia), silicas, alumina-silicas (including silica promoted alumina), titanias, alumina-titanias, aluminum phosphate, tungsten oxide supported on silica alumina, acidic clay, supported mineral acid and zeolites. In one variation, the heterogeneous reduction catalyst used in the reaction of 2,5-bis-hydroxymethyltetrahydrofuran (BHMTHF) with hydrogen is the same as or different from (i) the heterogeneous reduction catalyst used in the reaction of 5-hydroxymethylfurfural (HMF) with hydrogen or (ii) the heterogeneous reduction catalyst used in the reaction of 2,5-bis-hydroxymethylfuran (BHMF) with hydrogen. In another variation, the temperature and pressure in the reaction of 2,5-bis-hydroxymethyltetrahydrofuran (BHMTHF) with hydrogen are the same as or different from (i) the temperature and pressure in the reaction of 5-hydroxymethylfurfural (HMF) with hydrogen or (ii) the temperature and pressure in the reaction of 2,5-bis-hydroxymethylfuran (BHMF) with hydrogen. In yet another variation, the reactor used in the reaction of 2,5-bis-hydroxymethyltetrahydrofuran (BHMTHF) with hydrogen is the same as or different from (i) the reactor used in the reaction of 5-hydroxymethylfurfural (HMF) with hydrogen or (ii) the reactor used in the reaction of 2,5-bis-hydroxymethylfuran (BHMF) with hydrogen.

In another aspect, the invention provides a process for preparing 1,2,6-hexanetriol (HTO) from 2,5-bis-hydroxymethylfuran (BHMF) comprising reacting 2,5-bis-hydroxymethylfuran (BHMF), which may be obtained from any one of the above processes or any other processes detailed throughout, with hydrogen in a continuous flow reactor in the presence of an aqueous or organic solvent and a heterogeneous reduction catalyst comprising at least one metal selected from the group consisting of Ni, Co, Cu, Ag, Pt, Pd and Ru or a salt or combination thereof; and forming 1,2,6-hexanetriol (HTO). In some variations, the solvent is an aqueous solvent. In some variations, the solvent is an organic solvent. In some variations the solvent is 100% water. In some variations, the solvent is a mixture of water and organic solvent. In some variations, the solvent is substantially free of water. In one variation, the 2,5-bis-hydroxymethylfuran (BHMF) is reacted with hydrogen at a temperature in a range of about 80° C. to about 180° C. and a pressure in a range of about 50 psi to about 2000 psi. In one variation, the heterogeneous reduction catalyst used in the reaction of 2,5-bis-hydroxymethylfuran (BHMF) with hydrogen is the same as or different from the heterogeneous reduction catalyst used in the reaction of 5-hydroxymethylfurfural (HMF) with hydrogen.

In another aspect, the invention provides a process for preparing 1,6-hexanediol (HDO) from 1,2,6-hexanetriol (HTO) comprising reacting 1,2,6-hexanetriol (HTO) obtained from one of the above processes for preparing 1,2,6-hexanetriol (HTO) or any other processes detailed throughout with hydrogen in a continuous flow reactor in the presence of a heterogeneous reduction catalyst comprising Pt; and forming 1,6-hexanediol (HDO). In one variation, the 1,2,6-hexanetriol (HTO) is reacted with hydrogen in a continuous flow reactor in the presence of an aqueous or organic solvent or a mixture thereof. In some variations, the solvent is an aqueous solvent. In some variations, the solvent is an organic solvent. In some variations the solvent is 100% water. In some variations, the solvent is a mixture of water and organic solvent. In some variations, the solvent is substantially free of water. In a further variation, the organic solvent is selected from the group consisting of alcohols, esters, ethers and mixtures thereof. In another variation, the heterogeneous reduction catalyst further comprises a modifier selected from the group consisting of Mo, La, Sm, Y, W and Re. In another variation, the heterogeneous reduction catalyst further comprises a catalyst support. In one variation, the catalyst support is selected from the group consisting of acidic ion-exchange resin, aluminas (including gamma alumina, fluorinated alumina, silica promoted alumina), zirconias (including sulfate or tungstate promoted zirconia), silicas, alumina-silicas (including silica promoted alumina), titanias, alumina-titanias, aluminum phosphate, tungsten oxide supported on silica alumina, acidic clay, supported mineral acid and zeolites. In another variation, the 1,2,6-hexanetriol (HTO) is reacted with hydrogen at a temperature in a range of about 80° C. to about 200° C. and at a pressure in a range of about 200 psi to about 2000 psi.

In another aspect, the invention provides a process for preparing 1,2,6-hexanetriol (HTO) from 5-hydroxymethylfurfural (HMF). One embodiment comprises feeding 5-hydroxymethylfurfural (HMF) to a continuous flow reactor at a concentration of greater than about 5 weight percent in organic solvent; reacting the 5-hydroxymethylfurfural (HMF) with hydrogen in the continuous flow reactor in the presence of the organic solvent and a heterogeneous reduction catalyst comprising at least one metal selected from the group consisting of Ni, Co, Cu, Ag, Pt, Pd, Fe and Ru or a combination thereof; forming 2,5-bis-hydroxymethylfuran (BHMF) in a first reactor effluent stream or a first reactor zone effluent stream; reacting the 2,5-bis-hydroxymethylfuran (BHMF) with hydrogen, without isolation or purification of the 2,5-bis-hydroxymethylfuran (BHMF) from the first reactor effluent stream or the first reactor zone effluent stream, in the presence of a heterogeneous reduction catalyst; forming 2,5-bis-hydroxymethyltetrahydrofuran (BHMTHF) in a second reactor effluent stream or a second reactor zone effluent stream; reacting the 2,5-bis-hydroxymethyltetrahydrofuran (BHMTHF) with hydrogen, without isolation or purification of the 2,5-bis-hydroxymethyltetrahydrofuran (BHMTHF) from the second reactor effluent stream or the second reactor zone effluent stream, in the presence of a heterogeneous reduction catalyst; and forming 1,2,6-hexanetriol (HTO).

Another embodiment comprises feeding 5-hydroxymethylfurfural (HMF) to a continuous flow reactor at a concentration of greater than about 5 weight percent in an organic solvent; reacting the 5-hydroxymethylfurfural (HMF) with hydrogen in the continuous flow reactor in the presence of the organic solvent and a heterogeneous reduction catalyst comprising at least one metal selected from the group consisting of Ni, Co, Cu, Ag, Pt, Pd, Fe and Ru or a combination thereof; forming 2,5-bis-hydroxymethylfuran (BHMF) in a first reactor effluent stream or a first reactor zone effluent stream; reacting the 2,5-bis-hydroxymethylfuran (BHMF) with hydrogen, without isolation or purification of the 2,5-bis-hydroxymethylfuran (BHMF) from the first reactor effluent stream or the first reactor zone effluent stream, in the presence of a heterogeneous reduction catalyst; and forming 1,2,6-hexanetriol (HTO).

It is understood that the transformations described herein with respect to a reactor effluent stream may also be carried out in connection with a corresponding reactor zone effluent stream. Accordingly, such transformations may be carried out in a continuous conversion system comprising multiple continuous flow reactors, a single continuous flow reactor comprising multiple reaction zones, or in two or more continuous flow reactors where at least one of the continuous flow reactors comprises more than one reaction zone.

It is understood that, if applicable, aspects of one variation detailed herein (e.g., and without limitation, aspects such as feedstock concentration, on-stream period, temperature, pressure, solvent, catalyst composition, catalyst support, etc.) may apply to other variations detailed throughout the same as if each and every applicable aspect were specifically and individually listed for all embodiments and variations. An aspect of a first variation may be applicable to a second variation if the aspect recited for the first variation does not conflict with that recited for the second variation. For example, and without limitation, where a first variation describes particular reaction conditions (e.g., solvent, pressure, and temperature), but a second variation is silent with respect to the reaction conditions, it is understood that the reaction condition aspects of the first variation may apply to the second variation because the particular reaction conditions recited do not conflict with the details provided for the second variation.

In another aspect, the present disclosure provides a heterogeneous reduction catalyst useful for converting HMF to BHMF, BHMF to BHMTHF or BHMF to HTO as disclosed herein, comprising at least one metal selected from the group consisting of Ni, Co, Cu, Ag, Pt, Pd, Fe and Ru or a combination thereof and a support selected from the group consisting of carbons, aluminas, zirconias, silicas, alumina-silicas, titanias, alumina-titanias, silicon carbides and mixed phases thereof.

Reduction catalysts useful for the transformations detailed herein are also provided. The present disclosure also provides HTO and/or HDO produced by the process of any of the transformations detailed herein that produce HTO and/or HDO.

In another aspect, the invention provides a process for preparing 2,5-bis-hydroxymethylfuran (BHMF) from 5-hydroxymethylfurfural (HMF) comprising reacting the 5-hydroxymethylfurfural (HMF) with hydrogen in a continuous flow reactor in the presence of an organic solvent and a heterogeneous reduction catalyst comprising at least one metal selected from the group consisting of Ni, Co, Cu, Ag, Pt, Pd, Fe and Ru or a combination thereof to form the 2,5-bis-hydroxymethylfuran (BHMF), wherein the process further comprises one or more of (i)-(iii): (i) forming the 2,5-bis-hydroxymethylfuran (BHMF) over an on-stream period of at least 150 hours; (ii) feeding the 5-hydroxymethylfurfural (HMF) through a guard bed comprising a transition metal to the continuous flow reactor; and (iii) feeding the 5-hydroxymethylfurfural (HMF) to the continuous flow reactor for an on-stream period of at least 150 hours.

In one variation, the reaction proceeds with at least 85% conversion of the 5-hydroxymethylfurfural (HMF) (e.g., over an on-stream period of 150 hours). In another variation, the process comprises forming the 2,5-bis-hydroxymethylfuran (BHMF) with at least about 90% selectivity (e.g., over an on-stream period of 150 hours). In another variation, (i) applies (i.e., forming the 2,5-bis-hydroxymethylfuran (BHMF) over an on-stream period of at least 150 hours). In another variation, (ii) applies (i.e., feeding the 5-hydroxymethylfurfural (HMF) through a guard bed comprising a transition metal to the continuous flow reactor). In some such variations, the guard bed comprises at least one transition metal selected from the group consisting of Ag, Zn, Cu, Fe, Ni, Co and Pb or a salt or combination thereof. In another variation, the guard bed comprises at least one transition metal selected from the group consisting of Ag, Zn, Cu and Pb or a salt or combination thereof. In another variation, (iii) applies (i.e., feeding the 5-hydroxymethylfurfural (HMF) to the continuous flow reactor for an on-stream period of at least 150 hours).

In another variation, the process comprises feeding the 5-hydroxymethylfurfural (HMF) to the continuous flow reactor at a concentration of greater than about 5 weight percent in the organic solvent. In another variation, the process comprises feeding the 5-hydroxymethylfurfural (HMF) to the continuous flow reactor at a concentration of greater than about 6 weight percent in the organic solvent. In another variation, the process comprises feeding the 5-hydroxymethylfurfural (HMF) to the continuous flow reactor at a concentration of greater than about 10 weight percent in the organic solvent. In another variation, the process comprises forming the 2,5-bis-hydroxymethylfuran (BHMF) with at least about 90% selectivity and at least 90% 5-hydroxymethylfurfural (HMF) conversion (e.g., over an on-stream period of 150 hours). In another variation, the process comprises forming the 2,5-bis-hydroxymethylfuran (BHMF) with at least about 95% selectivity and at least 90% 5-hydroxymethylfurfural (HMF) conversion (e.g., over an on-stream period of 150 hours). In another variation, the process comprises feeding the 5-hydroxymethylfurfural (HMF) to the continuous flow reactor at a concentration of greater than about any of 5, 6, 10 and 12 weight percent in the organic solvent and forming the 2,5-bis-hydroxymethylfuran (BHMF) with at least about 90% or 95% selectivity and at least 90% 5-hydroxymethylfurfural (HMF) conversion (e.g., over an on-stream period of 150 hours).

In any variation in which an organic solvent is employed, the organic solvent may comprise less than about 25 weight % water. In another variation, the organic solvent comprises less than about 10 weight % water. In another variation, the organic solvent is substantially free of water. In another variation, the organic solvent is selected from the group consisting of alcohols, esters, ethers and mixtures thereof. In another variation, the organic solvent comprises an alcohol. In another variation, the alcohol is selected from the group consisting of ethanol, n-propanol, isopropanol, n-butanol, t-butanol, iso-butanol and sec-butanol. In another variation, the organic solvent comprises an ester. In another variation, the ester is selected from the group consisting of methyl acetate, ethyl acetate, propyl acetate and butyl acetate. In another variation, the organic solvent comprises an ether. In another variation, the ether is selected from the group consisting of dioxane, dioxolane, glyme, diglyme, triglyme and tetraglyme.

In another variation, the heterogeneous reduction catalyst used in the reduction of 5-hydroxymethylfurfural (HMF) comprises a combination of metals selected from the group consisting of Co—Cu, Ni—Cu, Ag—Ni, Ag—Co and Ag—Ru. In another variation, the heterogeneous reduction catalyst further comprises a modifier. In another variation, the modifier is selected from the group consisting of Mn, Co, Au, W, Cu, Zn, Mo, Sb, Bi and Pb. In another variation, the heterogeneous reduction catalyst further comprises a catalyst support. In another variation, the catalyst support is selected from the group consisting of carbons, aluminas, zirconias, silicas, alumina-silicas, titanias, alumina-titanias, silicon carbides and mixed phases thereof. In another variation, the 5-hydroxymethylfurfural (HMF) is reacted with hydrogen at a temperature in a range of about 50° C. to about 150° C. and at a pressure in a range of about 50 psi to about 2000 psi.

In another aspect, the invention provides a process for preparing 2,5-bis-hydroxymethyltetrahydrofuran (BHMTHF) from 2,5-bis-hydroxymethylfuran (BHMF) comprising reacting the 2,5-bis-hydroxymethylfuran (BHMF) with hydrogen in a continuous flow reactor in the presence of an organic solvent and a heterogeneous reduction catalyst comprising at least one metal selected from the group consisting of Ni, Co, Cu, Ag, Pd, Pt and Ru or a combination thereof to form 2,5-bis-hydroxymethyltetrahydrofuran (BHMTHF). In another variation, the organic solvent used in the reaction of the 2,5-bis-hydroxymethylfuran (BHMF) with hydrogen comprises less than about 25 weight % water. In one variation, the 2,5-bis-hydroxymethylfuran (BHMF) is obtained by reaction of 5-hydroxymethylfurfural (HMF) with hydrogen according to any of the processes described herein. In another variation, the heterogeneous reduction catalyst used in the reaction of the 2,5-bis-hydroxymethylfuran (BHMF) with hydrogen is the same as the heterogeneous reduction catalyst used in the reaction of the 5-hydroxymethylfurfural (HMF) with hydrogen. In another variation, the heterogeneous reduction catalyst used in the reaction of the 2,5-bis-hydroxymethylfuran (BHMF) with hydrogen is different from the heterogeneous reduction catalyst used in the reaction of the 5-hydroxymethylfurfural (HMF) with hydrogen. In another variation, the temperature and pressure in the reaction of the 2,5-bis-hydroxymethylfuran (BHMF) with hydrogen are the same as the temperature and pressure in the reaction of the 5-hydroxymethylfurfural (HMF) with hydrogen. In another variation, the temperature and pressure in the reaction of the 2,5-bis-hydroxymethylfuran (BHMF) with hydrogen are different from the temperature and pressure in the reaction of the 5-hydroxymethylfurfural (HMF) with hydrogen. In another variation, the continuous flow reactor used in the reaction of the 2,5-bis-hydroxymethylfuran (BHMF) with hydrogen is the same as the continuous flow reactor used in the reaction of the 5-hydroxymethylfurfural (HMF) with hydrogen. In another variation, the continuous flow reactor used in the reaction of the 2,5-bis-hydroxymethylfuran (BHMF) with hydrogen is different from the continuous flow reactor used in the reaction of the 5-hydroxymethylfurfural (HMF) with hydrogen.

In another aspect, the invention provides a process for preparing 1,2,6-hexanetriol (HTO) from 2,5-bis-hydroxymethyltetrahydrofuran (BHMTHF) comprising reacting the 2,5-bis-hydroxymethyltetrahydrofuran (BHMTHF) with hydrogen in a continuous flow reactor in the presence of an aqueous or organic solvent and a heterogeneous reduction catalyst comprising at least one metal selected from the group consisting of Ni, Co, Cu, Ag, Pt and Ru or a combination thereof to form 1,2,6-hexanetriol (HTO). In one variation, the 2,5-bis-hydroxymethyltetrahydrofuran (BHMTHF) is obtained by reaction of 2,5-bis-hydroxymethylfuran (BHMF) with hydrogen according to any of the processes described herein. In some variations, the solvent is an aqueous solvent. In some variations, the solvent is an organic solvent. In some variations the solvent is 100% water. In some variations, the solvent is a mixture of water and organic solvent. In some variations, the solvent is substantially free of water. In another variation, the heterogeneous reduction catalyst used in the reaction of the 2,5-bis-hydroxymethyltetrahydrofuran (BHMTHF) with hydrogen is the same as (i) the heterogeneous reduction catalyst used in the reaction of the 5-hydroxymethylfurfural (HMF) with hydrogen or (ii) the heterogeneous reduction catalyst used in the reaction of the 2,5-bis-hydroxymethylfuran (BHMF) with hydrogen. In another variation, the heterogeneous reduction catalyst used in the reaction of the 2,5-bis-hydroxymethyltetrahydrofuran (BHMTHF) with hydrogen is different from (i) the heterogeneous reduction catalyst used in the reaction of the 5-hydroxymethylfurfural (HMF) with hydrogen or (ii) the heterogeneous reduction catalyst used in the reaction of the 2,5-bis-hydroxymethylfuran (BHMF) with hydrogen. In another variation, the temperature and pressure in the reaction of the 2,5-bis-hydroxymethyltetrahydrofuran (BHMTHF) with hydrogen are the same as (i) the temperature and pressure in the reaction of the 5-hydroxymethylfurfural (HMF) with hydrogen or (ii) the temperature and pressure in the reaction of the 2,5-bis-hydroxymethylfuran (BHMF) with hydrogen. In another variation, the temperature and pressure in the reaction of the 2,5-bis-hydroxymethyltetrahydrofuran (BHMTHF) with hydrogen are different from (i) the temperature and pressure in the reaction of the 5-hydroxymethylfurfural (HMF) with hydrogen or (ii) the temperature and pressure in the reaction of the 2,5-bis-hydroxymethylfuran (BHMF) with hydrogen. In another variation, the continuous flow reactor used in the reaction of the 2,5-bis-hydroxymethyltetrahydrofuran (BHMTHF) with hydrogen is the same as (i) the continuous flow reactor used in the reaction of the 5-hydroxymethylfurfural (HMF) with hydrogen or (ii) the continuous flow reactor used in the reaction of the 2,5-bis-hydroxymethylfuran (BHMF) with hydrogen. In another variation, the continuous flow reactor used in the reaction of the 2,5-bis-hydroxymethyltetrahydrofuran (BHMTHF) with hydrogen is different from (i) the continuous flow reactor used in the reaction of the 5-hydroxymethylfurfural (HMF) with hydrogen or (ii) the continuous flow reactor used in the reaction of the 2,5-bis-hydroxymethylfuran (BHMF) with hydrogen. In another variation, the 2,5-bis-hydroxymethyltetrahydrofuran (BHMTHF) is reacted with hydrogen in the presence of an organic solvent comprising less than about 25 weight % water.

In another aspect, the invention provides a process for preparing 1,2,6-hexanetriol (HTO) from 2,5-bis-hydroxymethylfuran (BHMF) comprising reacting the 2,5-bis-hydroxymethylfuran (BHMF) with hydrogen in a continuous flow reactor at a pressure in a range of about 50 psi to about 2000 psi in the presence of an aqueous or organic solvent and a heterogeneous reduction catalyst comprising at least one metal selected from the group consisting of Ni, Co, Cu, Ag, Pt, Pd and Ru or a combination thereof to form 1,2,6-hexanetriol (HTO). In one variation, the 2,5-bis-hydroxymethylfuran (BHMF) is obtained by reaction of 5-hydroxymethylfurfural (HMF) with hydrogen according to any of the processes described herein. In some variations, the solvent is an aqueous solvent. In some variations, the solvent is an organic solvent. In some variations the solvent is 100% water. In some variations, the solvent is a mixture of water and organic solvent. In some variations, the solvent is substantially free of water. In another variation, the 2,5-bis-hydroxymethylfuran (BHMF) is reacted with hydrogen at a temperature in a range of about 80° C. to about 180° C. In another variation, the heterogeneous reduction catalyst used in the reaction of the 2,5-bis-hydroxymethylfuran (BHMF) with hydrogen is the same as the heterogeneous reduction catalyst used in the reaction of the 5-hydroxymethylfurfural (HMF) with hydrogen. In another variation, the heterogeneous reduction catalyst used in the reaction of the 2,5-bis-hydroxymethylfuran (BHMF) with hydrogen is different from the heterogeneous reduction catalyst used in the reaction of the 5-hydroxymethylfurfural (HMF) with hydrogen. In another variation, the 2,5-bis-hydroxymethylfuran (BHMF) is reacted with hydrogen in the presence of an organic solvent comprising less than about 25 weight % water.

In another aspect, the invention provides a process for preparing 1,6-hexanediol (HDO) from 1,2,6-hexanetriol (HTO) comprising reacting the 1,2,6-hexanetriol (HTO) with hydrogen in a continuous flow reactor in the presence of a heterogeneous reduction catalyst comprising at least one metal selected from the group consisting of Ni, Co, Cu, Ag, Pt and Ru or a combination thereof to form 1,6-hexanediol (HDO). In one variation, the 1,2,6-hexanetriol (HTO) is obtained by any of the processes described herein. In another variation, the 1,2,6-hexanetriol (HTO) is reacted with hydrogen in a continuous flow reactor in the presence of an aqueous or organic solvent or a mixture thereof. In some variations, the solvent is an aqueous solvent. In some variations, the solvent is an organic solvent. In some variations the solvent is 100% water. In some variations, the solvent is a mixture of water and organic solvent. In some variations, the solvent is substantially free of water. In another variation, the 1,2,6-hexanetriol (HTO) is reacted with hydrogen in a continuous flow reactor in the presence of an organic solvent comprising less than about 25 weight % water. In another variation, the organic solvent used in the reaction of the 1,2,6-hexanetriol (HTO) with hydrogen is selected from the group consisting of alcohols, esters, ethers and mixtures thereof. In another variation, the heterogeneous reduction catalyst used in the reaction of the 1,2,6-hexanetriol (HTO) with hydrogen further comprises a modifier. In another variation, the modifier used in the reaction of the 1,2,6-hexanetriol (HTO) with hydrogen is selected from the group consisting of Mn, Co, Au, W, Cu, Zn, Mo, Sb, Bi and Pb. In another variation, the heterogeneous reduction catalyst used in the reaction of the 1,2,6-hexanetriol (HTO) with hydrogen further comprises a catalyst support. In another variation, the catalyst support used in the reaction of the 1,2,6-hexanetriol (HTO) with hydrogen is selected from the group consisting of carbons, aluminas, zirconias, silicas, alumina-silicas, titanias, alumina-titanias, silicon carbides and mixed phases thereof. In another variation, the 1,2,6-hexanetriol (HTO) is reacted with hydrogen at a temperature in a range of about 80° C. to about 200° C. and at a pressure in a range of about 50 psi to about 2000 psi.

In another aspect, the invention provides a process for preparing 1,2,6-hexanetriol (HTO) from 5-hydroxymethylfurfural (HMF) comprising (a) feeding 5-hydroxymethylfurfural (HMF) to a continuous flow reactor at a concentration of greater than about 5 weight percent in a first organic solvent; (b) reacting the 5-hydroxymethylfurfural (HMF) with hydrogen in the continuous flow reactor in the presence of the first organic solvent and a first heterogeneous reduction catalyst comprising at least one metal selected from the group consisting of Ni, Co, Cu, Ag, Pt, Pd, Fe and Ru or a combination thereof to form 2,5-bis-hydroxymethylfuran (BHMF) in a first reactor effluent stream or a first reactor zone effluent stream; (c) reacting the 2,5-bis-hydroxymethylfuran (BHMF) with hydrogen, without isolation or purification of the 2,5-bis-hydroxymethylfuran (BHMF) from the first reactor effluent stream or the first reactor zone effluent stream, in the presence of a second heterogeneous reduction catalyst to form 2,5-bis-hydroxymethyltetrahydrofuran (BHMTHF) in a second reactor effluent stream or a second reactor zone effluent stream; and (d) reacting the 2,5-bis-hydroxymethyltetrahydrofuran (BHMTHF) with hydrogen, without isolation or purification of the 2,5-bis-hydroxymethyltetrahydrofuran (BHMTHF) from the second reactor effluent stream or the second reactor zone effluent stream, in the presence of a third heterogeneous reduction catalyst to form the 1,2,6-hexanetriol (HTO). In one variation, the first organic solvent comprises less than about 25 weight % water. In another variation, the 2,5-bis-hydroxymethylfuran (BHMF) is reacted with hydrogen in the presence of a second organic solvent comprising less than about 25 weight % water. In another variation, the 2,5-bis-hydroxymethyltetrahydrofuran (BHMTHF) is reacted with hydrogen in the presence of a third organic solvent comprising less than about 25 weight % water. In another variation, the 2,5-bis-hydroxymethyltetrahydrofuran (BHMTHF) is reacted with hydrogen in the presence of an aqueous solvent. In some variations the solvent is 100% water. In some variations, the solvent is a mixture of water and organic solvent.

In another aspect, the invention provides a process for preparing 1,2,6-hexanetriol (HTO) from 5-hydroxymethylfurfural (HMF) comprising feeding the 5-hydroxymethylfurfural (HMF) to a continuous flow reactor at a concentration of greater than about 5 weight percent in a first organic solvent; reacting the 5-hydroxymethylfurfural (HMF) with hydrogen in the continuous flow reactor in the presence of the first organic solvent and a first heterogeneous reduction catalyst comprising at least one metal selected from the group consisting of Ni, Co, Cu, Ag, Pt, Pd, Fe and Ru or a combination thereof to form 2,5-bis-hydroxymethylfuran (BHMF) in a first reactor effluent stream or a first reactor zone effluent stream; and reacting the 2,5-bis-hydroxymethylfuran (BHMF) with hydrogen, without isolation or purification of the 2,5-bis-hydroxymethylfuran (BHMF) from the first reactor effluent stream or the first reactor zone effluent stream, in the presence of a second heterogeneous reduction catalyst to form the 1,2,6-hexanetriol (HTO). In one variation, the organic solvent comprises less than about 25 weight % water. In another variation, the 2,5-bis-hydroxymethylfuran (BHMF) is reacted with hydrogen in the presence of a second organic solvent comprising less than about 25 weight % water. In another variation, the 2,5-bis-hydroxymethylfuran (BHMF) is reacted with hydrogen in the presence of an aqueous solvent. In some variations the solvent is 100% water. In some variations, the solvent is a mixture of water and organic solvent.

Another embodiment comprises converting the 1,6-hexanediol (HDO) produced by any of the processes provided herein to one or more of HMDA, adipic acid, caprolactam, caprolactone, a polyol, a polyester polyol, a polyester and a polyurethane. Another embodiment comprises comprising converting the 2,5-bis-hydroxymethylfuran (BHMF), the 2,5-bis-hydroxymethyltetrahydrofuran (BHMTHF) or the 1,2,6-hexanetriol (HTO) produced by any of the processes provided herein to any one or more of a polyol, a polyester polyol, a polyester and a polyurethane.

In one variation of any of the processes provided herein in which a catalyst support is present, the catalyst support is a shaped support. In another variation, the shape of the catalyst support is selected from the group consisting of an extrudate, sphere, bead, cylinder, pellet, tablet, multi-lobed shape, ring, star, ripped cylinder, trihole, alpha and wheels.

In one variation of any of the processes provided herein, at least one of the heterogeneous reduction catalysts comprises at least one metal selected from the group consisting of Ag, Ru, Pd and Pt, and the total concentration of the metals is from at least 0.1 weight % to about 15 weight % of the total weight of the catalyst. In another variation, at least one of the heterogeneous reduction catalysts comprises at least one metal selected from the group consisting of Ni, Cu, Co and Fe, and the total concentration of the metals is from at least 0.5 weight % to about 40 weight % of the total weight of the catalyst.

In another aspect, the invention provides a process for preparing 2,5-bis-hydroxymethyltetrahydrofuran (BHMTHF) from 2,5-bis-hydroxymethylfuran (BHMF) comprising reacting the 2,5-bis-hydroxymethylfuran (BHMF) with hydrogen in a continuous flow reactor at a pressure in a range of about 50 psi to about 2000 psi in the presence of (i) an organic solvent comprising less than about 25 weight % water, and (ii) a heterogeneous reduction catalyst comprising at least one metal selected from the group consisting of Ni, Co, Cu, Ag, Pd, Pt and Ru or a combination thereof to form the 2,5-bis-hydroxymethyltetrahydrofuran (BHMTHF).

In another aspect, the invention provides a process for preparing 1,2,6-hexanetriol (HTO) from 2,5-bis-hydroxymethyltetrahydrofuran (BHMTHF) comprising reacting the 2,5-bis-hydroxymethyltetrahydrofuran (BHMTHF) with hydrogen in a continuous flow reactor at a pressure in a range of about 50 psi to about 2000 psi in the presence of (i) an organic solvent comprising less than about 25 weight % water, and (ii) a heterogeneous reduction catalyst comprising at least one metal selected from the group consisting of Ni, Co, Cu, Ag, Pt and Ru or a combination thereof to form the 1,2,6-hexanetriol (HTO) with at least about 90% selectivity and at least 85% 2,5-bis-hydroxymethyltetrahydrofuran (BHMTHF) conversion.

In another aspect, the invention provides a process for preparing 1,2,6-hexanetriol (HTO) and 1,6-hexanediol (HDO) from 2,5-bis-hydroxymethyltetrahydrofuran (BHMTHF) comprising reacting the 2,5-bis-hydroxymethyltetrahydrofuran (BHMTHF) with hydrogen in a continuous flow reactor at a pressure in a range of about 50 psi to about 2000 psi in the presence of (i) an organic solvent comprising less than about 25 weight % water, and (ii) a heterogeneous reduction catalyst comprising at least one metal selected from the group consisting of Ni, Co, Cu, Ag, Pt and Ru or a combination thereof to form the 1,2,6-hexanetriol (HTO) and the 1,6-hexanediol (HDO) with at least about 90% combined selectivity and at least 85% 2,5-bis-hydroxymethyltetrahydrofuran (BHMTHF) conversion.

In another aspect, the invention provides a process for preparing 2,5-bis-hydroxymethylfuran (BHMF) from 5-hydroxymethylfurfural (HMF) comprising reacting the 5-hydroxymethylfurfural (HMF) with hydrogen in a continuous flow reactor at a pressure in a range of about 50 psi to about 2000 psi in the presence of (i) an organic solvent comprising less than about 25 weight % water, and (ii) a heterogeneous reduction catalyst comprising Cu to form the 2,5-bis-hydroxymethylfuran (BHMF) with at least about 90% selectivity and at least 85% 5-hydroxymethylfurfural (HMF) conversion. In one variation, the organic solvent comprises dioxane. In another variation, the organic solvent comprises isopropanol. In another variation, the organic solvent comprises glyme. In another variation, the organic solvent comprises from about 5 weight % to about 20 weight % water. In another variation, the heterogeneous reduction catalyst further comprises an alumina catalyst support.

In another aspect, the invention provides a process for preparing 1,2,6-hexanetriol (HTO) from 5-hydroxymethylfurfural (HMF) comprising (a) reacting the 5-hydroxymethylfurfural (HMF) with hydrogen in a continuous flow reactor in the presence of (i) a first organic solvent comprising less than about 25 weight % water, and (ii) a first heterogeneous reduction catalyst comprising Cu to form 2,5-bis-hydroxymethylfuran (BHMF); (b) reacting the 2,5-bis-hydroxymethylfuran (BHMF) with hydrogen in the presence of (i) a second organic solvent comprising less than about 25 weight % water, and (ii) a second heterogeneous reduction catalyst comprising Ni to form 2,5-bis-hydroxymethyltetrahydrofuran (BHMTHF); and (c) reacting the 2,5-bis-hydroxymethyltetrahydrofuran (BHMTHF) with hydrogen in the presence of i) a third organic solvent comprising less than about 25 weight % water, and (ii) a third heterogeneous reduction catalyst comprising Pt to form the 1,2,6-hexanetriol (HTO). In one variation, the 2,5-bis-hydroxymethylfuran (BHMF) is formed in a first reactor effluent stream and is reacted with hydrogen without isolation or purification of the 2,5-bis-hydroxymethylfuran (BHMF) from the first reactor effluent stream. In one variation, the 2,5-bis-hydroxymethylfuran (BHMF) is formed in a first reactor zone effluent stream and is reacted with hydrogen without isolation or purification of the 2,5-bis-hydroxymethylfuran (BHMF) from the first reactor zone effluent stream. In another variation, the 2,5-bis-hydroxymethyltetrahydrofuran (BHMTHF) is formed in a second reactor effluent stream and is reacted with hydrogen without isolation or purification of the 2,5-bis-hydroxymethyltetrahydrofuran (BHMTHF) from the second reactor effluent stream. In another variation, the 2,5-bis-hydroxymethyltetrahydrofuran (BHMTHF) is formed in a second reactor zone effluent stream and is reacted with hydrogen without isolation or purification of the 2,5-bis-hydroxymethyltetrahydrofuran (BHMTHF) from the second reactor zone effluent stream. In another variation, one or more of the first, second, and third organic solvents comprises dioxane. In another variation, each of the first, second, and third organic solvents comprises dioxane. In another variation, one or more of the first, second, and third organic solvents comprises isopropanol. In another variation, each of the first, second, and third organic solvents comprises isopropanol. In another variation, one or more of the first, second, and third organic solvents comprises glyme. In another variation, each of the first, second, and third organic solvents comprises glyme. In another variation, the third heterogeneous reduction catalyst further comprises tungsten.

In another aspect, the invention provides a process for preparing 1,6-hexanediol (HDO) from 5-hydroxymethylfurfural (HMF) comprising (a) reacting the 5-hydroxymethylfurfural (HMF) with hydrogen in a continuous flow reactor in the presence of (i) a first organic solvent comprising less than about 25 weight % water, and (ii) a first heterogeneous reduction catalyst comprising at least one metal selected from the group consisting of Co, Mn, Ni, and Cu or a combination thereof to form 2,5-bis-hydroxymethyltetrahydrofuran (BHMTHF); (b) reacting the 2,5-bis-hydroxymethyltetrahydrofuran (BHMTHF) with hydrogen in a continuous flow reactor the presence of (i) a second organic solvent comprising less than about 25 weight % water, and (ii) a second heterogeneous reduction catalyst comprising Pt to form the 1,6-hexanetriol (HDO). In one variation, the second heterogeneous reduction catalyst further comprises tungsten. In another variation, the reaction of step (a) occurs within a first reaction zone and the reaction of step (b) occurs within a second reaction zone, wherein the first and second reaction zones are contained within the same continuous flow reactor. In another variation, the reaction of step (a) occurs within a first continuous flow reactor, and the reaction of step (b) occurs within a second continuous flow reactor.

In another variation, the reaction of step (a) comprises formation of 2,5-bis-hydroxymethylfuran (BHMF), and at least a portion of the 2,5-bis-hydroxymethylfuran (BHMF) is reacted with hydrogen in the continuous flow reactor to form 2,5-bis-hydroxymethyltetrahydrofuran (BHMTHF). In another variation, the reaction of step (b) comprises formation of 1,2,6-hexanetriol (HTO), and at least a portion of the 1,2,6-hexanetriol (HTO) is reacted with hydrogen in the continuous flow reactor to form 1,6-hexanediol (HDO). In another variation, one or both of the first and second organic solvents comprises dioxane. In another variation, one or both of the first and second organic solvents comprises isopropanol. In another variation, one or both of the first and second organic solvents comprises glyme. In another variation, the temperature in the reaction of step (b) is higher than the temperature in the reaction of step (a). In another variation, the pressure in the reaction of step (b) is higher than the pressure in the reaction of step (a).

In another aspect, the invention provides a continuous conversion system for producing a reduction product, wherein the continuous conversion system comprises (i) a first contained area for the reduction of a first reactant in the presence of hydrogen and a heterogeneous reduction catalyst comprising Cu; (ii) a second contained area for the reduction of a second reactant in the presence of hydrogen and a heterogeneous reduction catalyst comprising Ni; and (iii) a third contained area for the reduction of a third reactant in the presence of hydrogen and a heterogeneous reduction catalyst comprising Pt; wherein the contained areas are sequentially coupled such that the second reactant comprises the product of the first reduction reaction and the third reactant comprises the product of the second reduction reaction. In one variation, the first and second contained areas are contained within a single continuous flow reactor. In another variation, the second and third contained areas are contained within a single continuous flow reactor. In another variation, the reduction product comprises 1,2,6-hexanetriol (HTO). In another variation, the first reactant comprises 5-hydroxymethylfurfural (HMF), the second reactant comprises 2,5-bis-hydroxymethylfuran (BHMF), and the third reactant comprises 2,5-bis-hydroxymethyltetrahydrofuran (BHMTHF). In another variation, the continuous conversion system further comprises a guard bed comprising a transition metal. In another variation, the guard bed is coupled to the first contained area such that the first reactant can be fed through the guard bed to the first contained area.

DETAILED DESCRIPTION OF THE INVENTION

Definitions

Figure 1:
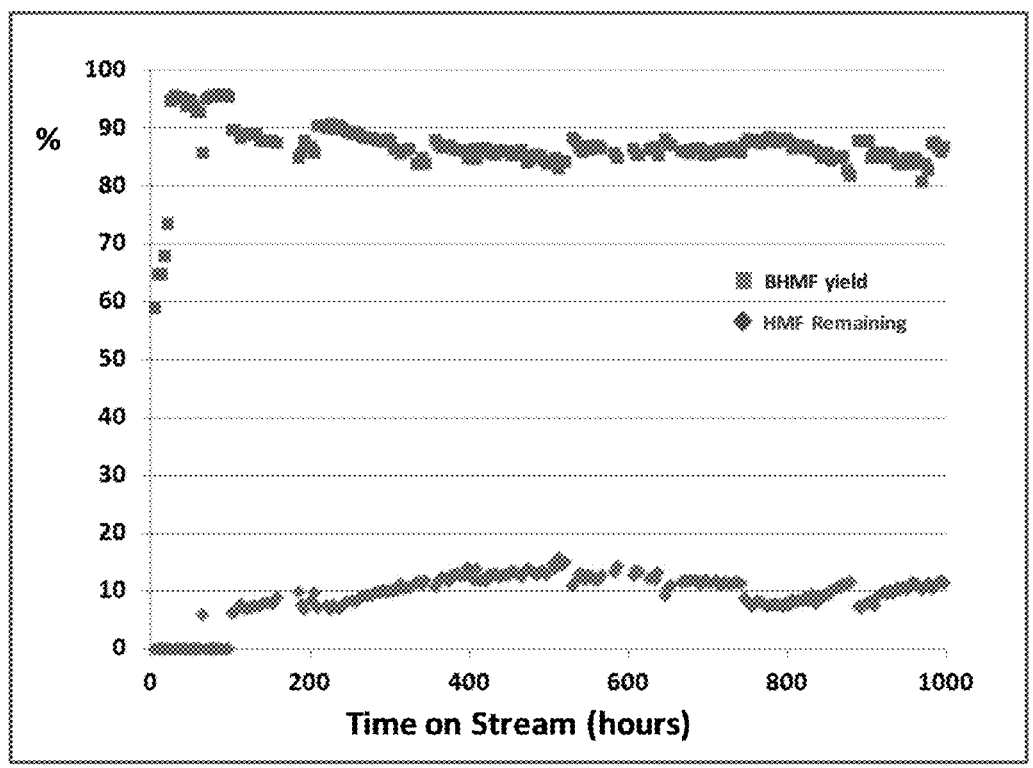
FIG. 1 depicts results (BHMF yield and HMF remaining as a function of time on-stream) for the conversion of HMF to BHMF in isopropanol in a fixed bed reactor using a Pt(Au) catalyst on an $Al_2O_3$ support, as described in Example 1.

"About" a parameter or value includes that parameter or value per se. For example, "about X" includes and describes X, per se.

As used herein, the abbreviation "HMF" refers to 5-hydroxymethylfurfural, which is also represented by formula 1 (Scheme 1).

As used herein, the abbreviation "BHMF" refers to 2,5-bis-hydroxymethylfuran, which is also represented by formula 2 (Scheme 1).

As used herein, the abbreviation "BHMTHF" refers to 2,5-bis-hydroxymethyltetrahydrofuran, which is also represented by formula 3 (Scheme 1).

As used herein, the abbreviation "HTO" refers to 1,2,6-hexanetriol, which is also represented by formula 4 (Scheme 1).

As used herein, the abbreviation "HDO" refers to 1,6-hexanediol, which is also represented by formula 5 (Scheme 1).

As used herein, the abbreviation "HMDA" refers to hexamethylenediamine.

As used herein, the term "time on-stream" or "on-stream period" refers to the time that a heterogeneous reduction catalyst is operative and productive, e.g., forming the target molecule.

As used herein, the term "substantially free of water" refers to a water content that is less than about 2 weight percent of the overall composition. For example, a composition that is substantially free of water is a composition wherein less than about 2 weight percent of the composition is water.

As used herein, the terms "modifier" and "promoter" refer to a substance (e.g., a metal and/or alloy) that improves the properties of a catalyst, such as activity, selectivity or stability. For example, a catalytic promoter or modifier may increase, enhance or accelerate the activity of a catalyst. A modifier or promoter may be combined with a catalyst.

As used herein, the terms "catalyst composition" and "catalyst formulation" refer to a composition or formulation comprising a catalyst metal, metal salt or metal combination, a catalyst support and optionally a modifier.

As used herein, the term "reactor effluent stream" refers to the stream exiting a chemical reactor (e.g., a continuous flow reactor such as a fixed bed reactor). A reactor effluent stream can be (1) analyzed to determine a reaction product(s), (2) processed to isolate a reaction product and/or recover a feed chemical (which can be recycled), and/or (3) used as feedstock for a subsequent reaction or downstream reactor. A reaction product can be isolated from a reactor effluent stream by one or more conventional methods known in the art including, for example, solvent extraction, crystallization or evaporative processes.

As used herein, the term "reactor zone effluent stream" refers to the stream exiting a zone of a chemical reactor containing more than one reaction zone (e.g., a continuous flow reactor such as a fixed bed reactor containing two or more reaction zones). A reactor contains more than one reaction zone if the reactor has discrete areas differently configured (such as a first area containing a first catalyst and a second area containing a second catalyst). A reactor zone effluent stream can be (1) analyzed to determine a reaction product(s), (2) processed to isolate a reaction product and/or recover a feed chemical (which can be recycled), and/or (3) used as feedstock for a subsequent reaction or downstream reactor zone. A reaction product can be isolated from a reactor zone effluent stream by one or more conventional methods known in the art including, for example, solvent extraction, crystallization or evaporative processes.

Selectivity and conversion parameters provided herein refer to average selectivity and conversion as measured over the time course of a particular transformation. For example, reference to a selectivity of at least "Y" for the conversion of reactant A to product B refers to the average selectivity over the time course of the reaction of A to B. It is therefore appreciated that, at select time points during the reaction of A to B, the value of Y may be lower than Y, provided that the average Y across the time course of the reaction is at least Y.

In some embodiments, the selectivity of a reaction described herein is at least about 90%, 95%, or 99% over an on-stream period of 150, 300, 500, 1,000, 3,000, 5,000, 8,000, or 10,000 hours. In some embodiments, the conversion of a reaction described herein is at least about 85%, 90,%, 95%, or 99% over an on-stream period of 150, 300, 500, 1,000, 3,000, 5,000, 8,000, or 10,000 hours. In one variation, the selectivity is at least about 90% over an on-stream period of 150 hours. In another variation, the conversion is at least about 85% over an on-stream period of 150 hours. In another variation, the selectivity is at least about 90% and the conversion is at least about 90% over an on-stream period of 300 hours.

Continuous Conversion Processes for Liquid Phase Production of HTO from HMF

Disclosed are chemical processes and catalyst formulations useful for the liquid phase production of 1,2,6-hexanetriol (HTO) from 5-hydroxymethylfurfural (HMF). HTO produced from the described process may be converted to 1,6-hexanediol (HDO). The processes produce the target molecules efficiently and selectively and are suitable for commercial scale production of 1,2,6-hexanetriol (HTO), 1,6-hexanediol (HDO) and related molecules.

The process technology includes several chemocatalytic conversions in the liquid phase, depicted in Scheme 1. HMF (1), readily derived from C-6 carbohydrates such as glucose and fructose, can be converted to BHMF (2), and BHMF (2) can be converted to BHMTHF (3) by sequential catalytic hydrogenation. BHMTHF (3) can be converted to HTO (4) by catalytic hydrogenolysis. Alternatively, BHMF (2) can be converted to HTO (4) directly by catalytic hydrogenation and hydrogenolysis. HTO (4) can be converted to HDO (5) by selective hydrogenolysis and the HDO produced can be converted to downstream products such as HMDA, adipic acid, caprolactam, caprolactone, polyols, polyester polyols, polyesters and polyurethanes, useful for the production of, for example, nylon, polyurethanes and epoxy resins. Furthermore, BHMF (2), BHMTHF (3) and HTO (4) produced from the conversions described herein can be converted to polyols, polyester polyols, polyesters and polyurethanes, useful for the production of, for example, nylons, polyurethanes and epoxy resins.

A significant challenge associated with the catalytic conversion of highly functionalized biorenewably-derived molecules and intermediates is catalyst stability. Long term catalyst stability is a necessity for commodity chemical production, meaning that the catalyst must be stable, productive, and selective under reaction conditions for long periods. The physical and chemical environment within a fixed bed reactor is a significant factor that influences the stability of the catalyst. The use of an aqueous solvent at high temperature is particularly challenging, especially with respect to the stability of the support and the propensity for metal leaching from the catalyst. For example, commonly deployed industrial catalyst supports such as aluminas, silicas and zeolites are typically not stable in pure aqueous environments at high temperature. The continuous fixed bed operations described herein were found to provide several advantages. For example, commonly deployed industrial catalyst supports can be used. Secondly, the use of an organic solvent with a heat of vaporization lower than water can enable more cost effective product isolations as less energy will be required to remove the solvent by industrial methods such as evaporative distillation. Thirdly, metal leaching from the catalyst support can be mitigated through the use of an organic solvent. In some instances, the presence of some water can be beneficial. The presence of water in combination with an organic solvent at the appropriate ratio, such as those described herein, can improve solubility, which can enable fixed bed operation at higher reactant or product concentrations. The presence of water may be beneficial to the process by enabling the solubility of reagents used in previous or subsequent process steps. Furthermore, for cost effective product isolation, an organic solvent-water combination at the appropriate ratio, such as those described herein, can be removed as an azeotropic mixture by industrial methods such as evaporative distillation.

The described conversions can be performed in one or more continuous flow reactors. Exemplary continuous flow reactors include fixed bed, continuous stirred tank (CSTR), bubble column and ebullated bed reactors. In one embodiment, the continuous flow reactor is a fixed bed reactor. The described conversions can be performed in different reaction zones within a continuous flow reactor. In some embodiments, each conversion is performed in a separate continuous flow reactor or within a separate reaction zone within one or more continuous flow reactors. In some embodiments, two or more conversions are performed within the same reaction zone within a continuous flow reactor.

Scheme 1

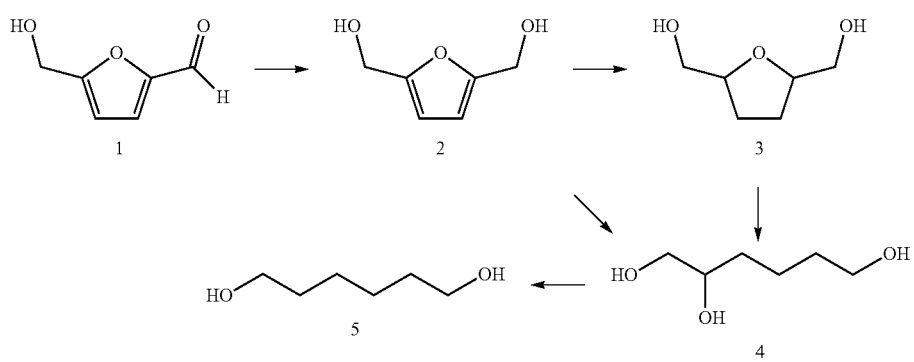

In a particular variation, at least one of the transformations depicted of Scheme 1 is performed in a continuous flow reactor with HMF as the feedstock fed to the continuous flow reactor, an organic solvent selected from the group consisting of an alcohol, ester and ether, and a heterogeneous reaction catalyst, wherein the concentration of HMF as the feedstock is about or greater than about 5 weight percent. In one variation, no more than 5 or 10 weight % water is present in the reactor effluent stream or the reactor zone effluent stream when HTO is produced. In one variation, the concentration of HMF as the feedstock is greater than or equal to 6, 10, 12 or 15 weight percent and wherein no more than 5 or 10 weight % water is present in the reactor effluent stream or the reactor zone effluent stream or wherein no more than 15, 20, or 25 weight % water is present in the reactor effluent stream or the reactor zone effluent stream. In one such variation, the transformations of HMF to BHMF to HTO are performed. In another such variation, the transformations of HMF to BHMF to BHMTHF to HTO are performed. The transformation may in one aspect be carried out by a heterogeneous reduction catalyst, which may be the same or different for the different transformations of Scheme 1, wherein the heterogeneous reduction catalyst performs the desired transformation (e.g., HMF to BHMF or BHMF to HTO, etc.) with at least about any one of 90%, 95% and 99% selectivity and at a conversion of least about any one of 85%, 90%, 95% and 99% for any of the individual steps in the transformation. In addition or alternatively, the transformations may in one aspect be carried out over an on-stream period of at least about any of 150, 300, 500, 1,000, 3,000, 5,000, 8,000, 10,000 or more hours. In one aspect, the product of the transformation is formed over an on-stream period of at least about any of 150, 300, 500, 1,000, 3,000, 5,000, 8,000, 10,000 or more hours. The transformations may in one aspect be carried out over an on-stream period of between about 150 hours and 10,000 hours or between about 500 hours and 10,000 hours or between about 1,000 hours and 10,000 hours or between about 5,000 hours and 10,000 hours. In another aspect, the product of the transformation is formed over an on-stream period of between about 150 hours and 10,000 hours or between about 500 hours and 10,000 hours or between about 1,000 hours and 10,000 hours or between about 5,000 hours and 10,000 hours. In a particular variation, at least one of the transformations of Scheme 1 (e.g., HMF to BHMF; or BHMF to BHMTHF; or BHMF to HTO; or BHMTHF to HTO; or HMF to BHMF to HTO; or HMF to BHMF to BHMTHF to HTO) is performed in a continuous flow reactor, wherein the reaction is characterized by one or more of features (1)-(6): (1) a solution of HMF wherein the concentration of HMF is any of about or greater than about 5, 6, 10, 12 or 15 weight percent of the solution is used as the feedstock in the continuous flow reactor; (2) use of an organic solvent selected from the group consisting of an alcohol, ester and ether, optionally comprising water; (3) use of a heterogeneous reaction catalyst that produces the product with at least about any one of 90%, 95% and 99% selectivity and at a conversion of at least about any one of 85%, 90%, 95% and 99% for any of the individual steps in the transformation; (4) no more than 5 or 10 weight % water is present in the reactor effluent stream or the reactor zone effluent stream; (5) the transformation is carried out over an on-stream period of at least about any of 150, 300, 500, 1,000, 3,000, 5,000, 8,000, 10,000 or more hours; and (6) HMF as the feedstock is fed through a guard bed comprising a transition metal to the continuous flow reactor.

It is understood that each of features (1)-(6) may be combined in any manner or combination, the same as if each and every combination of features were specifically and individually listed. In one variation, two of features (1)-(6) are present. For example, a reaction may be characterized by features (1) and (2), or (1) and (3), or (1) and (4), or (1) and (5), or (1) and (6), or (2) and (3), or (2) and (4), or (2) and (5), or (2) and (6), or (3) and (4), or (3) and (5), or (3) and (6), or (4) and (5), or (4) and (6), or (5) and (6). In another variation, three of features (1)-(6) are present. For example, a reaction may be characterized by features (1), (3) and (5) or (1), (3) and (6) or (1), (2) and (3), or (2), (3) and (4) or (2), (4) and (5). In another variation, four of features (1)-(6) are present. For example, a reaction may be characterized by features (1), (3), (5) and (6), or (1), (2), (3) and (6), or (1), (2), (3) and (4), or (1), (2), (4) and (6), or (2), (4), (5) and (6). In a further variation, five of features (1)-(6) are present. For example, a reaction may be characterized by features (1), (2), (3), (5) and (6), or (1), (2), (3), (4) and (6), or (1), (3), (4), (5) and (6), or (1), (2), (3), (4) and (5). In still another variation, all of features (1)-(6) are present.

Consecutive conversions (e.g., HMF to BHMF to BHMTHF) can be performed (1) using the same catalyst composition or different catalyst compositions, (2) using the same catalyst support or different catalyst supports, (3) in a single reactor or multiple (i.e., two or more) reactors in sequence, and/or (4) under the same process conditions (e.g., reaction temperature, hydrogen pressure, flow rate) or different process conditions. When performed in a single reactor, consecutive conversions may be performed in multiple (i.e., two or more) reactor zones.

Methods for determining the optimal flow rate are known in the art. In one embodiment, a flow rate is used that promotes good liquid and gas distribution to the surface of each catalyst particle across and down the reactor bed, for example, for a fixed bed reactor. The reactor is sized to the desired conversion, accordingly, wherein the width and/or length of the reactor are determined based on management of mass transfer rates and the heat of reaction.

The continuous flow reactors, organic solvents, feed concentrations and guard beds described above are useful for the processes disclosed herein. Additional features, solvents and/or conditions for each process are noted below.

Conversion of HMF (1) to BHMF (2)

The conversion of HMF (1) to BHMF (2) is, in one variation, performed using a concentration of HMF in the liquid phase that is sufficiently high for production on an industrial scale. In one embodiment, the feed concentration of HMF is at or greater than about 5 weight percent. In another embodiment, the feed concentration of HMF is at or greater than about 6 weight percent. In another embodiment, the feed concentration of HMF is at or greater than about 10 weight percent. In yet another embodiment, the feed concentration of HMF is at or greater than about 12 weight percent. In a further embodiment, the feed concentration of HMF is at or greater than about 15 weight percent. In one aspect, the feed concentration of HMF is at least a value provided herein, but less than 50 or 40 or 30 or 25 or 20 or 15 weight percent. In one variation, HMF is used as a feedstock in bulk. In another variation, HMF is provided as a feedstock in a solvent.

Trace impurities such as mineral acids and/or oligomeric or polymeric species may be present in HMF feedstock which can foul or poison the catalyst, thereby diminishing its lifetime and performance. A guard bed can be used to sequester potential impurities from the HMF feedstock prior to reaction with the catalyst. The use of a guard bed can enable long-term catalyst stability, especially for catalyst formulations that are sensitive to trace impurities (e.g., catalysts formulations containing Ni, Co, Cu or Ag). The composition of a guard bed may be selected based on the known impurities of the feedstock (e.g., HMF) and the heterogeneous catalyst composition. Catalyst formulations containing precious metals (e.g., Pt) may be less sensitive to trace impurities; however, a guard bed may still be helpful even for these catalysts when using feed concentrations greater than about 10 weight percent. The use of a guard bed has been shown to improve catalyst performance (see Example 2 and Comparative Example 3) and is thus a significant contribution to the industrial applicability of the described processes.

For the removal of trace impurities from mineral acids (e.g., chloride, sulfate, phosphate), typical guard beds consist of bases dispersed on inorganic supports (e.g., NaOH on alumina). Such guard beds are not suitable for liquid phase processes due to the solubility of the base in the liquid phase.

Metal-based guard beds are suitable for the removal of trace impurities from mineral acids in the processes of the invention. Exemplary metals include the transition metals Ag, Zn, Cu, Fe, Ni, Co and Pb and combinations thereof (e.g., Zn—Cu, Ag—Cu, Ag—Zn, Zn—Ag—Cu). In some embodiments, the metal is selected from Ag, Co, Ni, Cu and combinations thereof. Metals in their metallic states or metal salts may be used. Exemplary metal salts include ZnO, PbO and $PbCO_3$.

The metals or metal salts may be used with or without a support. Exemplary bulk (unsupported) guard beds include Raney copper or Raney copper modified with other metals. Exemplary guard bed supports include carbons, aluminas, zirconias, silicas, alumina-silicas and titanias or mixed phases therefrom. Exemplary supported metal-based guard beds include Cu on $ZrO_2$, $Al_2O_3$, $TiO_2$, $SiO_2$ or carbon and Ag on $ZrO_2$, $Al_2O_3$, $TiO_2$, $SiO_2$ or carbon or ZnO on $ZrO_2$, $Al_2O_3$, $TiO_2$, $SiO_2$.

For the removal of oligomeric or polymeric impurities, the guard bed may contain a polymer absorbent. Such absorbents may comprise porous absorbent materials such as activated carbons, silicas, aluminas, alumina-silicas, titanias, zirconias or mixed phases therefrom. In one embodiment, the guard bed comprises a metal or metal salt supported on a porous absorbent material. Exemplary metal-based guard beds containing a porous absorbent material are Cu on $ZrO_2$, $Al_2O_3$, $TiO_2$, $SiO_2$ or carbon and Ag on $ZrO_2$, $Al_2O_3$, $TiO_2$, $SiO_2$ or carbon or ZnO on $ZrO_2$, $Al_2O_3$, $TiO_2$, $SiO_2$. In some embodiments, an absorbent guard bed is used in combination with a metal-based guard bed. The guard bed supports may occur in a variety of shapes, for example, extruded shapes and pressed shapes, including but not limited to spheres, extrudates, pellets (cut extrudates), trilobes, quatralobes, rings and pentarings as described in the 2014 Saint-Gobain NorPro Catalytic Products brochure and website. Exemplary shapes include extrudates, spheres, beads, cylinders, pellets, tablets, multi-lobed shapes, rings, stars, ripped cylinders, triholes, alphas, wheels, and the like. Formulating the guard bed on a shaped support is useful to prevent excessive back pressure during the operation of fixed bed reactors on commercial scale.

In one embodiment, the guard bed is operated at a temperature range of about 20° C. to about 150° C. In another embodiment, the guard bed is operated at a temperature of about 20° C. to about 100° C.

In one embodiment, the guard bed is operated under a hydrogen pressure of about 15 psi to about 2000 psi. In another embodiment, the hydrogen pressure is about 50 psi to about 1000 psi. In another embodiment, the guard bed is operated at the same hydrogen pressure as the HMF conversion.

The guard bed may be formulated to be regenerated using thermal processing conditions when spent. In certain embodiments, a guard bed can be regenerated by calcining at elevated temperature. The thermal process used for regeneration can be conducted under various gaseous atmospheres, e.g., air, nitrogen, hydrogen, and forming gas. In one embodiment, the guard bed is regenerated by calcining at a temperature range of about 200° C. to about 800° C. In another embodiment, the guard bed is regenerated by calcining at a temperature of about 250° C. to about 600° C.

Organic solvents, such as alcohols, esters, ethers and mixtures thereof, optionally comprising water, are suitable for the conversion of HMF (1) to BHMF (2). Exemplary alcohols include ethanol, n-propanol, isopropanol, n-butanol, t-butanol, iso-butanol and sec-butanol. Exemplary esters include methyl acetate, ethyl acetate, propyl acetate and butyl acetate. Exemplary ethers include dioxane, dioxolane, glyme, diglyme, triglyme and tetraglyme. In one embodiment, the organic solvent contains less than about 25 weight % water. In another embodiment, the organic solvent contains less than about 10 weight % water. In another embodiment, the organic solvent contains less than about 5 weight % water. In another embodiment, the organic solvent is substantially free of water. In another embodiment, the organic solvent contains water. In one embodiment, an organic solvent contains up to about 50 weight % water. In another embodiment an organic solvent contains up to about 25 weight % water or up to about 10 weight % water. In another embodiment, the organic solvent contains between about 5 and 25 weight % water, between about 15 and 25 weight % water, or between about 10 and 20 weight % water. In one embodiment, the organic solvent is an azeotropic mixture comprising water. In one embodiment, the organic solvent is dioxane that contains between about 10 and 20 weight % water. In one embodiment, the organic solvent is isopropanol that contains between about 10 and 20 weight % water. In one embodiment, the organic solvent is glyme that contains between about 10 and 20 weight % water. The use of an organic solvent has been shown to improve catalyst performance (see Example 2 and Comparative Example 4).

The conversion of HMF (1) to BHMF (2) may be carried out under conditions in which less than 50 weight % water is present. In one embodiment, the conversion of HMF to BHMF is carried out under conditions in which less than 25 weight % water is present. In another embodiment, the conversion of HMF to BHMF is carried out under conditions in which less than 20 weight % water is present. In another embodiment, the conversion of HMF to BHMF is carried out under conditions in which less than 10 weight % water is present. In another embodiment, the conversion of HMF to BHMF is carried out under conditions in which less than 5 weight % water is present.

Suitable heterogeneous reduction catalysts for the conversion of HMF (1) to BHMF (2) are those that contain at least one metal selected from Ni, Co, Cu, Ag, Pt, Pd, Fe and Ru or a combination thereof. In one embodiment, the heterogeneous reduction catalyst contains at least one metal selected from Cu, Co, Ag, Ni and Pt. In another embodiment, the heterogeneous reduction catalyst contains a combination of two metals selected from the group consisting of Ni, Co, Cu, Ag, Pt, Pd, Fe and Ru. Exemplary metal combinations include Co—Cu, Ni—Cu, Ag—Ni, Pt—Au, Ag—Co and Ag—Ru. In another embodiment, the heterogeneous reduction catalyst contains at least one metal selected from Co, Ni and Cu and the loading is about 0.5 weight % to about 99 weight % (e.g., bulk use, such as a Raney Ni catalyst). In another embodiment, the heterogeneous reduction catalyst contains at least one metal selected from Ag, Ru, Pd and Pt and the loading about 0.01 weight % to about 15 weight %, or about 0.1 weight % to about 10 weight %. For a bimetallic catalyst, the molar ratio of metal 1 to metal 2 (M1:M2) may vary from about 25:1 to about 1:25 or from about 25:1 to about 2:1 or from about 20:1 to about 5:1.

The heterogeneous reduction catalyst may be modified with one or more metals. Suitable modifiers include Mn, Co, Au, W, Cu, Zn, Mo, Sb, Bi and Pb. In one variation, the heterogeneous reduction catalyst comprises two metals selected from the group consisting of Ni, Co, Cu, Ag, Pt, Pd, Fe and Ru and a modifier selected from the group consisting of Mn, Co, Au, W, Cu, Zn, Mo, Sb, Bi and Pb, such as a heterogeneous reduction catalyst comprising Co—Cu(Zn). In another variation, the heterogeneous reduction catalyst comprises three metals selected from the group consisting of Ni, Co, Cu, Ag, Pt, Pd, Fe and Ru, such as a heterogeneous reduction catalyst selected from the group consisting of Ni—Co—Cu, Ag—Co—Cu, Ni—Co—Ag. In another variation, the heterogeneous reduction catalyst comprises three metals selected from the group consisting of Ni, Co, Cu, Ag, Pt, Pd, Fe, Sc, Ti, V, Mn, Zn and Ru. In one variation, the catalyst is modified with Au, W, Cu, Zn, Sb, Bi and Pb. In another variation, the catalyst is modified with Au, Cu, Zn, Sb, Bi and Pb. In yet another variation, the catalyst is modified with Mn. Exemplary modified catalysts include modified Ni, Co and Cu catalysts such as Ni(Cu), Co(Cu), Cu(Zn) and Ni(Co—Cu). Another exemplary modified catalyst is Cu(Mn). In one embodiment, the molar ratio of catalyst to modifier (catalyst:modifier) is about 200:1 to about 1:10, or about 100:1 to about 1:2, or about 50:1 to about 1:1.

The heterogeneous reduction catalyst may be supported. Suitable catalyst supports include carbons, aluminas, zirconias, silicas, alumina-silicas, titanias, alumina-titanias, silicon carbides and mixed phases thereof. The catalyst supports may occur in a variety of shapes, for example, extruded shapes and pressed shapes, including but not limited to spheres, extrudates, pellets (cut extrudates), trilobes, quatralobes, rings and pentarings as described in the 2014 Saint-Gobain NorPro Catalytic Products brochure and website. Exemplary shapes include extrudates, spheres, beads, cylinders, pellets, tablets, multi-lobed shapes, rings, stars, ripped cylinders, triholes, alphas, wheels, and the like. Formulating the catalyst on a shaped support is useful to prevent excessive back pressure during the operation of fixed bed reactors on commercial scale. Catalysts formulations may be distributed uniformly across the shaped support or may be distributed as an outer shell on the support, or an egg yolk or a band beneath the outer surface of the shaped support. When two or metals are present in the catalyst formulation, structure shells containing different metal compositions across the shell are possible. In one embodiment, the catalyst support is a sphere, pellet, cylinder, etc. having a diameter greater than 0.8 mm.

In one embodiment, the temperature range for the reaction of HMF with hydrogen is about 50° C. to about 150° C. In another embodiment, the reaction temperature is about 80° C. to about 130° C.

In one embodiment, the hydrogen pressure for the reaction of HMF with hydrogen is about 50 psi to about 2000 psi. In another embodiment, the hydrogen pressure is about 100 psi to about 1500 psi. In still another embodiment, the hydrogen pressure is about 200 psi to about 1000 psi.

In one aspect, BHMF (2) is formed from HMF (1) over an on-stream period of at least about 150 hours. In some embodiments, BHMF is formed over an on-stream period of at least about 300 hours. In further embodiments, BHMF is formed from HMF over an on-stream period of at least about any of 150, 500, 1,000, 2,000, 3,000, 5,000, 8,000 and 10,000 hours or more. In one aspect, BHMF is formed from HMF over an on-stream period of at least a value provided herein, but less than 30,000 or 15,000 or 12,000 or 10,000 hours. In one aspect, BHMF is formed from HMF over an on-stream period of between about any of 150-10,000, 500-10,000, 1,000-10,000, 5,000-10,000, 150-8,000, 300-5,000, 500-3,000, 1,000-8,000, 3,000-8,000, and 5,000-7,000 hours. In some embodiments, BHMF is formed over an on-stream period of between one and five or one and three days. For any of the time periods described for which BHMF is formed, in one variation, the embodiment further comprises (i) maintaining catalyst selectivity of at least about 90%, 95%, or 99% over such time period or (ii) producing BHMF in a yield of at least about 85%, 90%, 95%, or 99% over such period; or both (i) and (ii).

In one aspect, HMF (1) is fed to a continuous flow reactor over an on-stream period of at least about 150 hours. In some embodiments, HMF is fed to a continuous flow reactor over an on-stream period of at least about 300 hours. In further embodiments, HMF is fed to a continuous flow reactor over an on-stream period of at least about any of 150, 500, 1,000, 2,000, 3,000, 5,000, 8,000 and 10,000 hours or more. In one aspect, HMF is fed to a continuous flow reactor over an on-stream period of at least a value provided herein, but less than 30,000 or 15,000 or 12,000 or 10,000 hours. In one aspect, HMF is fed to a continuous flow reactor over an on-stream period of between about any of 150-10,000, 500-10,000, 1,000-10,000, 5,000-10,000, 150-8,000, 300-5,000, 500-3,000, 1,000-8,000, 3,000-8,000, and 5,000-7,000 hours. In some embodiments, HMF is fed to a continuous flow reactor over an on-stream period of between one and five or one and three days. For any of the time periods described for which HMF is fed to the continuous flow reactor, in one variation, the embodiment further comprises (i) maintaining catalyst selectivity of at least about 90%, 95%, or 99% over such time period or (ii) producing BHMF in a yield of at least about 85%, 90%, 95%, or 99% over such period; or both (i) and (ii).

BHMF in one aspect is formed from HMF with at least about 90% selectivity. In some embodiments, BHMF is formed from HMF with at least about 95% selectivity. In some embodiments, BHMF is formed from HMF with at least about 99% selectivity. The transformation of HMF to BHMF is carried out in a continuous flow reactor by a heterogeneous reduction catalyst.

In one variation, at least 85% of HMF is converted to BHMF. In some embodiments, at least 90% HMF is converted to BHMF. In some embodiments, at least 95% HMF is converted to BHMF. In some embodiments, at least 99% HMF is converted to BHMF.

In a particular variation, the transformation of HMF (1) to BHMF (2) is carried out in a continuous flow reactor by a heterogeneous reduction catalyst, forming BHMF with at least about 80% or 85% or 90% or 95% or 99% selectivity and with an HMF conversion of at least 75% or 80% or 85% or 90% or 95% or 99%. In one variation the transformation of HMF (1) to BHMF (2) is carried out on a commercial scale.

Also provided is a reactor effluent stream comprising BHMF produced by the method of converting HMF to BHMF as detailed herein. It is understood that a reactor zone effluent stream comprising BHMF may also be produced by the method of converting HMF to BHMF as detailed herein.

Conversion of BHMF (2) to BHMTHF (3)

Organic solvents, such as alcohols, esters, ethers and mixtures thereof, are suitable for the conversion of BHMF (2) to BHMTHF (3). Exemplary alcohols include ethanol, n-propanol, isopropanol, n-butanol, t-butanol, iso-butanol and sec-butanol. Exemplary esters include methyl acetate, ethyl acetate, propyl acetate and butyl acetate. Exemplary ethers include dioxane, dioxolane, glyme, diglyme, triglyme and tetraglyme. In one embodiment, the organic solvent contains less than about 25 weight % water. In another embodiment, the organic solvent contains less than about 10 weight % water. In another embodiment, the organic solvent contains less than about 5 weight % water. In another embodiment, the organic solvent is substantially free of water. In another embodiment, the organic solvent contains water. In one embodiment, an organic solvent contains up to about 50 weight % water. In another embodiment an organic solvent contains up to about 25 weight % water or up to about 10 weight % water. In another embodiment, the organic solvent contains between about 5 and 25 weight % water, between about 15 and 25 weight % water, or between about 10 and 20 weight % water. In one embodiment, the organic solvent is an azeotropic mixture comprising water. In one embodiment, the organic solvent is dioxane that contains between about 10 and 20 weight % water. In one embodiment, the organic solvent is isopropanol that contains between about 10 and 20 weight % water. In one embodiment, the organic solvent is glyme that contains between about 10 and 20 weight % water. The use of an organic solvent has been shown to improve catalyst performance (see Example 2 and Comparative Example 4).

The conversion of BHMF (2) to BHMTHF (3) may be carried out under conditions in which less than 50 weight % water is present. In one embodiment, the conversion of BHMF to BHMTHF is carried out under conditions in which less than 25 weight % water is present. In another embodiment, the conversion of BHMF to BHMTHF is carried out under conditions in which less than 20 weight % water is present. In another embodiment, the conversion of BHMF to BHMTHF is carried out under conditions in which less than 10 weight % water is present. In another embodiment, the conversion of BHMF to BHMTHF is carried out under conditions in which less than 5 weight % water is present.

Suitable heterogeneous reduction catalysts for the conversion of BHMF (2) to BHMTHF (3) are those that contain at least one metal selected from Ni, Co, Cu, Ag, Pt, Pd and Ru or a combination thereof. In one embodiment, the heterogeneous reduction catalyst contains at least one metal selected from Ni, Co, Pd, Ru and Pt. In another embodiment, the heterogeneous reduction catalyst contains at least one metal selected from Ni, Pd, Co and Pt. Exemplary metal combinations include Co—Cu, Ni—Cu, Ru—Cu, Ag—Ni, Ag—Co, Ag—Ru and Cu—Co—Ni. In another embodiment, the heterogeneous reduction catalyst contains at least one metal selected from Co, Ni and Cu and the loading is about 0.5 weight % to about 99 weight % (e.g., bulk use, such as a Raney Ni catalyst). In another embodiment, the heterogeneous reduction catalyst contains at least one metal selected from Ag, Ru, Pd and Pt and the loading about 0.01 weight % to about 15 weight %, or about 0.1 weight % to about 10 weight %. For a bimetallic catalyst, the molar ratio of metal 1 to metal 2 (M1:M2) may vary from about 25:1 to about 1:25 or from about 25:1 to about 2:1 or from about 20:1 to about 5:1.

The heterogeneous reduction catalyst may be modified with one or more metals. Suitable modifiers include Mn, Co, Au, W, Cu, Zn, Mo, Sb, Bi and Pb. Exemplary modified catalysts include modified Ni, Co and Cu catalysts such as Ni(Cu), Co(Cu), Cu(Zn) and Ni(Co—Cu). Another exemplary modified catalyst is Cu(Mn). In one embodiment, the molar ratio of catalyst to modifier (catalyst:modifier) is about 200:1 to about 1:10, or about 100:1 to about 1:2, or about 50:1 to about 1:1.

The heterogeneous reduction catalyst may be supported. Suitable catalyst supports include carbons, aluminas, zirconias, silicas, alumina-silicas, titanias, alumina-titanias, silicon carbides and mixed phases thereof. The catalyst supports may occur in a variety of shapes, for example, extruded shapes, spheres, beads, cylinders, pellets, tablets, multi-lobed shapes, rings, stars, ripped cylinders, triholes, alphas, wheels, and the like.

In one embodiment, the temperature range for the reaction of BHMF with hydrogen is about 50° C. to about 150° C. In another embodiment, the reaction temperature is about 80° C. to about 130° C.

In one embodiment, the hydrogen pressure for the reaction of BHMF with hydrogen is about 50 psi to about 2000 psi. In another embodiment, the hydrogen pressure is about 100 psi to about 1500 psi. In still another embodiment, the hydrogen pressure is about 200 psi to about 1000 psi.

In one aspect, BHMTHF (3) is formed from BHMF (2) over an on-stream period of at least 150 hours. In some embodiments, BHMTHF is formed from BHMF over an on-stream period of at least 300 hours. In further embodiments, BHMTHF is formed from BHMF over an on-stream period of at least about any of 500, 1,000, 2,000, 3,000, 5,000, 8,000 and 10,000 hours or more. In one aspect, BHMTHF is formed from BHMF over an on-stream period of at least a value provided herein but less than 15,000 or 12,000 or 10,000 hours. In one aspect, BHMTHF is formed from BHMF over an on-stream period of between about any of 150-10,000, 500-10,000, 1,000-10,000, 5,000-10,000, 150-8,000, 300-5,000, 500-3,000, 1,000-8,000, 3,000-8,000, and 5,000-7,000 hours. For any of the time periods described for which BHMF is fed to the continuous flow reactor, in one variation, the embodiment further comprises (i) maintaining catalyst selectivity of at least about 90%, 95%, or 99% over such time period or (ii) producing BHMTHF in a yield of at least about 85%, 90%, 95%, or 99% over such period; or both (i) and (ii).

BHMTHF in one aspect is formed from BHMF with at least about 90% selectivity. In some embodiments, BHMTHF is formed from BHMF with at least about 95% selectivity. In some embodiments, BHMTHF is formed from BHMF with at least about 99% selectivity. The transformation of BHMF to BHMTHF is carried out in a continuous flow reactor by a heterogeneous reduction catalyst.

In one variation, at least 85% of BHMF is converted to BHMTHF. In some embodiments, at least 90% BHMF is converted to BHMTHF. In some embodiments, at least 95% BHMF is converted to BHMTHF. In some embodiments, at least 99% BHMF is converted to BHMTHF.

In a particular variation, the transformation of BHMF (2) to BHMTHF (3) is carried out in a continuous flow reactor by a heterogeneous reduction catalyst, forming BHMTHF with at least about 80% or 85% or 90% or 95% or 99% selectivity and with a BHMF conversion of at least 75% or 80% or 85% or 90% or 95% or 99%. In some variations, the transformation of BHMF (2) to BHMTHF (3) is carried out on a commercial scale.

Also provided is a reactor effluent stream comprising BHMTHF produced by the method of converting BHMF to BHMTHF as detailed herein. It is understood that a reactor zone effluent stream comprising BHMTHF produced by the method of converting BHMF to BHMTHF as detailed herein is also provided.

The catalyst composition may be the same as or different from the catalyst composition used for the HMF to BHMF conversion. Similarly, the process conditions (e.g., reaction temperature, hydrogen pressure, flow rate) may be the same as or different from the process conditions used for the HMF to BHMF conversion.

Consecutive Conversion of HMF (1) to BHMF (2) to BHMTHF (3)

In one aspect, HMF (1) is converted to BHMF (2) and the BHMF so produced is converted to BHMTHF (3) without isolating or purifying the BHMF, but rather passing the BHMF directly to the catalyst used for the conversion of BHMF to BHMTHF.

Suitable organic solvents and heterogeneous reduction catalysts for the conversion of HMF (1) to BHMF (2) and the conversion of BHMF (2) to BHMTHF (3) are as described above.

The catalyst composition for the HMF (1) to BHMF (2) conversion may be the same as or different from the catalyst composition for the BHMF (2) to BHMTHF (3) conversion. In one aspect, the catalyst composition for the HMF to BHMF conversion is the same as the catalyst composition for the conversion of BHMF to BHMTHF. In one aspect, the catalyst composition for the HMF to BHMF conversion is different from the catalyst composition for the conversion of BHMF to BHMTHF. Similarly, the catalyst support for the HMF to BHMF conversion may be the same as or different from the catalyst support for the BHMF to BHMTHF conversion. In one embodiment, the catalyst support is the same. In another embodiment, the catalyst support is different.

The conversion of HMF to BHMF and the conversion of BHMF to BHMTHF may be carried out on the same or different continuous flow reactors or in the same or different reaction zones within a continuous flow reactor. In one embodiment, the conversion of HMF to BHMF and the conversion of BHMF to BHMTHF are carried out two different continuous flow reactors. In another embodiment, the conversion of HMF to BHMF and the conversion of BHMF to BHMTHF are carried out in two different reaction zones within a continuous flow reactor. In another embodiment, the conversion of HMF to BHMF and the conversion of BHMF to BHMTHF are carried out in the same reaction zone within a continuous flow reactor.

HMF may be reduced to BHMF using a heterogeneous reduction catalyst containing metals known to be more mild reduction catalysts such as Cu, Ag (and Pt). The reduction of BHMF to BHMTHF typically requires a catalyst containing metals known to be stronger reduction catalysts such as Ni, Co, Pd and Ru. In some embodiments, metals such as Pt, Ni or Co are used as a single catalyst in the consecutive reduction of HMF to BHMF to BHMTHF.

Suitable conditions (e.g., reaction temperature, hydrogen pressure, flow rate, solvent) for the conversion of HMF (1) to BHMF (2) and the conversion of BHMF (2) to BHMTHF (3) are as described above. The process conditions for the HMF to BHMF conversion may be the same as or different from the process conditions for the BHMF to BHMTHF conversion. In some embodiments the process conditions are the same. In other embodiments the process conditions are different. In some embodiments, the temperature of the BHMF to BHMTHF conversion is different from the temperature of the HMF to BHMF conversion. In one embodiment, the temperature of the BHMF to BHMTHF conversion is higher than the temperature of the HMF to BHMF conversion. In some embodiments, the conversion of HMF to BHMF and the conversion of BHMF to BHMTHF are carried out in the same solvent. In some embodiments, the conversion of HMF to BHMF and the conversion of BHMF to BHMTHF are carried out in different solvents.

In one embodiment, the temperature of the HMF (1) to BHMF (2) conversion is about 70° C. to about 120° C. or about 70° C. to about 100° C. In one embodiment, the temperature of the BHMF (2) to BHMTHF (3) conversion is about 80° C. to about 150° C. or about 80° C. to about 130° C.

In one embodiment, the consecutive conversion of HMF (1) to BHMF (2) to BHMTHF (3) is conducted using a guard column and a single catalyst in a single reactor with two temperature zones. In another embodiment, the consecutive conversion of HMF to BHMF to BHMTHF is conducted using a guard column and a single catalyst in a single reactor with a single temperature zone. In another embodiment, the consecutive conversion of HMF to BHMF to BHMTHF is conducted using a guard column and two catalysts in two reactors (e.g., one catalyst per reactor where the catalysts are different from each other) arranged in sequence, and the temperatures of the two reactors are the same or different.

BHMTHF in one aspect is formed from BHMF with at least about 90% selectivity. In some embodiments, BHMTHF is formed from BHMF with at least about 95% selectivity. In some embodiments, BHMTHF is formed from BHMF with at least about 99% selectivity.

In one aspect, at least 85% of HMF is converted to BHMTHF. In some embodiments, at least 90% of HMF is converted to BHMTHF.

In one aspect, BHMTHF is formed from the consecutive conversion of HMF to BHMF to BHMTHF over an on-stream period of at least 150 hours. In some embodiments, BHMTHF is formed from the consecutive conversion of HMF to BHMF to BHMTHF over an on-stream period of at least 300 hours. In further embodiments, BHMTHF is formed from the consecutive conversion of HMF to BHMF to BHMTHF over an on-stream period of at least about any of 500, 1,000, 2,000, 3,000, 5,000, 8,000 and 10,000 hours or more. In one aspect, BHMTHF is formed from the consecutive conversion of HMF to BHMF to BHMTHF over an on-stream period of at least a value provided herein but less than 15,000 or 12,000 or 10,000 hours. In one aspect, BHMTHF is formed from the consecutive conversion of HMF to BHMF to BHMTHF over an on-stream period of between about any of 150-10,000, 500-10,000, 1,000-10,000, 5,000-10,000, 150-8,000, 300-5,000, 500-3,000, 1,000-8,000, 3,000-8,000, and 5,000-7,000 hours. For any of the time periods described for which HMF is fed to the continuous flow reactor, in one variation, the embodiment further comprises (i) maintaining catalyst selectivity of at least about 90%, 95%, or 99% over such time period or (ii) producing BHMTHF in a yield of at least about 85%, 90%, 95%, or 99% over such period; or both (i) and (ii).

BHMTHF in one aspect is formed from the consecutive conversion of HMF to BHMF to BHMTHF with at least about 90% selectivity at each step in the conversion. In some embodiments, BHMTHF is formed from the consecutive conversion of HMF to BHMF to BHMTHF with at least about 95% selectivity at each step in the conversion. In some embodiments, BHMTHF is formed from the consecutive conversion of HMF to BHMF to BHMTHF with at least about 99% selectivity at each step in the conversion. The consecutive conversion of HMF to BHMF to BHMTHF may be carried out in a continuous flow reactor by a heterogeneous reduction catalyst.

In one variation, BHMTHF is produced with a conversion of at least 85% at each step of the consecutive conversion of HMF to BHMF to BHMTHF. In some embodiments, BHMTHF is produced with a conversion of at least 90% at each step of the consecutive conversion of HMF to BHMF to BHMTHF. In some embodiments, BHMTHF is produced with a conversion of at least 95% at each step of the consecutive conversion of HMF to BHMF to BHMTHF. In some embodiments, BHMTHF is produced with a conversion of at least 99% at each step of the consecutive conversion of HMF to BHMF to BHMTHF.

In a particular variation, the consecutive conversion of HMF to BHMF to BHMTHF is carried out in a continuous flow reactor by a heterogeneous reduction catalyst, forming BHMTHF with at least about 80% or 85% or 90% or 95% or 99% selectivity and with a conversion of at least 75% or 80% or 85% or 90% or 95% or 99% at each step of the consecutive conversion of HMF to BHMF to BHMTHF. In some variations, the consecutive conversion of HMF to BHMF to BHMTHF is carried out on a commercial scale.

Also provided is a reactor effluent stream comprising BHMTHF produced by the consecutive conversion of HMF to BHMF to BHMTHF, as detailed herein. It is understood that a reactor zone effluent stream comprising BHMTHF produced by the method of converting HMF to BHMF to BHMTHF as detailed herein is also provided.

In one variation, the consecutive conversion of HMF to BHMF to BHMTHF employs the use of a guard bed by feeding HMF through a guard bed comprising a transition metal to a continuous flow reactor. Alternatively or in addition, in another variation, the consecutive conversion of HMF to BHMF to BHMTHF employs HMF as a feedstock at about or greater than about any of 5, 6, 10, 12 or 15 weight percent or more.

In some embodiments the consecutive conversion of HMF (1) produces a mixture of BHMF (2) and BHMTHF (3).

Conversion of BHMTHF (3) to HTO (4)

Solvents such water, alcohols, esters, ethers, ketones and mixtures thereof are suitable for the conversion of BHMTHF (3) to HTO (4). Exemplary alcohols include ethanol, n-propanol, isopropanol, n-butanol, t-butanol, iso-butanol and sec-butanol. Exemplary esters include methyl acetate, ethyl acetate, propyl acetate and butyl acetate. Exemplary ethers include dioxane, dioxolane, glyme, diglyme, triglyme and tetraglyme. In one embodiment, the solvent is an organic solvent that contains less than about 25 weight % water. In another embodiment, the organic solvent contains less than about 10 weight % water. In another embodiment, the organic solvent contains less than about 5 weight % water. In another embodiment, the organic solvent is substantially free of water. In another embodiment, the organic solvent contains water. In one embodiment, an organic solvent contains up to about 50 weight % water. In another embodiment an organic solvent contains up to about 25 weight % water or up to about 10 weight % water. In one embodiment, the organic solvent contains between about 5 and 25 weight % water, between about 15 and 25 weight % water, or between about 10 and 20 weight % water. In one embodiment, the organic solvent is an azeotropic mixture comprising water. In one embodiment, the organic solvent is dioxane that contains between about 10 and 20 weight % water. In one embodiment, the organic solvent is isopropanol that contains between about 10 and 20 weight % water. In one embodiment, the organic solvent is glyme that contains between about 10 and 20 weight % water. In one embodiment, the solvent is water.

The conversion of BHMTHF (3) to HTO (4) may be carried out under conditions in which less than 50 weight % water is present. In one embodiment, the conversion of BHMTHF to HTO is carried out under conditions in which less than 25 weight % water is present. In another embodiment, the conversion of BHMTHF to HTO is carried out under conditions in which less than 20 weight % water is present. In another embodiment, the conversion of BHMTHF to HTO is carried out under conditions in which less than 10 weight % water is present. In another embodiment, the conversion of BHMTHF to HTO is carried out under conditions in which less than 5 weight % water is present.

Suitable heterogeneous reduction catalysts for the conversion of BHMTHF (3) to HTO (4) are supported heterogeneous catalysts comprising Pt. In certain embodiments of the present invention where the catalyst comprises platinum, platinum is present as Pt(0), which can be used alone or in combination with other metals and/or alloys, and which is present on at least an external surface of a support (i.e., a surface exposed to the reaction constituents). In accordance with certain embodiments of the present invention, the catalysts employed in the processes comprise Pt and at least one metal selected from the group of Mo, La, Sm, Y, W, and Re (M2). In various embodiments of the invention one or more other d-block metals, one or more rare earth metals (e.g., lanthanides), and/or one or more main group metals (e.g., Al) may also be present in combination with the Pt and M2 combinations. Typically, the total weight of metal(s) is from about 0.1% to about 10%, or from 0.2% to 10%, or from about 0.2% to about 8%, or from about 0.2% to about 5%, of the total weight of the catalyst. In some embodiments the total weight of metal of the catalyst is less than about 4%. The molar ratio of Pt (M1) to (M2) may vary, for example, from about 20:1 to about 1:10. In one embodiment, the M1:M2 molar ratio is in the range of from about 10:1 to about 1:5. In another embodiment, the ratio of M1:M2 is in the range of about 8:1 to about 1:2.

In one embodiment, the catalyst is a supported heterogeneous catalyst, wherein the catalyst is on the surface of the support. Suitable supports include, for example, acidic ion-exchange resin, gamma alumina, fluorinated alumina, sulfate or tungstate promoted zirconia, titania, silica, silica promoted alumina, aluminum phosphate, tungsten oxide supported on silica-alumina, acidic clay, supported mineral acid, and zeolites. The support materials may be modified using methods known in the art such as heat treatment, acid treatment or by the introduction of a dopant (for example, metal-doped titanias, metal-doped zirconias (e.g., tung-stated-zirconia), metal-doped cerias, and metal-modified niobias). In one embodiment, the catalyst support is selected from zirconias, silicas, and zeolites. When a catalyst support is used, the metals may be deposited using procedures known in the art including, but not limited to incipient wetness, ion-exchange, deposition-precipitation, and vacuum impregnation. When two or more metals are deposited on the same support, they may be deposited sequentially or simultaneously. In various embodiments, following metal deposition, the catalyst is dried at a temperature in the range of about 20° C. to about 120° C. for a period of time ranging from at least about 1 hour to about 24 hours. In these and other embodiments, the catalyst is dried under sub-atmospheric pressure conditions. In various embodiments, the catalyst is reduced after drying (e.g., by flowing 5% $H_2$ in $N_2$ at a temperature of at least about 200° C. for a period of time (e.g., at least about 3 hours)). Still further, in these and other embodiments, the catalyst is calcined in air at a temperature of at least about 200° C. for a period of time of at least about 3 hours.

In one embodiment, the conversion of BHMTHF (3) to HTO (4) is conducted at temperatures in the range of from about 60° C. to about 200° C. In another embodiment, the conversion of BHMTHF to HTO is conducted at temperatures in the range of from about 80° C. to about 200° C. In another embodiment, the conversion is conducted at temperatures in the range of from about 100° C. to about 180° C.

In one embodiment, the conversion of BHMTHF (3) to HTO (4) is conducted at hydrogen pressures in the range of from about 200 psi to about 2000 psi. In another embodiment, the conversion of BHMTHF to HTO is conducted at hydrogen pressures in the range of from about 50 psi to about 2000 psi.

In one aspect, HTO (4) is formed from BHMTHF (3) over an on-stream period of at least about 150 hours. In some embodiments, HTO is formed from BHMTHF over an on-stream period of at least about 300 hours. In further embodiments, HTO is formed from BHMTHF over an on-stream period of at least about any of 500, 1,000, 2,000, 3,000, 5,000, 8,000 and 10,000 hours or more. In one aspect, HTO is formed from BHMTHF over an on-stream period of at least a value provided herein but less than 15,000 or 12,000 or 10,000 hours. In one aspect, HTO is formed from BHMTHF over an on-stream period of between about any of 150-10,000, 500-10,000, 1,000-10,000, 5,000-10,000, 150-8,000, 300-5,000, 500-3,000, 1,000-8,000, 3,000-8,000 and 5,000-7,000 hours. For any of the time periods described for which BHMTHF is fed to the continuous flow reactor, in one variation, the embodiment further comprises (i) maintaining catalyst selectivity of at least about 90%, 95%, or 99% over such time period or (ii) producing HTO in a yield of at least about 85%, 90%, 95%, or 99% over such period; or both (i) and (ii).

In some embodiments, HTO (4) and HDO (5) are formed. In one aspect, the combined selectivity for HTO and HDO is at least about 75%. In some embodiments, HTO and HDO are formed from BHMTHF with at least about 80% combined selectivity. In some embodiments, HTO and HDO are formed from BHMTHF with at least about 85% combined selectivity. In other embodiments, HTO and HDO are formed from BHMTHF with at least about 90% combined selectivity. In still other embodiments, HTO and HDO are formed from BHMTHF with at least about 95% combined selectivity. For any of the time periods described for which BHMTHF is fed to the continuous flow reactor, in one variation, the embodiment further comprises (i) maintaining catalyst selectivity of at least about 90%, 95%, or 99% over such time period or (ii) producing HTO and/or HDO in a yield of at least about 85%, 90%, 95%, or 99% over such period; or both (i) and (ii).

In other embodiments, HTO (4) is formed selectively, for example, by reducing the temperature or time at which the conversion is conducted. Accordingly, in one aspect, the selectivity for HTO is at least about 80%. In some embodiments, HTO is formed from BHMTHF with at least about 85% selectivity. In some embodiments, HTO is formed from BHMTHF with at least about 90% selectivity. In some embodiments, HTO is formed from BHMTHF with at least about 95% selectivity.

In one variation, at least 50% BHMTHF is converted to HTO and HDO. In some embodiments, at least 60% BHMTHF is converted to HTO and HDO. In some embodiments, at least 70% BHMTHF is converted to HTO and HDO. In some embodiments, at least 80% BHMTHF is converted to HTO and HDO. In some embodiments, at least 90% BHMTHF is converted to HTO and HDO. In other embodiments, at least 95% BHMTHF is converted to HTO and HDO. In still other embodiments, at least 99% BHMTHF is converted to HTO and HDO.

In a particular variation, the transformation of BHMTHF to HTO is carried out in a continuous flow reactor by a heterogeneous reduction catalyst comprising Pt, forming HTO and HDO with at least about 70% or 75% or 80% or 85% or 90% or 95% combined selectivity and with a BHMTHF conversion of at least 40% or 50% or 60% or 70% or 80% or 90% or 95% or 99%. In some variations, the transformation of BHMTHF to HTO is carried out on a commercial scale.

Also provided is a reactor effluent stream or a reactor zone effluent stream comprising HTO (4) and HDO (5) produced by the method of converting BHMTHF to HTO and HDO detailed herein. In some embodiments, the reactor effluent stream or reactor zone effluent stream comprises a mixture of BHMTHF, HTO, and HDO. The reactor effluent stream or reactor zone effluent stream may be recycled or fed back into the continuous flow reactor or reaction zone from which it exited in order to convert unreacted BHMTHF to HTO and HDO and/or to enrich the reactor effluent stream or reactor zone effluent stream in HTO or HDO. The reactor effluent stream or reactor zone effluent stream may be directly fed back into the continuous flow reactor in a concerted process, or it may be collected and fed back into the continuous flow reactor at a later time.

Consecutive Conversion of BHMF (2) to BHMTHF (3) to HTO (4)

In one variation, BHMF (which may be obtained from HMF as detailed throughout) is converted to BHMTHF and the BHMTHF so produced is converted to 1,2,6-hexanetriol (HTO) without isolating or purifying the BHMTHF, but rather passing the BHMTHF directly to the catalyst used for the conversion of the BHMTHF to HTO.

Suitable solvents and heterogeneous reduction catalysts for the conversion of BHMF (2) to BHMTHF (3) and the conversion of BHMTHF (3) to HTO (4) are as described above. The solvent for the conversion of BHMF (2) to BHMTHF (3) may be the same as or different from the solvent for the conversion of BHMTHF (3) to HTO (4). In one aspect, the solvent for the BHMF (2) to BHMTHF (3) conversion is the same as the solvent for the BHMTHF (3) to HTO (4) conversion. In one aspect, the solvent for the BHMF (2) to BHMTHF (3) conversion is different from the solvent for the BHMTHF (3) to HTO (4) conversion. When, for example, the solvent for the BHMF (2) to BHMTHF (3) conversion is an organic solvent and the solvent for the BHMTHF (3) to HTO (4) conversion is an aqueous solvent, a solvent transition or exchange using an evaporative method, e.g., distillation, or a membrane separation method is contemplated. When the solvent for the BHMF (2) to BHMTHF (3) conversion is an organic solvent and the solvent for the BHMTHF (3) to HTO (4) conversion is an aqueous solvent, the organic solvent may contain water, for example, less than 50 or 40 or 30 or 20 or 15 weight %, and the aqueous solvent may contain organic solvent, for example, less than 30 or 25 or 20 or 15 weight %. When the solvent for a conversion is an organic solvent and the solvent for the subsequent conversion is an aqueous solvent, the organic solvent may be substantially free of water and/or the aqueous solvent may be substantially free of organic solvent.

The catalyst composition for the BHMTHF to HTO conversion may be the same as or different from the catalyst composition for the BHMF to BHMTHF conversion. In one aspect, the catalyst composition for the BHMTHF to HTO conversion is the same as the catalyst composition for the conversion of BHMF to BHMTHF. In one aspect, the catalyst composition for the BHMTHF to HTO conversion is different from the catalyst composition for the conversion of BHMF to BHMTHF. Similarly, the catalyst support for the BHMTHF to HTO conversion may be the same as or different from the catalyst support for the BHMF to BHMTHF conversion. In one embodiment, the catalyst support is the same. In another embodiment, the catalyst support is different.

The conversion of BHMF to BHMTHF and the conversion of BHMTHF to HTO may be carried out on the same or different continuous flow reactors or in the same or different reaction zones within a continuous flow reactor. In one embodiment, the conversion of BHMF to BHMTHF and the conversion of BHMTHF to HTO are carried out two different continuous flow reactors. In another embodiment, the conversion of BHMF to BHMTHF and the conversion of BHMTHF to HTO are carried out in two different reaction zones within a continuous flow reactor. In another embodiment, the conversion of BHMF to BHMTHF and the conversion of BHMTHF to HTO are carried out in the same reaction zone within a continuous flow reactor.

In one embodiment, the temperature range for the consecutive conversion is about 80° C. to about 180° C. In another embodiment, the reaction temperature is about 100° C. to about 180° C.

In one embodiment, the hydrogen pressure for the consecutive conversion is about 50 psi to about 2000 psi. In another embodiment, the hydrogen pressure is about 100 psi to about 1500 psi. In still another embodiment, the hydrogen pressure is about 200 psi to about 1000 psi. The process conditions (e.g., reaction temperature, hydrogen pressure, flow rate) for the BHMTHF to HTO conversion may be the same as or different from the process conditions for the BHMF to BHMTHF conversion. In some embodiments the process conditions are the same. In other embodiments the process conditions are different. In some embodiments, the temperature of the BHMTHF to HTO conversion is different from the temperature of the BHMF to BHMTHF conversion.

In one embodiment, the consecutive conversion of BHMF to BHMTHF to HTO is conducted using a single catalyst in a single reactor with two temperature zones. In another embodiment, the consecutive conversion of BHMF to BHMTHF to HTO is conducted using two catalysts in a single reactor with two temperature zones (e.g., one catalyst per temperature zone, where the catalysts are different from each other). In another embodiment, the consecutive conversion of BHMF to BHMTHF to HTO is conducted using two catalysts in two reactors arranged in sequence (e.g., one catalyst per reactor where the catalysts are different from each other), and the temperatures of the two reactors are the same or different.

In one aspect, 1,2,6-hexanetriol (HTO) and 1,6-hexanediol (HDO) can be formed from BHMF with at least about 70% combined selectivity. In some embodiments, 1,2,6-hexanetriol (HTO) and 1,6-hexanediol (HDO) are formed from BHMF with at least about 80% combined selectivity. In other embodiments, 1,2,6-hexanetriol (HTO) and 1,6-hexanediol (HDO) are formed from BHMF with at least about 90% combined selectivity.

In other embodiments, 1,2,6-hexanetriol (HTO) is formed from BHMF selectively. In one embodiment, HTO (4) is formed from BHMF selectively by reducing the temperature at which the consecutive conversion is conducted. Accordingly, in one aspect, the selectivity for HTO is at least about 80%. In some embodiments, HTO is formed from BHMF with at least about 85% selectivity. In some embodiments, HTO is formed from BHMF with at least about 90% selectivity. In some embodiments, HTO is formed from BHMF with at least about 95% selectivity.

In one aspect, HTO is formed from the consecutive conversion of BHMF to BHMTHF to HTO over an on-stream period of at least 150 hours. In some embodiments, HTO is formed from the consecutive conversion of BHMF to BHMTHF to HTO over an on-stream period of at least 300 hours. In further embodiments, HTO is formed from the consecutive conversion of BHMF to BHMTHF to HTO over an on-stream period of at least about any of 500, 1,000, 2,000, 3,000, 5,000, 8,000 and 10,000 hours or more. In one aspect, HTO is formed from the consecutive conversion of BHMF to BHMTHF to HTO over an on-stream period of at least a value provided herein but less than 15,000 or 12,000 or 10,000 hours. In one aspect, HTO is formed from the consecutive conversion of BHMF to BHMTHF to HTO over an on-stream period of between about any of 150-10,000, 500-10,000, 1,000-10,000, 5,000-10,000, 150-8,000, 300-5,000, 500-3,000, 1,000-8,000, 3,000-8,000, and 5,000-7,000 hours. For any of the time periods described for which BHMF is fed to the continuous flow reactor, in one variation, the embodiment further comprises (i) maintaining catalyst selectivity of at least about 90%, 95%, or 99% over such time period or (ii) producing HTO in a yield of at least about 85%, 90%, 95%, or 99% over such period; or both (i) and (ii).

HTO in one aspect is formed from the consecutive conversion of BHMF to BHMTHF to HTO with at least about 70% selectivity at each step in the conversion. In some embodiments, HTO is formed from the consecutive conversion of BHMF to BHMTHF to HTO with at least about 80% selectivity at each step in the conversion. In some embodiments, HTO is formed from the consecutive conversion of BHMF to BHMTHF to HTO with at least about 90% selectivity at each step in the conversion. The consecutive conversion of BHMF to BHMTHF to HTO is carried out in a continuous flow reactor by a heterogeneous reduction catalyst.

In one variation, HTO is produced with a conversion of at least 85% at each step of the consecutive conversion of BHMF to BHMTHF to HTO. In some embodiments, HTO is produced with a conversion of at least 90% at each step of the consecutive conversion of BHMF to BHMTHF to HTO. In some embodiments, HTO is produced with a conversion of at least 95% at each step of the consecutive conversion of BHMF to BHMTHF to HTO. In some embodiments, HTO is produced with a conversion of at least 99% at each step of the consecutive conversion of BHMF to BHMTHF to HTO.

In a particular variation, the consecutive conversion of BHMF to BHMTHF to HTO is carried out in a continuous flow reactor by a heterogeneous reduction catalyst, forming HTO with at least about 70% or 75% or 80% or 85% or 90% or 95% selectivity and with a conversion of at least 75% or 80% or 85% or 90% or 95% or 99% at each step of the consecutive conversion of BHMF to BHMTHF to HTO. In some variations, the consecutive conversion of BHMF to BHMTHF to HTO is carried out on a commercial scale.

Also provided is a reactor effluent stream or reactor zone effluent stream comprising HTO (4) produced by the consecutive conversion of BHMF (2) to BHMTHF (3) to HTO (4) as detailed herein. In a particular aspect, the reactor effluent stream or reactor zone effluent stream contains no more than 10 weight % or 5 weight % or is substantially free of water. In another variation, the effluent stream comprising HTO further comprises water (e.g., when water is used as a solvent in the conversion of BHMTHF to HTO).

In one variation, the consecutive conversion of HMF to BHMF to BHMTHF to HTO employs the production of BHMF from HMF and the use of a guard bed by feeding HMF through a guard bed comprising a transition metal to a continuous flow reactor. Alternatively or in addition, in another variation, the consecutive conversion of BHMF to BHMTHF to HTO employs the production of BHMF from HMF as a feedstock at about or greater than about any of 5, 6, 10, 12 or 15 weight percent or more.

In some embodiments, the consecutive conversion of BHMF (2) produces a mixture of HTO (4) and BHMTHF (3).

Consecutive Conversion of HMF (1) to BHMF (2) to BHMTHF (3) to HTO (4)

In one aspect, HMF (1) is converted to BHMF (2), the BHMF so produced is converted to BHMTHF (3), and the BHMTHF so produced is converted to HTO (4) without isolating or purifying the BHMF or BHMTHF, but rather passing the BHMF directly to the catalyst used for the conversion of BHMF to BHMTHF and passing the BHMTHF directly to the catalyst used for the conversion of BHMTHF to HTO.

Suitable solvents and heterogeneous reduction catalysts for the conversion of HMF (1) to BHMF (2), the conversion of BHMF (2) to BHMTHF (3), and the conversion of BHMTHF (3) to HTO (4) are as described above. The solvent for the HMF (1) to BHMF (2) conversion may be the same as or different from the solvent for the BHMF (2) to BHMTHF (3) conversion, which solvent may be the same as or different from the solvent for the BHMTHF (3) to HTO (4) conversion. In one aspect, the solvent for the HMF (1) to BHMF (2) conversion is the same as the solvent for the BHMF (2) to BHMTHF (3) conversion, which is the same as the solvent for the BHMTHF (3) to HTO (4) conversion. In one aspect, the solvent for the HMF (1) to BHMF (2) conversion is different from the solvent for the BHMF (2) to BHMTHF (3) conversion, and the solvent for the BHMF (2) to BHMTHF (3) conversion is the same as the solvent for the BHMTHF (3) to HTO (4) conversion. In one aspect, the solvent for the HMF (1) to BHMF (2) conversion is different from the solvent for the BHMF (2) to BHMTHF (3) conversion, and the solvent for the BHMTHF (3) to HTO (4) conversion is the same as the solvent for the HMF (1) to BHMF (2) conversion. In one aspect, the solvent for the HMF (1) to BHMF (2) conversion is the same as the solvent for the BHMF (2) to BHMTHF (3) conversion, and the solvent for the BHMF (2) to BHMTHF (3) conversion is different from the solvent for the BHMTHF (3) to HTO (4) conversion. In one aspect, the solvent for the HMF (1) to BHMF (2) conversion is different from the solvent for the BHMF (2) to BHMTHF (3) conversion, and the solvent for the BHMF (2) to BHMTHF (3) conversion is different from the solvent for the BHMTHF (3) to HTO (4) conversion, and the solvent for the BHMTHF (3) to HTO (4) conversion is different from the solvent for the HMF (1) to BHMF (2) conversion. When, for example, the solvent for a conversion is an organic solvent and the solvent for the subsequent conversion is an aqueous solvent, a solvent transition or exchange using an evaporative method, e.g., distillation, or a membrane separation method is contemplated. For example, the solvents for the HMF (1) to BHMF (2) conversion and the BHMF (2) to BHMTHF (3) conversion may be the same or different organic solvents and the solvent for the BHMTHF (3) to HTO (4) conversion may be an aqueous solvent. When the solvent for a conversion is an organic solvent and the solvent for the subsequent conversion is an aqueous solvent, the organic solvent may contain water, for example, less than 50 or 40 or 30 or 20 or 15 weight %, and the aqueous solvent may contain organic solvent, for example, less than 30 or 25 or 20 or 15 weight %. When the solvent for a conversion is an organic solvent and the solvent for the subsequent conversion is an aqueous solvent, the organic solvent may be substantially free of water and/or the aqueous solvent may be substantially free of organic solvent.

In some variations, at least one of the conversion of HMF (1) to BHMF (2), the conversion of BHMF (2) to BHMTHF (3), and the conversion of BHMTHF (3) to HTO (4) is carried out in an organic solvent comprising less than about 25 weight % water. In some variations, the conversion of HMF (1) to BHMF (2), the conversion of BHMF (2) to BHMTHF (3), and the conversion of BHMTHF (3) to HTO (4) are each carried out in an organic solvent comprising less than about 25 weight % water. In one variation, all three conversions are carried out in the presence of dioxane. In another variation, all three conversions are carried out in the presence of isopropanol. In yet another variation, all three conversions are carried out in the presence of glyme.

In some variations, the conversion of HMF (1) to BHMF (2) is carried out in the presence of a heterogeneous reduction catalyst comprising Cu, the conversion of BHMF (2) to BHMTHF (3) is carried out in the presence of a heterogeneous reduction catalyst comprising Ni, and the conversion of BHMTHF (3) to HTO (4) is carried out in the presence of a heterogeneous reduction catalyst comprising Pt and optionally tungsten.

The catalyst composition for the HMF (1) to BHMF (2) conversion may be the same as or different from the catalyst composition for the BHMF (2) to BHMTHF (3) conversion, which catalyst composition may be the same as or different from the catalyst composition for the BHMTHF (3) to HTO (4) conversion. In one aspect, the catalyst composition for the HMF (1) to BHMF (2) conversion is the same as the catalyst composition for the BHMF (2) to BHMTHF (3) conversion, which is the same as the catalyst composition for the BHMTHF (3) to HTO (4) conversion. In one aspect, the catalyst composition for the HMF (1) to BHMF (2) conversion is different from the catalyst composition for the BHMF (2) to BHMTHF (3) conversion, and the catalyst composition for the BHMF (2) to BHMTHF (3) conversion is the same as the catalyst composition for the BHMTHF (3) to HTO (4) conversion. In one aspect, the catalyst composition for the HMF (1) to BHMF (2) conversion is different from the catalyst composition for the BHMF (2) to BHMTHF (3) conversion, and the catalyst composition for the BHMTHF (3) to HTO (4) conversion is the same as the catalyst composition for the HMF (1) to BHMF (2) conversion. In one aspect, the catalyst composition for the HMF (1) to BHMF (2) conversion is the same as the catalyst composition for the BHMF (2) to BHMTHF (3) conversion, and the catalyst composition for the BHMF (2) to BHMTHF (3) conversion is different from the catalyst composition for the BHMTHF (3) to HTO (4) conversion. In one aspect, the catalyst composition for the HMF (1) to BHMF (2) conversion is different from the catalyst composition for the BHMF (2) to BHMTHF (3) conversion, and the catalyst composition for the BHMF (2) to BHMTHF (3) conversion is different from the catalyst composition for the BHMTHF (3) to HTO (4) conversion, and the catalyst composition for the BHMTHF (3) to HTO (4) is different from the catalyst composition for the HMF (1) to BHMF (2) conversion.

In some embodiments, catalysts such as Pt—W are useful in the consecutive conversion of HMF to BHMF to BHMTHF to HTO.

The catalyst support for the HMF (1) to BHMF (2) conversion may be the same as or different from the catalyst support for the BHMF (2) to BHMTHF (3) conversion, which catalyst support may be the same as or different from the catalyst support for the BHMTHF (3) to HTO (4) conversion. In one aspect, the catalyst support for the HMF (1) to BHMF (2) conversion is the same as the catalyst support for the BHMF (2) to BHMTHF (3) conversion, which is the same as the catalyst support for the BHMTHF (3) to HTO (4) conversion. In one aspect, the catalyst support for the HMF (1) to BHMF (2) conversion is different from the catalyst support for the BHMF (2) to BHMTHF (3) conversion, and the catalyst support for the BHMF (2) to BHMTHF (3) conversion is the same as the catalyst support for the BHMTHF (3) to HTO (4) conversion. In one aspect, the catalyst support for the HMF (1) to BHMF (2) conversion is different from the catalyst support for the BHMF (2) to BHMTHF (3) conversion, and the catalyst support for the BHMTHF (3) to HTO (4) conversion is the same as the catalyst support for the HMF (1) to BHMF (2) conversion. In one aspect, the catalyst support for the HMF (1) to BHMF (2) conversion is the same as the catalyst support for the BHMF (2) to BHMTHF (3) conversion, and the catalyst support for the BHMF (2) to BHMTHF (3) conversion is different from the catalyst support for the BHMTHF (3) to HTO (4) conversion. In one aspect, the catalyst support for the HMF (1) to BHMF (2) conversion is different from the catalyst support for the BHMF (2) to BHMTHF (3) conversion, and the catalyst support for the BHMF (2) to BHMTHF (3) conversion is different from the catalyst support for the BHMTHF (3) to HTO (4) conversion, and the catalyst support for the BHMTHF (3) to HTO (4) is different from the catalyst support for the HMF (1) to BHMF (2) conversion.

Suitable conditions (e.g., reaction temperature, hydrogen pressure, flow rate) for the conversion of HMF (1) to BHMF (2), the conversion of BHMF (2) to BHMTHF (3) and the conversion of BHMTHF (3) to HTO (4) are as described above. The conditions for the HMF (1) to BHMF (2) conversion may be the same as or different from the conditions for the BHMF (2) to BHMTHF (3) conversion, which conditions may be the same as or different from the conditions for the BHMTHF (3) to HTO (4) conversion. In some embodiments the conditions for each conversion are the same. In other embodiments the conditions for each conversion are different. In some embodiments, the conditions for the HMF (1) to BHMF (2) conversion are different from the conditions for the BHMF (2) to BHMTHF (3) conversion, and the conditions for the BHMF (2) to BHMTHF (3) conversion are the same as the conditions for the BHMTHF (3) to HTO (4) conversion. In other embodiments, the conditions for the HMF (1) to BHMF (2) conversion are the same as the conditions for the BHMF (2) to BHMTHF (3) conversion, and the conditions for the BHMF (2) to BHMTHF (3) conversion are different from the conditions for the BHMTHF (3) to HTO (4) conversion.

In one embodiment, the consecutive conversion of HMF (1) to BHMF (2) to BHMTHF (3) to HTO (4) is conducted using a guard column and a single catalyst in a single reactor with two temperature zones. In another embodiment, the consecutive conversion of HMF (1) to BHMF (2) to BHMTHF (3) to HTO (4) is conducted using a guard column and a single catalyst in a single reactor with a single temperature zone. In another embodiment, the consecutive conversion of HMF (1) to BHMF (2) to BHMTHF (3) to HTO (4) is conducted using a guard column and two catalysts in a two reactors arranged in sequence, and the temperatures of the two reactors are the same or different. In still another embodiment, the consecutive conversion of HMF (1) to BHMF (2) to BHMTHF (3) to HTO (4) is conducted using a guard column and two catalysts in a single reactor (e.g., one catalyst per reactor where the catalysts are different from each other) with a single temperature zone or two temperature zones.

In one variation, the consecutive conversion of HMF (1) to BHMF (2) to BHMTHF (3) is conducted in a first continuous flow reactor, and the consecutive conversion of BHMTHF (3) to HTO (4) and optionally to HDO (5) is conducted in a second continuous flow reactor. In another variation, the consecutive conversion of HMF (1) to BHMF (2) to BHMTHF (3) is conducted in a first reaction zone within a continuous flow reactor, and the consecutive conversion of BHMTHF (3) to HTO (4) and optionally to HDO (5) is conducted in a second reaction zone. In a further variation, the consecutive conversion of HMF (1) to BHMF (2) to HTO (4) is conducted within multiple reaction zones within a first continuous flow reactor, and the conversion of HTO (4) to HDO (5) is conducted in a second continuous flow reactor. In some such variations, the first and second reaction zones are contained within the same continuous flow reactor. In some variations, the temperature is higher in the second continuous flow reactor or second reaction zone relative to the temperature in the first continuous flow reactor or first reaction zone. In some variations, the pressure is higher in the second continuous flow reactor or second reaction zone relative to the pressure in the first continuous flow reactor or first reaction zone. In some variations, the reactor effluent stream from the first continuous flow reactor is fed into the second continuous flow reactor without isolation or purification of the BHMTHF (3). In one variation, the consecutive conversion of HMF (1) to BHMF (2) to BHMTHF (3) in the first continuous flow reactor is carried out in the presence of a heterogeneous reduction catalyst comprising at least one metal selected from the group consisting of Co, Mn, Ni, and Cu or a combination thereof. In another variation, the consecutive conversion of BHMTHF (3) to HTO (4) and optionally to HDO (5) in the second continuous flow reactor is carried out in the presence of a heterogeneous reduction catalyst comprising Pt and optionally tungsten.

In one aspect, HTO can be formed from the consecutive conversion of HMF to BHMF to BHMTHF to HTO over an on-stream period of at least 150 hours. In some embodiments, HTO is formed from the consecutive conversion of HMF to BHMF to BHMTHF to HTO over an on-stream period of at least 300 hours. In further embodiments, HTO is formed from the consecutive conversion of HMF to BHMF to BHMTHF to HTO over an on-stream period of at least about any of 500, 1,000, 2,000, 3,000, 5,000, 8,000 and 10,000 hours or more. In one aspect, HTO is formed from the consecutive conversion of HMF to BHMF to BHMTHF to HTO over an on-stream period of at least a value provided herein but less than 15,000 or 12,000 or 10,000 hours. In one aspect, HTO is formed from the consecutive conversion of HMF to BHMF to BHMTHF to HTO over an on-stream period of between about any of 150-10,000, 500-10,000, 1,000-10,000, 5,000-10,000, 150-8,000, 300-5,000, 500-3,000, 1,000-8,000, 3,000-8,000, and 5,000-7,000 hours. For any of the time periods described for which HMF is fed to the continuous flow reactor, in one variation, the embodiment further comprises (i) maintaining catalyst selectivity of at least about 90%, 95%, or 99% over such time period or (ii) producing HTO in a yield of at least about 85%, 90%, 95%, or 99% over such period; or both (i) and (ii).

Also provided is a reactor effluent stream or reactor zone effluent stream comprising HTO (4) produced by the consecutive conversion of HMF (1) to BHMF (2) to BHMTHF (3) to HTO (4) as detailed herein. In a particular aspect, the reactor effluent stream or reactor zone effluent stream contains no more than 10 weight % or 5 weight % or is substantially free of water. In another variation, the reactor effluent stream or reactor zone effluent stream comprising HTO also comprises water, e.g., when water is used as a solvent in the conversion that produces HTO.

In one variation, the consecutive conversion of HMF (1) to BHMF (2) to BHMTHF (3) to HTO (4) employs the use of a guard bed by feeding HMF through a guard bed comprising a transition metal to a continuous flow reactor. Alternatively or in addition, in another variation, the consecutive conversion of HMF (1) to BHMF (2) to BHMTHF (3) to HTO (4) employs HMF as a feedstock at about or greater than about any of 5, 6, 10, 12 or 15 weight percent or more. Alternatively or in addition, in another variation, the consecutive conversion of HMF (1) to BHMF (2) to BHMTHF (3) to HTO (4) employs a continuous flow reactor. In some variations, the consecutive conversion of HMF (1) to BHMF (2) to BHMTHF (3) to HTO (4) is carried out on a commercial scale.

In some embodiments the consecutive conversion of HMF (1) produces a mixture of HTO (4) and HDO (5).

Conversion of BHMF (2) to HTO (4)

Solvents, such as water, alcohols, esters, ethers and mixtures thereof, are suitable for the conversion of BHMF to HTO. Exemplary alcohols include ethanol, n-propanol, isopropanol, n-butanol, t-butanol, iso-butanol and sec-butanol. Exemplary esters include methyl acetate, ethyl acetate, propyl acetate and butyl acetate. Exemplary ethers include dioxane, dioxolane, glyme, diglyme, triglyme and tetraglyme. In one embodiment, the solvent is an organic solvent that contains less than about 25 weight % water. In another embodiment, the organic solvent contains less than about 10 weight % water. In another embodiment, the organic solvent contains less than about 5 weight % water. In another embodiment, the organic solvent is substantially free of water. In another embodiment, the organic solvent contains water. In one embodiment, an organic solvent contains up to about 50 weight % water. In another embodiment an organic solvent contains up to about 25 weight % water or up to about 10 weight % water. In one embodiment, the organic solvent contains between about 5 and 25 weight % water, between about 15 and 25 weight % water, or between about 10 and 20 weight % water. In one embodiment, the organic solvent is an azeotropic mixture comprising water. In one embodiment, the organic solvent is dioxane that contains between about 10 and 20 weight % water. In one embodiment, the organic solvent is isopropanol that contains between about 10 and 20 weight % water. In one embodiment, the organic solvent is glyme that contains between about 10 and 20 weight % water.

The conversion of BHMF (2) to HTO (4) may be carried out under conditions in which less than 50 weight % water is present. In one embodiment, the conversion of BHMF to HTO is carried out under conditions in which less than 25 weight % water is present. In another embodiment, the conversion of BHMF to HTO is carried out under conditions in which less than 20 weight % water is present. In another embodiment, the conversion of BHMF to HTO is carried out under conditions in which less than 10 weight % water is present. In another embodiment, the conversion of BHMF to HTO is carried out under conditions in which less than 5 weight % water is present.

Suitable heterogeneous reduction catalysts for the conversion of BHMF to HTO are those that contain at least one metal selected from Co, Cu, Pt and Pd or a combination thereof. In one embodiment, the heterogeneous reduction catalyst contains at least one metal selected from Co and Cu. An exemplary metal combination is Co—Cu. In another embodiment, the heterogeneous reduction catalyst contains at least one metal selected from Co and Cu and the loading is about 0.5 weight % to about 99 weight % (e.g., bulk use). In another embodiment, the heterogeneous reduction catalyst contains at least one metal selected from Co and Cu and the loading is about 0.01 weight % to about 15 weight %, or about 0.1 weight % to about 10 weight %. For a bimetallic catalyst, the molar ratio of metal 1 to metal 2 (M1:M2) may vary from about 25:1 to about 1:25 or from about 25:1 to about 2:1 or from about 20:1 to about 5:1.

The heterogeneous reduction catalyst may be modified with one or more metals. Suitable modifiers include Mn, Co, Au, W, Cu, Zn, Mo, Sb, Bi, Pb, La, Sm, Y and Re. Exemplary modified catalysts include modified Pt, Co and Cu catalysts such as Pt(Cu), Co(Cu) and Pt(Co—Cu). In one embodiment, the molar ratio of catalyst to modifier (catalyst:modifier) is about 200:1 to about 1:10, or about 100:1 to about 1:2, or about 50:1 to about 1:1.

The heterogeneous reduction catalyst may be supported. Suitable catalyst supports include carbons, aluminas, zirconias, silicas, alumina-silicas, titanias, alumina-titanias, silicon carbides and mixed phases thereof. The catalyst supports may occur in a variety of shapes, for example, extruded shapes, spheres, beads, cylinders, pellets, tablets, multilobed shapes, rings, stars, ripped cylinders, triholes, alphas, wheels, and the like.

In one embodiment, the temperature range for the reaction of BHMF with hydrogen is about 50° C. to about 180° C. In another embodiment, the reaction temperature is about 80° C. to about 180° C.

In one embodiment, the hydrogen pressure for the reaction of BHMF with hydrogen is about 50 psi to about 2000 psi. In another embodiment, the hydrogen pressure is about 100 psi to about 1500 psi. In still another embodiment, the hydrogen pressure is about 200 psi to about 1000 psi.

In one aspect, HTO is formed from BHMF over an on-stream period of at least about 150 hours. In some embodiments, HTO is formed over an on-stream period of at least about 300 hours. In further embodiments, HTO is formed from BHMF over an on-stream period of at least about any of 500, 1,000, 2,000, 3,000, 5,000, 8,000 and 10,000 hours or more. In one aspect, HTO is formed from BHMF over an on-stream period of at least a value provided herein, but less than 30,000 or 15,000 or 12,000 or 10,000 hours. In one aspect, HTO is formed from BHMF over an on-stream period of between about any of 150-10,000, 500-10,000, 1,000-10,000, 5,000-10,000, 150-8,000, 300-5,000, 500-3,000, 1,000-8,000, 3,000-8,000, and 5,000-7,000 hours. For any of the time periods described for which BHMF is fed to the continuous flow reactor, in one variation, the embodiment further comprises (i) maintaining catalyst selectivity of at least about 90%, 95%, or 99% over such time period or (ii) producing HTO in a yield of at least about 85%, 90%, 95%, or 99% over such period; or both (i) and (ii).

HTO in one aspect is formed from BHMF with at least about 60% selectivity. In some embodiments, HTO is formed from BHMF with at least about 70% selectivity. In some embodiments, HTO is formed from BHMF with at least about 80% selectivity. In some embodiments, HTO is formed from BHMF with at least about 90% selectivity. The transformation of BHMF to HTO is carried out in a continuous flow reactor by a heterogeneous reduction catalyst.

In one variation, at least 60% of BHMF is converted to HTO. In some embodiments, at least 70% BHMF is converted to HTO. In some embodiments, at least 80% BHMF is converted to HTO. In some embodiments, at least 90% BHMF is converted to HTO.

In a particular variation, the transformation of BHMF to HTO is carried out in a continuous flow reactor by a heterogeneous reduction catalyst, forming HTO with at least about 65% or 70% or 75% or 80% or 85% or 90% or 95% selectivity and with a BHMF conversion of at least 65% or 70% or 75% or 80% or 85% or 90% or 95%. In some variations, the transformation of BHMF to HTO is carried out on a commercial scale.

Also provided is a reactor effluent stream or reactor zone effluent stream comprising HTO produced by the method of converting BHMF to HTO as detailed herein. In a particular aspect, the reactor effluent stream or reactor zone effluent stream comprising HTO contains no more than 10 weight % or 5 weight % or is substantially free of water. In another variation, the effluent stream comprising HTO further comprises water (e.g., when water is used as a solvent in the conversion of BHMF to HTO).

Consecutive Conversion of HMF (1) to BHMF (2) to HTO (4)

In one aspect, HMF is converted to BHMF and the BHMF so produced is converted to HTO without isolating or purifying the BHMF, but rather passing the BHMF directly to the catalyst used for the conversion of BHMF to HTO.

Suitable solvents and heterogeneous reduction catalysts for the conversion of HMF (1) to BHMF (2) and the conversion of BHMF (2) to HTO (4) are as described above. The solvent for the conversion of HMF (1) to BHMF (2) may be the same as or different from the solvent for the conversion of BHMF (2) to HTO (4). In one aspect, the solvent for the HMF (1) to BHMF (2) conversion is the same as the solvent for the BHMF (2) to HTO (4) conversion. In one aspect, the solvent for the HMF (1) to BHMF (2) conversion is different from the solvent for the BHMF (2) to HTO (4) conversion. When, for example, the solvent for the HMF (1) to BHMF (2) conversion is an organic solvent and the solvent for the BHMF (2) to HTO (4) conversion is an aqueous solvent, a solvent transition or exchange using an evaporative method, e.g., distillation, or a membrane separation method is contemplated. When the solvent for the HMF (1) to BHMF (2) conversion is an organic solvent and the solvent for the BHMF (2) to HTO (4) conversion is an aqueous solvent, the organic solvent may contain water, for example, less than 50 or 40 or 30 or 20 or 15 weight %, and the aqueous solvent may contain organic solvent, for example, less than 30 or 25 or 20 or 15 weight %. When the solvent for a conversion is an organic solvent and the solvent for the subsequent conversion is an aqueous solvent, the organic solvent may be substantially free of water and/or the aqueous solvent may be substantially free of organic solvent.

The catalyst composition for the HMF to BHMF conversion may be the same as or different from the catalyst composition for the BHMF to HTO conversion. In one aspect, the catalyst composition for the HMF to BHMF conversion is the same as the catalyst composition for the conversion of BHMF to HTO. In one aspect, the catalyst composition for the HMF to BHMF conversion is different from the catalyst composition for the conversion of BHMF to HTO. Similarly, the catalyst support for the HMF to BHMF conversion may be the same as or different from the catalyst support for the BHMF to HTO conversion. In one embodiment, the catalyst support is the same. In another embodiment, the catalyst support is different.

Suitable conditions (e.g., reaction temperature, hydrogen pressure, flow rate) for the conversion of HMF to BHMF and the conversion of BHMF to HTO are as described above. The process conditions for the HMF to BHMF conversion may be the same as or different from the process conditions for the BHMF to HTO conversion. In some embodiments the process conditions are the same. In other embodiments the process conditions are different. In some embodiments, the temperature of the BHMF to HTO conversion is different from the temperature of the HMF to BHMF conversion. In one embodiment, the temperature of the BHMF to HTO conversion is higher than the temperature of the HMF to BHMF conversion.

In one embodiment, the temperature of the HMF to BHMF conversion is about 70° C. to about 120° C. or about 70° C. to about 100° C. In one embodiment, the temperature of the BHMF to HTO conversion is about 50° C. to about 180° C. or about 80° C. to about 180° C. or about 80° C. to about 130° C.

In one embodiment, the hydrogen pressure for the reaction of BHMF with hydrogen is about 50 psi to about 2000 psi. In another embodiment, the hydrogen pressure is about 100 psi to about 1500 psi. In still another embodiment, the hydrogen pressure is about 200 psi to about 1000 psi.

In one embodiment, the consecutive conversion of HMF to BHMF to HTO is conducted using a guard column and a single catalyst in a single reactor with two temperature zones. In another embodiment, the consecutive conversion of HMF to BHMF to HTO is conducted using a guard column and a single catalyst in a single reactor with a single temperature zone. In another embodiment, the consecutive conversion of HMF to BHMF to HTO is conducted using a guard column and two catalysts in two reactors arranged in sequence (e.g., one catalyst per reactor where the catalysts are different from each other), and the temperatures of the two reactors are the same or different. In another embodiment, the consecutive conversion of HMF to BHMF to HTO is conducted using a guard column and two catalysts in a single reactor with a single temperature zone or two temperature zones (e.g., one catalyst per temperature zone, where the catalysts are different from each other).

In one aspect, HTO is formed from BHMF with at least about 60% selectivity. In some embodiments, HTO is formed with at least about 70% selectivity. In some embodiments, HTO is formed with at least about 80% selectivity. In some embodiments, HTO is formed from with at least about 90% selectivity.

In one aspect, at least 60% of HMF can be converted to HTO. In some embodiments, at least 70% HMF can be converted to HTO. In some embodiments, at least 80% HMF is converted to HTO. In some embodiments, at least 90% HMF is converted to HTO In one aspect, HTO is formed from the consecutive conversion of HMF to BHMF to HTO over an on-stream period of at least 150 hours. In some embodiments, HTO is formed from the consecutive conversion of HMF to BHMF to HTO over an on-stream period of at least 300 hours. In further embodiments, HTO is formed from the consecutive conversion of HMF to BHMF to HTO over an on-stream period of at least about any of 500, 1,000, 2,000, 3,000, 5,000, 8,000 and 10,000 hours or more. In one aspect, HTO is formed from the consecutive conversion of HMF to BHMF to HTO over an on-stream period of at least a value provided herein but less than 15,000 or 12,000 or 10,000 hours. In one aspect, HTO is formed from the consecutive conversion of HMF to BHMF to HTO over an on-stream period of between about any of 150-10,000, 500-10,000, 1,000-10,000, 5,000-10,000, 150-8,000, 300-5,000, 500-3,000, 1,000-8,000, 3,000-8,000, and 5,000-7,000 hours. For any of the time periods described for which HMF is fed to the continuous flow reactor, in one variation, the embodiment further comprises (i) maintaining catalyst selectivity of at least about 90%, 95%, or 99% over such time period or (ii) producing HTO in a yield of at least about 85%, 90%, 95%, or 99% over such period; or both (i) and (ii).

HTO in one aspect is formed from the consecutive conversion of HMF to BHMF to HTO with at least about 60% selectivity at each step in the conversion. In some embodiments, HTO is formed from the consecutive conversion of HMF to BHMF to HTO with at least about 70% selectivity at each step in the conversion. In some embodiments, HTO is formed from the consecutive conversion of HMF to BHMF to HTO with at least about 80% selectivity at each step in the conversion. In some embodiments, HTO is formed from the consecutive conversion of HMF to BHMF to HTO with at least about 90% selectivity at each step in the conversion. The consecutive conversion of HMF to BHMF to HTO is carried out in a continuous flow reactor by a heterogeneous reduction catalyst.

In one variation, HTO is produced with a conversion of at least 85% at each step of the consecutive conversion of HMF to BHMF to HTO. In some embodiments, HTO is produced with a conversion of at least 90% at each step of the consecutive conversion of HMF to BHMF to HTO. In some embodiments, HTO is produced with a conversion of at least 95% at each step of the consecutive conversion of HMF to BHMF to HTO. In some embodiments, HTO is produced with a conversion of at least 99% at each step of the consecutive conversion of HMF to BHMF to HTO.

In a particular variation, the consecutive conversion of HMF to BHMF to HTO is carried out in a continuous flow reactor by a heterogeneous reduction catalyst, forming HTO with at least about 60% or 65% or 70% or 75% or 80% or 85% or 90% or 95% selectivity and with a conversion of at least 60% or 65% or 70% or 75% or 80% or 85% or 90% or 95% at each step of the consecutive conversion of HMF to BHMF to HTO. In some variations, the consecutive conversion of HMF to BHMF to HTO is carried out on a commercial scale.

Also provided is a reactor effluent stream or reactor zone effluent stream comprising HTO produced by the consecutive conversion of HMF to BHMF to HTO, as detailed herein. In a particular aspect, the reactor effluent stream or reactor zone effluent stream comprising HTO contains no more than 10 weight % or 5 weight % or is substantially free of water. In another variation, the effluent stream comprising HTO further comprises water (e.g., when water is used as a solvent in the conversion of BHMF to HTO).

In one variation, the consecutive conversion of HMF to BHMF to HTO employs the use of a guard bed by feeding HMF through a guard bed comprising a transition metal to a continuous flow reactor. Alternatively or in addition, in another variation, the consecutive conversion of HMF to BHMF to HTO employs HMF as a feedstock at about or greater than about any of 5, 6, 10, 12 or 15 weight percent or more.

Liquid Phase Production of HDO (5) from HTO (4)

Aqueous solvents, organic solvents, and mixtures thereof are useful in the conversion of HTO (4) to HDO (5). In some variations, the solvent is an aqueous solvent. In some variations, the solvent is an organic solvent. In some variations the solvent is 100% water. In some variations, the solvent is a mixture of water and organic solvent. Suitable solvents include water, alcohols, esters, ethers, ketones, and mixtures thereof. Exemplary alcohols include ethanol, n-propanol, isopropanol, n-butanol, t-butanol, iso-butanol and sec-butanol. Exemplary esters include methyl acetate, ethyl acetate, propyl acetate and butyl acetate. Exemplary ethers include dioxane, dioxolane, glyme, diglyme, triglyme and tetraglyme. In one embodiment, the solvent is an organic solvent that contains less than about 25 weight % water. In another embodiment, the organic solvent contains less than about 10 weight % water. In another embodiment, the organic solvent contains less than about 5 weight % water. In another embodiment, the organic solvent is substantially free of water. In another embodiment, the organic solvent contains water. In one embodiment, an organic solvent contains up to about 50 weight % water. In another embodiment an organic solvent contains up to about 25 weight % water or up to about 10 weight % water. In one embodiment, the organic solvent contains between about 5 and 25 weight % water, between about 15 and 25 weight % water, or between about 10 and 20 weight % water. In one embodiment, the organic solvent is an azeotropic mixture comprising water. In one embodiment, the organic solvent is dioxane that contains between about 10 and 20 weight % water. In one embodiment, the organic solvent is isopropanol that contains between about 10 and 20 weight % water. In one embodiment, the organic solvent is glyme that contains between about 10 and 20 weight % water. In one embodiment, the solvent is water.

The conversion of HTO (4) to HDO (5) may be carried out under conditions in which less than 50 weight % water is present. In one embodiment, the conversion of HTO to HDO is carried out under conditions in which less than 25 weight % water is present. In another embodiment, the conversion of HTO to HDO is carried out under conditions in which less than 20 weight % water is present. In another embodiment, the conversion of HTO to HDO is carried out under conditions in which less than 10 weight % water is present. In another embodiment, the conversion of HTO to HDO is carried out under conditions in which less than 5 weight % water is present.

Suitable heterogeneous reduction catalysts for the conversion of HTO (4) to HDO (5) include those that comprise Pt alone or in combinations with other metals and/or alloys. In some embodiments, the catalysts comprise Pt and at least one metal selected from the group consisting of Cu, Co, Mo, La, Sm, Y, W, and Re (M2). In other embodiments, one or more other d-block metals, one or more rare earth metals (e.g., lanthanides), and/or one or more main group metals (e.g., Al) are present in combination with the Pt and M2 combinations. Typically, the total weight of metal(s) is from about 0.1% to about 10%, or from 0.2% to 10%, or from about 0.2% to about 8%, or from about 0.2% to about 5%, of the total weight of the catalyst. In some embodiments the total weight of metal of the catalyst is less than about 4%.

The molar ratio of Pt (M1) to (M2) may vary, for example, from about 20:1 to about 1:10. In some embodiments, the M1:M2 molar ratio is in the range of from about 10:1 to about 1:5. In other embodiments, the ratio of M1:M2 is in the range of about 8:1 to about 1:2.

The heterogeneous reduction catalyst in one aspect is a supported heterogeneous catalyst, wherein the catalyst is on the surface of the support. Suitable catalyst supports include, for example, acidic ion-exchange resin, gamma alumina, fluorinated alumina, sulfate or tungstate promoted zirconia, titania, silica, silica promoted alumina, aluminum phosphate, tungsten oxide supported on silica-alumina, acidic clay, supported mineral acid, and zeolites. The support materials may be modified using methods known in the art such as heat treatment, acid treatment or by the introduction of a dopant (for example, metal-doped titanias, metal-doped zirconias (e.g., tungstated-zirconia), metal-doped cerias, and metal-modified niobias). In one embodiment, supports include zirconias, silicas, and zeolites. When a catalyst support is used, the metals may be deposited using procedures known in the art including, but not limited to incipient wetness, ion-exchange, deposition-precipitation, and vacuum impregnation. When two or more metals are deposited on the same support, they may be deposited sequentially or simultaneously. In various embodiments, following metal deposition, the catalyst is dried at a temperature in the range of about 20° C. to about 120° C. for a period of time ranging from at least about 1 hour to about 24 hours. In these and other embodiments, the catalyst is dried under sub-atmospheric pressure conditions. In various embodiments, the catalyst is reduced after drying (e.g., by flowing 5% $H_2$ in $N_2$ at a temperature of at least about 200° C. for a period of time (e.g., at least about 3 hours)). Still further, in these and other embodiments, the catalyst is calcined in air at a temperature of at least about 200° C. for a period of time of at least about 3 hours.

In one embodiment, the temperature range for the reaction of HTO with hydrogen is about 80° C. to about 200° C. In another embodiment, the reaction temperature is about 120° C. to about 180° C. In one embodiment, the hydrogen pressure for the reaction of HTO with hydrogen is about 200 psi to about 2000 psi. In another embodiment, the hydrogen pressure is about 500 psi to about 2000 psi.

The conversion of HTO (4) to HDO (5) may yield a mixture of products. For example, the reaction product mixture may include not only 1, 6-hexanediol and/or 1,2,6-hexanetriol, but also lesser amounts of 1,5-hexanediol; 1,2-hexanediol; 1-hexanol; and 2-hexanol. In some embodiments, at least 50%, at least 60%, or at least 70% of the product mixture is 1,2,6-hexanetriol. In some embodiments, the production of HDO is at least about 40%, at least about 50% or at least about 60%.

In some variations, the conversion of HTO (4) to HDO (5) is carried out on a commercial scale.

Also provided is a reactor effluent stream or reactor zone effluent stream comprising HDO produced by the method of converting HTO to HDO as detailed herein. In a particular aspect, the HTO used in the transformation to HDO is obtained from any the reactions detailed herein for producing HTO.

Continuous Conversion System

Provided herein is a continuous conversion system for producing a reaction product. The continuous conversion system may include two or more contained areas, in each of which a reactant can undergo a reduction reaction in the presence of hydrogen and a heterogeneous catalyst. The two or more contained areas may be contained within one or more continuous flow reactors. In some variations, the two or more contained areas are contained within a single continuous flow reactor. In other variations, the two or more contained areas are contained within two or more continuous flow reactors. In another variation, each of the two or more contained areas is contained within a separate continuous flow reactor. The two or more contained areas may be different reaction zones within one or more continuous flow reactors. In some variations, the continuous conversion system includes 2, 3, 4, 5, or 6 contained areas.

The two or more contained areas may be sequentially coupled such that reactant for each successive reduction reaction is the product of the previous reduction reaction. In some variations, the two or more contained areas are sequentially coupled such that the reactor effluent stream or reactor zone effluent stream from each contained area is fed into the next successive contained area without isolation or purification of reaction products from the reactor effluent stream or reactor zone effluent stream.

In some variations, each of the contained areas is suitable for reduction of a reactant in the presence of hydrogen and a heterogeneous reduction catalyst. In some variations, each of the contained areas is suitable for carrying out one or more of the conversion processes described herein. In some variations, each of the contained areas is suitable for carrying out one or more of the conversion processes described herein under reaction conditions described herein (e.g., pressure, temperature, flow rate, solvent). In one variation, the continuous conversion system includes a contained area suitable for conversion of HMF (1) to BHMF (2). In another variation, the continuous conversion system includes a contained area suitable for conversion of BHMF (2) to BHMTHF (3). In another variation, the continuous conversion system includes a contained area suitable for conversion of BHMTHF (3) to HTO (4). In another variation, the continuous conversion system includes a contained area suitable for conversion of BHMF (2) to HTO (4).

The continuous conversion system may include two or more contained areas suitable for carrying out two or more of the conversions described herein in sequence. In one variation, the continuous conversion system includes a first contained area suitable for conversion of HMF (1) to BHMF (2) and a second contained area suitable for conversion of BHMF (2) to BHMTHF (3). In another variation, the continuous conversion system includes a first contained area suitable for conversion of HMF (1) to BHMF (2), a second contained area suitable for conversion of BHMF (2) to BHMTHF (3), and a third contained area suitable for conversion of BHMTHF (3) to HTO (4). In another variation, the continuous conversion system includes a first contained area suitable for conversion of HMF (1) to BHMF (2) and a second contained area suitable for conversion of BHMF (2) to HTO (4). In another variation, the continuous conversion system includes a first contained area suitable for conversion of BHMF (2) to BHMTHF (3) and a second contained area suitable for conversion of BHMTHF (3) to HTO (4).

Each contained area may include any of the heterogeneous reduction catalysts described herein. In one embodiment, the continuous conversion system includes two contained areas, wherein the first contained area contains a heterogeneous reduction catalyst comprising Cu and the second contained area contains a heterogeneous reduction catalyst comprising Ni. In another embodiment, the continuous conversion system includes two contained areas, wherein the first contained area contains a heterogeneous reduction catalyst comprising Ni and the second contained area contains a heterogeneous reduction catalyst comprising Pt. In another embodiment, the continuous conversion system includes three contained areas, wherein the first contained area contains a heterogeneous reduction catalyst comprising Cu, the second contained area contains a heterogeneous reduction catalyst comprising Ni, and the third contained area contains a heterogeneous reduction catalyst comprising Pt. In some embodiments, the heterogeneous reduction catalyst comprising Cu exhibits at least about 85%, 90%, 95%, or 99% selectivity for converting a reactant to a product over an on-stream period of any one of 150, 300, 500, 1,000, 2,000, 3,000, 5,000, 8,000, or 10,000 hours. In some embodiments, the heterogeneous reduction catalyst comprising Ni exhibits at least about 85%, 90%, 95%, or 99% selectivity for converting a reactant to a product over an on-stream period of any one of 150, 300, 500, 1,000, 2,000, 3,000, 5,000, 8,000, or 10,000 hours. In some embodiments, the heterogeneous reduction catalyst comprising Pt exhibits at least about 85%, 90%, 95%, or 99% selectivity for converting a reactant to a product over an on-stream period of any one of 150, 300, 500, 1,000, 2,000, 3,000, 5,000, 8,000, or 10,000 hours.

The continuous conversion system may contain a guard bed comprising a transition metal, such as any of the guard beds described herein. In one variation, the guard bed is coupled to the first contained area such that the first reactant can be fed through the guard bed to the first contained area.

All variations of each of the processes and systems described herein may be configured for use on a commercial scale.

All variations of each of the processes and compositions described wherein, where applicable, may be combined as if each and every combination of variations were specifically and individually listed.

All patents, patent applications and non-patent literature cited herein are hereby incorporated herein by reference in their entireties.

ENUMERATED EMBODIMENTS

The following enumerated embodiments are representative of some aspects of the invention.

1. A process for preparing 2,5-bis-hydroxymethylfuran (BHMF) from 5-hydroxymethylfurfural (HMF) comprising:
feeding 5-hydroxymethylfurfural (HMF) to a continuous flow reactor for an on-stream period of at least 150 hours; and
reacting the 5-hydroxymethylfurfural (HMF) with hydrogen in the continuous flow reactor in the presence of an organic solvent and a heterogeneous reduction catalyst comprising at least one metal selected from the group consisting of Ni, Co, Cu, Ag, Pt, Pd, Fe and Ru or a combination thereof to form 2,5-bis-hydroxymethylfuran (BHMF) with at least about 90% selectivity and at least 85% 5-hydroxymethylfurfural (HMF) conversion.

2. The process of embodiment 1, wherein the 2,5-bis-hydroxymethylfuran (BHMF) is formed with at least about 90% selectivity and at least 90% 5-hydroxymethylfurfural (HMF) conversion.

3. The process of embodiment 1, wherein the 2,5-bis-hydroxymethylfuran (BHMF) is formed with at least about 95% selectivity and at least 90% 5-hydroxymethylfurfural (HMF) conversion.

4. The process of any one of embodiments 1-3, wherein the 2,5-bis-hydroxymethylfuran (BHMF) is formed over the on-stream period of at least 150 hours.

5. The process of any one of embodiments 1-4, wherein the organic solvent contains less than about 25 weight % water.

6. The process of any one of embodiments 1-4, wherein the organic solvent contains less than about 10 weight % water.

7. The process of any one of embodiments 1-4, wherein the organic solvent is substantially free of water.

8. The process of any one of embodiments 1-7, wherein the 5-hydroxymethylfurfural (HMF) is fed to the continuous flow reactor through a guard bed comprising a transition metal.

9. The process of embodiment 8, wherein the guard bed comprises at least one transition metal selected from the group consisting of Ag, Zn, Cu, Fe, Ni, Co and Pb or a salt or combination thereof.

10. The process of any one of embodiments 1-9, wherein the concentration of the 5-hydroxymethylfurfural (HMF) is greater than about 5 weight percent in the organic solvent.

11. The process of embodiment 10, wherein the concentration of the 5-hydroxymethylfurfural (HMF) is greater than about 10 weight percent in the organic solvent.

12. A process for preparing 2,5-bis-hydroxymethylfuran (BHMF) from 5-hydroxymethylfurfural (HMF) comprising:
feeding 5-hydroxymethylfurfural (HMF) through a guard bed comprising a transition metal to a continuous flow reactor; and
reacting the 5-hydroxymethylfurfural (HMF) with hydrogen in the continuous flow reactor in the presence of an organic solvent and a heterogeneous reduction catalyst comprising at least one metal selected from the group consisting of Ni, Co, Cu, Ag, Pd, Pt, Fe and Ru or a combination thereof to form 2,5-bis-hydroxymethylfuran (BHMF).

13. The process of embodiment 12, wherein the guard bed comprises at least one transition metal selected from the group consisting of Ag, Zn, Cu, Fe, Ni, Co and Pb or a salt or combination thereof.

14. The process of embodiment 13, wherein the guard bed comprises at least one transition metal selected from the group consisting of Ag, Zn, Cu and Pb or a salt or combination thereof.

15. The process of any one of embodiments 12-14, wherein the concentration of the 5-hydroxymethylfurfural (HMF) is greater than about 5 weight percent in the organic solvent.

16. The process of embodiment 15, wherein the concentration of the 5-hydroxymethylfurfural (HMF) is greater than about 10 weight percent in the organic solvent.

17. The process of any one of embodiments 12-16, wherein the 5-hydroxymethylfurfural (HMF) is fed to the continuous flow reactor for an on-stream period of at least 150 hours.

18. The process of embodiment 17, wherein 2,5-bis-hydroxymethylfuran (BHMF) is formed over an on-stream period of at least 150 hours.

19. A process for preparing 2,5-bis-hydroxymethylfuran (BHMF) from 5-hydroxymethylfurfural (HMF) comprising:
feeding 5-hydroxymethylfurfural (HMF) to a continuous flow reactor at a concentration of greater than or equal to 6 weight percent in an organic solvent for an on-stream period of at least 150 hours; and
reacting the 5-hydroxymethylfurfural (HMF) with hydrogen in the continuous flow reactor in the presence of the organic solvent and a heterogeneous reduction catalyst comprising at least one metal selected from the group consisting of Ni, Co, Cu, Ag, Pt, Pd, Fe and Ru or a combination thereof to form the 2,5-bis-hydroxymethylfuran (BHMF) over the on-stream period of at least 150 hours.

20. The process of embodiment 19, wherein the concentration of the 5-hydroxymethylfurfural (HMF) is greater than about 10 weight percent.

21. The process of embodiment 19 or 20, wherein the 5-hydroxymethylfurfural (HMF) is fed to the continuous flow reactor through a guard bed comprising a transition metal.

22. The process of embodiment 21, wherein the guard bed comprises at least one transition metal selected from the group consisting of Ag, Zn, Cu, Fe, Ni, Co and Pb or a salt or combination thereof.

23. The process of any one of embodiments 19-22, wherein the 2,5-bis-hydroxymethylfuran (BHMF) is formed with at least about 90% selectivity and at least 85% 5-hydroxymethylfurfural (HMF) conversion.

24. The process of any one of embodiments 19-22, wherein the 2,5-bis-hydroxymethylfuran (BHMF) is formed with at least about 95% selectivity and at least 90% 5-hydroxymethylfurfural (HMF) conversion.

25. The process of any one of embodiments 1-24, wherein the organic solvent is selected from the group consisting of alcohols, esters, ethers and mixtures thereof.

26. The process of embodiment 25, wherein the organic solvent is an alcohol.

27. The process of embodiment 26, wherein the alcohol is selected from the group consisting of ethanol, n-propanol, isopropanol, n-butanol, t-butanol, iso-butanol and sec-butanol.

28. The process of embodiment 25, wherein the organic solvent is an ester.

29. The process of embodiment 28, wherein the ester is selected from the group consisting of methyl acetate, ethyl acetate, propyl acetate and butyl acetate.

30. The process of embodiment 25, wherein the organic solvent is an ether.

31. The process of embodiment 30, wherein the ether is selected from the group consisting of dioxane, dioxolane, glyme, diglyme, triglyme and tetraglyme.

32. The process of any one of embodiments 1-31, wherein the heterogeneous reduction catalyst comprises a combination of metals selected from the group consisting of Co—Cu, Ni—Cu, Ag—Ni, Ag—Co and Ag—Ru.

33. The process of any one of embodiments 1-32, wherein the heterogeneous reduction catalyst further comprises a modifier.

34. The process of embodiment 33, wherein the modifier is selected from the group consisting of Au, W, Cu, Zn, Mo, Sb, Bi and Pb.

35. The process of any one of embodiments 1-34, wherein the heterogeneous reduction catalyst further comprises a catalyst support.

36. The process of embodiment 35, wherein the catalyst support is selected from the group consisting of carbons, aluminas, zirconias, silicas, alumina-silicas, titanias, alumina-titanias, silicon carbides and mixed phases thereof.

37. The process of any one of embodiments 1-36, wherein the 5-hydroxymethylfurfural (HMF) is reacted with hydrogen at a temperature in a range of about 50° C. to about 150° C. and at a pressure in a range of about 50 psi to about 2000 psi.

38. A process for preparing 2,5-bis-hydroxymethyltetrahydrofuran (BHMTHF) from 2,5-bis-hydroxymethylfuran (BHMF) comprising:

reacting 2,5-bis-hydroxymethylfuran (BHMF) obtained from the process of any one of claims 1-37 with hydrogen in a continuous flow reactor in the presence of an organic solvent and a heterogeneous reduction catalyst comprising at least one metal selected from the group consisting of Ni, Co, Cu, Ag, Pd, Pt and Ru or a combination thereof to form the 2,5-bis-hydroxymethyltetrahydrofuran (BHMTHF).

39. The process of embodiment 38, wherein the heterogeneous reduction catalyst used in the reaction of 2,5-bis-hydroxymethylfuran (BHMF) with hydrogen is the same as or different from the heterogeneous reduction catalyst used in the reaction of 5-hydroxymethylfurfural (HMF) with hydrogen.

40. The process of embodiment 38 or 39, wherein the temperature and pressure in the reaction of 2,5-bis-hydroxymethylfuran (BHMF) with hydrogen are the same as or different from the temperature and pressure in the reaction of 5-hydroxymethylfurfural (HMF) with hydrogen.

41. The process of any one of embodiments 38-40, wherein the reactor used in the reaction of 2,5-bis-hydroxymethylfuran (BHMF) with hydrogen is the same as or different from the reactor used in the reaction of 5-hydroxymethylfurfural (HMF) with hydrogen.

42. A process for preparing 1,2,6-hexanetriol (HTO) from 2,5-bis-hydroxymethyltetrahydrofuran (BHMTHF) comprising:

reacting 2,5-bis-hydroxymethyltetrahydrofuran (BHMTHF) obtained from the process of any one of claims 38-41 with hydrogen in a continuous flow reactor in the presence of an aqueous or organic solvent and a heterogeneous reduction catalyst comprising at least one metal selected from the group consisting of Ni, Co, Cu, Ag, Pt and Ru or a combination thereof to form the 1,2,6-hexanetriol (HTO).

43. The process of embodiment 42, wherein the heterogeneous reduction catalyst used in the reaction of 2,5-bis-hydroxymethyltetrahydrofuran (BHMTHF) with hydrogen is the same as or different from (i) the heterogeneous reduction catalyst used in the reaction of 5-hydroxymethylfurfural (HMF) with hydrogen or (ii) the heterogeneous reduction catalyst used in the reaction of 2,5-bis-hydroxymethylfuran (BHMF) with hydrogen.

44. The process of embodiment 42 or 43, wherein the temperature and pressure in the reaction of 2,5-bis-hydroxymethyltetrahydrofuran (BHMTHF) with hydrogen are the same as or different from (i) the temperature and pressure in the reaction of 5-hydroxymethylfurfural (HMF) with hydrogen or (ii) the temperature and pressure in the reaction of 2,5-bis-hydroxymethylfuran (BHMF) with hydrogen.

45. The process of any one of embodiments 42-44, wherein the reactor used in the reaction of 2,5-bis-hydroxymethyltetrahydrofuran (BHMTHF) with hydrogen is the same as or different from (i) the reactor used in the reaction of 5-hydroxymethylfurfural (HMF) with hydrogen or (ii) the reactor used in the reaction of 2,5-bis-hydroxymethylfuran (BHMF) with hydrogen.

46. A process for preparing 1,2,6-hexanetriol (HTO) from 2,5-bis-hydroxymethylfuran (BHMF) comprising:

reacting 2,5-bis-hydroxymethylfuran (BHMF) obtained from the process of any one of claims 1-37 with hydrogen in a continuous flow reactor in the presence of an aqueous or organic solvent and a heterogeneous reduction catalyst comprising at least one metal selected from the group consisting of Ni, Co, Cu, Ag, Pt, Pd and Ru or a combination thereof to form the 1,2,6-hexanetriol (HTO).

47. The process of embodiment 46, wherein the 2,5-bis-hydroxymethylfuran (BHMF) is reacted with hydrogen at a temperature in a range of about 80° C. to about 180° C. and a pressure in a range of about 50 psi to about 2000 psi.

48. The process of embodiment 46 or 47, wherein the heterogeneous reduction catalyst used in the reaction of 2,5-bis-hydroxymethylfuran (BHMF) with hydrogen is the same as or different from the heterogeneous reduction catalyst used in the reaction of 5-hydroxymethylfurfural (HMF) with hydrogen.

49. A process for preparing 1,6-hexanediol (HDO) from 1,2,6-hexanetriol (HTO) comprising:
reacting 1,2,6-hexanetriol (HTO) obtained from the process of any one of embodiments 42-48 with hydrogen in a continuous flow reactor in the presence of a heterogeneous reduction catalyst comprising at least one metal selected from the group consisting of Ni, Co, Cu, Ag, Pt and Ru or a combination thereof to form 1,6-hexanediol (HDO).

50. The process of embodiment 49, wherein the 1,2,6-hexanetriol (HTO) is reacted with hydrogen in a continuous flow reactor in the presence of an aqueous or organic solvent or a mixture thereof.

51. The process of embodiment 50, wherein the organic solvent is selected from the group consisting of alcohols, esters, ethers and mixtures thereof.

52. The process of any one of embodiments 49-51, wherein the heterogeneous reduction catalyst further comprises a modifier.

53. The process of embodiment 52, wherein the modifier is selected from the group consisting of Au, W, Cu, Zn, Mo, Sb, Bi and Pb.

54. The process of any one of embodiments 49-53, wherein the heterogeneous reduction catalyst further comprises a catalyst support.

55. The process of embodiment 54, wherein the catalyst support is selected from the group consisting of carbons, aluminas, zirconias, silicas, alumina-silicas, titanias, alumina-titanias, silicon carbides and mixed phases thereof.

56. The process of any one of embodiments 49-55, wherein 1,2,6-hexanetriol (HTO) is reacted with hydrogen at a temperature in a range of about 80° C. to about 200° C. and at a pressure in a range of about 50 psi to about 2000 psi.

57. A process for preparing 1,2,6-hexanetriol (HTO) from 5-hydroxymethylfurfural (HMF) comprising:
feeding 5-hydroxymethylfurfural (HMF) to a continuous flow reactor at a concentration of greater than about 5 weight percent in an organic solvent;
reacting the 5-hydroxymethylfurfural (HMF) with hydrogen in the continuous flow reactor in the presence of the organic solvent and a heterogeneous reduction catalyst comprising at least one metal selected from the group consisting of Ni, Co, Cu, Ag, Pt, Pd, Fe and Ru or a combination thereof to form 2,5-bis-hydroxymethylfuran (BHMF) in a first reactor effluent stream or a first reactor zone effluent stream;
reacting the 2,5-bis-hydroxymethylfuran (BHMF) with hydrogen, without isolation or purification of the 2,5-bis-hydroxymethylfuran (BHMF) from the first reactor effluent stream or the first reactor zone effluent stream, in the presence of a heterogeneous reduction catalyst to form 2,5-bis-hydroxymethyltetrahydrofuran (BHMTHF) in a second reactor effluent stream or a second reactor zone effluent stream; and
reacting the 2,5-bis-hydroxymethyltetrahydrofuran (BHMTHF) with hydrogen, without isolation or purification of the 2,5-bis-hydroxymethyltetrahydrofuran (BHMTHF) from the second reactor effluent stream or the second reactor zone effluent stream, in the presence of a heterogeneous reduction catalyst to form 1,2,6-hexanetriol (HTO).

58. The process of embodiment 57, wherein the reaction of 2,5-bis-hydroxymethyltetrahydrofuran (BHMTHF) with hydrogen is carried out in the presence of an aqueous solvent and a heterogeneous reduction catalyst to form 1,2,6-hexanetriol (HTO).

59. A process for preparing 1,2,6-hexanetriol (HTO) from 5-hydroxymethylfurfural (HMF) comprising:
feeding 5-hydroxymethylfurfural (HMF) to a continuous flow reactor at a concentration of greater than about 5 weight percent in an organic solvent;
reacting the 5-hydroxymethylfurfural (HMF) with hydrogen in the continuous flow reactor in the presence of the organic solvent and a heterogeneous reduction catalyst comprising at least one metal selected from the group consisting of Ni, Co, Cu, Ag, Pt, Pd, Fe and Ru or a combination thereof to form 2,5-bis-hydroxymethylfuran (BHMF) in a first reactor effluent stream or a first reactor zone effluent stream; and
reacting the 2,5-bis-hydroxymethylfuran (BHMF) with hydrogen, without isolation or purification of the 2,5-bis-hydroxymethylfuran (BHMF) from the first reactor effluent stream or a first reactor zone effluent stream, in the presence of a heterogeneous reduction catalyst to form 1,2,6-hexanetriol (HTO).

60. The process of embodiment 57 or 59, wherein the reaction of 2,5-bis-hydroxymethylfuran (BHMF) with hydrogen is carried out in the presence of an aqueous solvent and a heterogeneous reduction catalyst to form 1,2,6-hexanetriol (HTO).

61. A process for producing any one or more of HMDA, adipic acid, caprolactam, caprolactone, a polyol, a polyester polyol, a polyester and a polyurethane comprising converting the 1,6-hexanediol (HDO) produced by any one of embodiments 49 to 56 to the one or more of HMDA, adipic acid, caprolactam, caprolactone, a polyol, a polyester polyol, a polyester and a polyurethane.

62. A process for producing any one or more of a polyol, a polyester polyol, a polyester and a polyurethane comprising converting the 2,5-bis-hydroxymethylfuran (BHMF), 2,5-bis-hydroxymethyltetrahydrofuran (BHMTHF) or 1,2,6-hexanetriol (HTO) produced by the process of any one of embodiments 1-48 to the any one or more of a polyol, a polyester polyol, a polyester and a polyurethane.

63. The process of any one of embodiments 35, 36, 54 or 55, wherein the catalyst support is a shaped support.

64. The process of embodiment 63, wherein the shape of the catalyst support is selected from the group consisting of an extrudate, sphere, bead, cylinder, pellet, tablet, multilobed shape, ring, star, ripped cylinder, trihole, alpha and wheels.

65. The process of any one embodiments 1-64, wherein the heterogeneous reduction catalyst comprises at least one metal selected from the group consisting of Ag, Ru, Pd and Pt and total concentration of the metals is from at least 0.1 weight % to about 15 weight % of the total weight of the catalyst.

66. The process of any one of embodiments 1-64, wherein the heterogeneous reduction catalyst comprises at least one metal selected from the group consisting of Ni, Cu, Co and Fe and the total concentration of the metals is from at least 0.5 weight % to about 40 weight % of the total weight of the catalyst.

1A. A process for preparing 2,5-bis-hydroxymethylfuran (BHMF) from 5-hydroxymethylfurfural (HMF) comprising:
reacting the 5-hydroxymethylfurfural (HMF) with hydrogen in a continuous flow reactor in the presence of an organic solvent and a heterogeneous reduction catalyst comprising at least one metal selected from the group consisting of Ni, Co, Cu, Ag, Pt, Pd, Fe and Ru or a combination thereof to form the 2,5-bis-hydroxymethylfuran (BHMF), wherein the process further comprises one or more of (i)-(iii):

(i) forming the 2,5-bis-hydroxymethylfuran (BHMF) over an on-stream period of at least 150 hours;

(ii) feeding the 5-hydroxymethylfurfural (HMF) through a guard bed comprising a transition metal to the continuous flow reactor;

(iii) feeding the 5-hydroxymethylfurfural (HMF) to the continuous flow reactor for an on-stream period of at least 150 hours.

2A. The process of embodiment 1A, wherein the reaction proceeds with at least 85% conversion of the 5-hydroxymethylfurfural (HMF).

3A. The process of any one of embodiments 1A-2A, wherein the process comprises forming the 2,5-bis-hydroxymethylfuran (BHMF) with at least about 90% selectivity.

4A. The process of any one of embodiments 1A-3A, wherein (i) applies.

5A. The process of any one of embodiments 1A-4A, wherein (ii) applies.

6A. The process of embodiment 5A, wherein the guard bed comprises at least one transition metal selected from the group consisting of Ag, Zn, Cu, Fe, Ni, Co and Pb or a salt or combination thereof.

7A. The process of embodiment 6A, wherein the guard bed comprises at least one transition metal selected from the group consisting of Ag, Zn, Cu and Pb or a salt or combination thereof.

8A. The process of any one of embodiments 1A-7A, wherein (iii) applies.

9A. The process of any one of embodiments 1A-8A, wherein the process comprises feeding the 5-hydroxymethylfurfural (HMF) to the continuous flow reactor at a concentration of greater than about 6 weight percent in the organic solvent.

10A. The process of any one of embodiments 1A-9A, wherein the process comprises feeding the 5-hydroxymethylfurfural (HMF) to the continuous flow reactor at a concentration of greater than about 10 weight percent in the organic solvent.

11A. The process of any one of embodiments 1A-10A, wherein the process comprises forming the 2,5-bis-hydroxymethylfuran (BHMF) with at least about 90% selectivity and at least 90% 5-hydroxymethylfurfural (HMF) conversion.

12A. The process of any one of embodiments 1A-11A, wherein the process comprises forming the 2,5-bis-hydroxymethylfuran (BHMF) with at least about 95% selectivity and at least 90% 5-hydroxymethylfurfural (HMF) conversion.

13A. The process of any one of embodiments 1A-12A, wherein the organic solvent comprises less than about 25 weight % water.

14A. The process of any one of embodiments 1A-12A, wherein the organic solvent comprises less than about 10 weight % water.

15A. The process of any one of embodiments 1A-12A, wherein the organic solvent is substantially free of water.

16A. The process of any one of embodiments 1A-15A, wherein the organic solvent is selected from the group consisting of alcohols, esters, ethers and mixtures thereof.

17A. The process of embodiment 16A, wherein the organic solvent comprises an alcohol.

18A. The process of embodiment 17A, wherein the alcohol is selected from the group consisting of ethanol, n-propanol, isopropanol, n-butanol, t-butanol, iso-butanol and sec-butanol.

19A. The process of embodiment 16A, wherein the organic solvent comprises an ester.

20A. The process of embodiment 19A, wherein the ester is selected from the group consisting of methyl acetate, ethyl acetate, propyl acetate and butyl acetate.

21A. The process of embodiment 16A, wherein the organic solvent comprises an ether.

22A. The process of embodiment 21A, wherein the ether is selected from the group consisting of dioxane, dioxolane, glyme, diglyme, triglyme and tetraglyme.

23A. The process of any one of embodiments 1A-22A, wherein the heterogeneous reduction catalyst comprises a combination of metals selected from the group consisting of Co—Cu, Ni—Cu, Ag—Ni, Ag—Co and Ag—Ru.

24A. The process of any one of embodiments 1A-23A, wherein the heterogeneous reduction catalyst further comprises a modifier.

25A. The process of embodiment 24A, wherein the modifier is selected from the group consisting of Mn, Co, Au, W, Cu, Zn, Mo, Sb, Bi and Pb.

26A. The process of any one of embodiments 1A-25A, wherein the heterogeneous reduction catalyst further comprises a catalyst support.

27A. The process of embodiment 26A, wherein the catalyst support is selected from the group consisting of carbons, aluminas, zirconias, silicas, alumina-silicas, titanias, alumina-titanias, silicon carbides and mixed phases thereof.

28A. The process of any one of embodiments 1A-27A, wherein the 5-hydroxymethylfurfural (HMF) is reacted with hydrogen at a temperature in a range of about 50° C. to about 150° C. and at a pressure in a range of about 50 psi to about 2000 psi.

29A. The process of any one of embodiments 1A-28A, further comprising reacting the 2,5-bis-hydroxymethylfuran (BHMF) with hydrogen in a continuous flow reactor in the presence of an organic solvent and a heterogeneous reduction catalyst comprising at least one metal selected from the group consisting of Ni, Co, Cu, Ag, Pd, Pt and Ru or a combination thereof to form 2,5-bis-hydroxymethyltetrahydrofuran (BHMTHF).

30A. The process of embodiment 29A, wherein the heterogeneous reduction catalyst used in the reaction of the 2,5-bis-hydroxymethylfuran (BHMF) with hydrogen is the same as the heterogeneous reduction catalyst used in the reaction of the 5-hydroxymethylfurfural (HMF) with hydrogen.

31A. The process of embodiment 29A, wherein the heterogeneous reduction catalyst used in the reaction of the 2,5-bis-hydroxymethylfuran (BHMF) with hydrogen is different from the heterogeneous reduction catalyst used in the reaction of the 5-hydroxymethylfurfural (HMF) with hydrogen.

32A. The process of any one of embodiments 29A-31A, wherein the temperature and pressure in the reaction of the 2,5-bis-hydroxymethylfuran (BHMF) with hydrogen are the same as the temperature and pressure in the reaction of the 5-hydroxymethylfurfural (HMF) with hydrogen.

33A. The process of any one of embodiments 29A-31A, wherein the temperature and pressure in the reaction of the 2,5-bis-hydroxymethylfuran (BHMF) with hydrogen are different from the temperature and pressure in the reaction of the 5-hydroxymethylfurfural (HMF) with hydrogen.

34A. The process of any one of embodiments 29A-33A, wherein the continuous flow reactor used in the reaction of the 2,5-bis-hydroxymethylfuran (BHMF) with hydrogen is the same as the continuous flow reactor used in the reaction of the 5-hydroxymethylfurfural (HMF) with hydrogen.

35A. The process of any one of embodiments 29A-33A, wherein the continuous flow reactor used in the reaction of the 2,5-bis-hydroxymethylfuran (BHMF) with hydrogen is different from the continuous flow reactor used in the reaction of the 5-hydroxymethylfurfural (HMF) with hydrogen.

36A. The process of any one of embodiments 29A-35A, wherein the organic solvent used in the reaction of the 2,5-bis-hydroxymethylfuran (BHMF) with hydrogen comprises less than about 25 weight % water.

37A. The process of any one of embodiments 29A-36A, further comprising reacting the 2,5-bis-hydroxymethyltetrahydrofuran (BHMTHF) with hydrogen in a continuous flow reactor in the presence of an aqueous or organic solvent and a heterogeneous reduction catalyst comprising at least one metal selected from the group consisting of Ni, Co, Cu, Ag, Pt and Ru or a combination thereof to form 1,2,6-hexanetriol (HTO).

38A. The process of embodiment 37A, wherein the heterogeneous reduction catalyst used in the reaction of the 2,5-bis-hydroxymethyltetrahydrofuran (BHMTHF) with hydrogen is the same as (i) the heterogeneous reduction catalyst used in the reaction of the 5-hydroxymethylfurfural (HMF) with hydrogen or (ii) the heterogeneous reduction catalyst used in the reaction of the 2,5-bis-hydroxymethylfuran (BHMF) with hydrogen.

39A. The process of embodiment 37A, wherein the heterogeneous reduction catalyst used in the reaction of the 2,5-bis-hydroxymethyltetrahydrofuran (BHMTHF) with hydrogen is different from (i) the heterogeneous reduction catalyst used in the reaction of the 5-hydroxymethylfurfural (HMF) with hydrogen or (ii) the heterogeneous reduction catalyst used in the reaction of the 2,5-bis-hydroxymethylfuran (BHMF) with hydrogen.

40A. The process of any one of embodiments 37A-39A, wherein the temperature and pressure in the reaction of the 2,5-bis-hydroxymethyltetrahydrofuran (BHMTHF) with hydrogen are the same as (i) the temperature and pressure in the reaction of the 5-hydroxymethylfurfural (HMF) with hydrogen or (ii) the temperature and pressure in the reaction of the 2,5-bis-hydroxymethylfuran (BHMF) with hydrogen.

41A. The process of any one of embodiments 37A-39A, wherein the temperature and pressure in the reaction of the 2,5-bis-hydroxymethyltetrahydrofuran (BHMTHF) with hydrogen are different from (i) the temperature and pressure in the reaction of the 5-hydroxymethylfurfural (HMF) with hydrogen or (ii) the temperature and pressure in the reaction of the 2,5-bis-hydroxymethylfuran (BHMF) with hydrogen.

42A. The process of any one of embodiments 37A-41A, wherein the continuous flow reactor used in the reaction of the 2,5-bis-hydroxymethyltetrahydrofuran (BHMTHF) with hydrogen is the same as (i) the continuous flow reactor used in the reaction of the 5-hydroxymethylfurfural (HMF) with hydrogen or (ii) the continuous flow reactor used in the reaction of the 2,5-bis-hydroxymethylfuran (BHMF) with hydrogen.

43A. The process of any one of embodiments 37A-41A, wherein the continuous flow reactor used in the reaction of the 2,5-bis-hydroxymethyltetrahydrofuran (BHMTHF) with hydrogen is different from (i) the continuous flow reactor used in the reaction of the 5-hydroxymethylfurfural (HMF) with hydrogen or (ii) the continuous flow reactor used in the reaction of the 2,5-bis-hydroxymethylfuran (BHMF) with hydrogen.

44A. The process of any one of embodiments 37A-43A, wherein the 2,5-bis-hydroxymethyltetrahydrofuran (BHMTHF) is reacted with hydrogen in the presence of an organic solvent comprising less than about 25 weight % water.

45A. The process of any one of embodiments 1A-28A, further comprising reacting the 2,5-bis-hydroxymethylfuran (BHMF) with hydrogen in a continuous flow reactor at a pressure in a range of about 50 psi to about 2000 psi in the presence of an aqueous or organic solvent and a heterogeneous reduction catalyst comprising at least one metal selected from the group consisting of Ni, Co, Cu, Ag, Pt, Pd and Ru or a combination thereof to form 1,2,6-hexanetriol (HTO).

46A. The process of embodiment 45A, wherein the 2,5-bis-hydroxymethylfuran (BHMF) is reacted with hydrogen at a temperature in a range of about 80° C. to about 180° C.

47A. The process of embodiment 45A or 46A, wherein the heterogeneous reduction catalyst used in the reaction of the 2,5-bis-hydroxymethylfuran (BHMF) with hydrogen is the same as the heterogeneous reduction catalyst used in the reaction of the 5-hydroxymethylfurfural (HMF) with hydrogen.

48A. The process of embodiment 45A or 46A, wherein the heterogeneous reduction catalyst used in the reaction of the 2,5-bis-hydroxymethylfuran (BHMF) with hydrogen is different from the heterogeneous reduction catalyst used in the reaction of the 5-hydroxymethylfurfural (HMF) with hydrogen.

49A. The process of any one of embodiments 45A-48A, wherein the 2,5-bis-hydroxymethylfuran (BHMF) is reacted with hydrogen in the presence of an organic solvent comprising less than about 25 weight % water.

50A. The process of any one of embodiments 37A-49A, further comprising reacting the 1,2,6-hexanetriol (HTO) with hydrogen in a continuous flow reactor in the presence of a heterogeneous reduction catalyst comprising at least one metal selected from the group consisting of Ni, Co, Cu, Ag, Pt and Ru or a combination thereof to form 1,6-hexanediol (HDO).

51A. The process of embodiment 50A, wherein the 1,2,6-hexanetriol (HTO) is reacted with hydrogen in a continuous flow reactor in the presence of an aqueous or organic solvent or a mixture thereof.

52A. The process of embodiment 50A, wherein the wherein the 1,2,6-hexanetriol (HTO) is reacted with hydrogen in a continuous flow reactor in the presence of an organic solvent comprising less than about 25 weight % water.

53A. The process of embodiment 52A, wherein the organic solvent used in the reaction of the 1,2,6-hexanetriol (HTO) with hydrogen is selected from the group consisting of alcohols, esters, ethers and mixtures thereof.

54A. The process of any one of embodiments 50A-53A, wherein the heterogeneous reduction catalyst used in the reaction of the 1,2,6-hexanetriol (HTO) with hydrogen further comprises a modifier.

55A. The process of embodiment 54A, wherein the modifier used in the reaction of the 1,2,6-hexanetriol (HTO) with hydrogen is selected from the group consisting of Mn, Co, Au, W, Cu, Zn, Mo, Sb, Bi and Pb.

56A. The process of any one of embodiments 50A-55A, wherein the heterogeneous reduction catalyst used in the reaction of the 1,2,6-hexanetriol (HTO) with hydrogen further comprises a catalyst support.

57A. The process of embodiment 56A, wherein the catalyst support used in the reaction of the 1,2,6-hexanetriol (HTO) with hydrogen is selected from the group consisting of carbons, aluminas, zirconias, silicas, alumina-silicas, titanias, alumina-titanias, silicon carbides and mixed phases thereof.

58A. The process of any one of embodiments 50A-57A, wherein the 1,2,6-hexanetriol (HTO) is reacted with hydrogen at a temperature in a range of about 80° C. to about 200° C. and at a pressure in a range of about 50 psi to about 2000 psi.

59A. A process for preparing 1,2,6-hexanetriol (HTO) from 5-hydroxymethylfurfural (HMF) comprising:

(a) feeding 5-hydroxymethylfurfural (HMF) to a continuous flow reactor at a concentration of greater than about 5 weight percent in a first organic solvent;

(b) reacting the 5-hydroxymethylfurfural (HMF) with hydrogen in the continuous flow reactor in the presence of the first organic solvent and a first heterogeneous reduction catalyst comprising at least one metal selected from the group consisting of Ni, Co, Cu, Ag, Pt, Pd, Fe and Ru or a combination thereof to form 2,5-bis-hydroxymethylfuran (BHMF) in a first reactor effluent stream or a first reactor zone effluent stream;

(c) reacting the 2,5-bis-hydroxymethylfuran (BHMF) with hydrogen, without isolation or purification of the 2,5-bis-hydroxymethylfuran (BHMF) from the first reactor effluent stream or the first reactor zone effluent stream, in the presence of a second heterogeneous reduction catalyst to form 2,5-bis-hydroxymethyltetrahydrofuran (BHMTHF) in a second reactor effluent stream or a second reactor zone effluent stream; and (d) reacting the 2,5-bis-hydroxymethyltetrahydrofuran (BHMTHF) with hydrogen, without isolation or purification of the 2,5-bis-hydroxymethyltetrahydrofuran (BHMTHF) from the second reactor effluent stream or the second reactor zone effluent stream, in the presence of a third heterogeneous reduction catalyst to form the 1,2,6-hexanetriol (HTO).

60A. The process of embodiment 59A, wherein the first organic solvent comprises less than about 25 weight % water.

61A. The process of any one of embodiments 59A-60A, wherein the 2,5-bis-hydroxymethylfuran (BHMF) is reacted with hydrogen in the presence of a second organic solvent comprising less than about 25 weight % water.

62A. The process of any one of embodiments 59A-61A, wherein the 2,5-bis-hydroxymethyltetrahydrofuran (BHMTHF) is reacted with hydrogen in the presence of a third organic solvent comprising less than about 25 weight % water.

63A. The process of any one of embodiments 59A-62A, wherein the 2,5-bis-hydroxymethyltetrahydrofuran (BHMTHF) is reacted with hydrogen in the presence of an aqueous solvent.

64A. A process for preparing 1,2,6-hexanetriol (HTO) from 5-hydroxymethylfurfural (HMF) comprising:

feeding the 5-hydroxymethylfurfural (HMF) to a continuous flow reactor at a concentration of greater than about 5 weight percent in a first organic solvent;

reacting the 5-hydroxymethylfurfural (HMF) with hydrogen in the continuous flow reactor in the presence of the first organic solvent and a first heterogeneous reduction catalyst comprising at least one metal selected from the group consisting of Ni, Co, Cu, Ag, Pt, Pd, Fe and Ru or a combination thereof to form 2,5-bis-hydroxymethylfuran (BHMF) in a first reactor effluent stream or a first reactor zone effluent stream; and reacting the 2,5-bis-hydroxymethylfuran (BHMF) with hydrogen, without isolation or purification of the 2,5-bis-hydroxymethylfuran (BHMF) from the first reactor effluent stream or the first reactor zone effluent stream, in the presence of a second heterogeneous reduction catalyst to form the 1,2,6-hexanetriol (HTO).

65A. The process of embodiment 64A, wherein the organic solvent comprises less than about 25 weight % water.

66A. The process of any one of embodiments 64A-65A, wherein the 2,5-bis-hydroxymethylfuran (BHMF) is reacted with hydrogen in the presence of a second organic solvent comprising less than about 25 weight % water.

67A. The process of any one of embodiments 64A-65A, wherein the 2,5-bis-hydroxymethylfuran (BHMF) is reacted with hydrogen in the presence of an aqueous solvent.

68A. The process of any one of embodiments 50A-58A, further comprising converting the 1,6-hexanediol (HDO) to one or more of HMDA, adipic acid, caprolactam, caprolactone, a polyol, a polyester polyol, a polyester and a polyurethane.

69A. The process of any one of embodiments 1A-49A, further comprising converting the 2,5-bis-hydroxymethylfuran (BHMF), the 2,5-bis-hydroxymethyltetrahydrofuran (BHMTHF) or the 1,2,6-hexanetriol (HTO) to any one or more of a polyol, a polyester polyol, a polyester and a polyurethane.

70A. The process of any one of embodiments 26A, 27A, 56A, and 57A, wherein the catalyst support is a shaped support.

71A. The process of embodiment 70A, wherein the shape of the catalyst support is selected from the group consisting of an extrudate, sphere, bead, cylinder, pellet, tablet, multi-lobed shape, ring, star, ripped cylinder, trihole, alpha and wheels.

72A. The process of any one embodiments 1A-71A, wherein at least one of the heterogeneous reduction catalysts comprises at least one metal selected from the group consisting of Ag, Ru, Pd and Pt, and the total concentration of the metals is from at least 0.1 weight % to about 15 weight % of the total weight of the catalyst.

73A. The process of any one of embodiments 1A-71A, wherein at least one of the heterogeneous reduction catalysts comprises at least one metal selected from the group consisting of Ni, Cu, Co and Fe, and the total concentration of the metals is from at least 0.5 weight % to about 40 weight % of the total weight of the catalyst.

74A. A process for preparing 2,5-bis-hydroxymethyltetrahydrofuran (BHMTHF) from 2,5-bis-hydroxymethylfuran (BHMF) comprising:

reacting the 2,5-bis-hydroxymethylfuran (BHMF) with hydrogen in a continuous flow reactor at a pressure in a range of about 50 psi to about 2000 psi in the presence of:

(i) an organic solvent comprising less than about 25 weight % water, and (ii) a heterogeneous reduction catalyst comprising at least one metal selected from the group consisting of Ni, Co, Cu, Ag, Pd, Pt and Ru or a combination thereof to form the 2,5-bis-hydroxymethyltetrahydrofuran (BHMTHF).

75A. A process for preparing 1,2,6-hexanetriol (HTO) and 1,6-hexanediol (HDO) from 2,5-bis-hydroxymethyltetrahydrofuran (BHMTHF) comprising:

reacting the 2,5-bis-hydroxymethyltetrahydrofuran (BHMTHF) with hydrogen in a continuous flow reactor at a pressure in a range of about 50 psi to about 2000 psi in the presence of:
(i) an organic solvent comprising less than about 25 weight % water, and
(ii) a heterogeneous reduction catalyst comprising at least one metal selected from the group consisting of Ni, Co, Cu, Ag, Pt and Ru or a combination thereof
to form the 1,2,6-hexanetriol (HTO) and the 1,6-hexanediol (HDO) with at least about 90% combined selectivity and at least 85% 2,5-bis-hydroxymethyltetrahydrofuran (BHMTHF) conversion.

76A. A process for preparing 2,5-bis-hydroxymethylfuran (BHMF) from 5-hydroxymethylfurfural (HMF) comprising:
reacting the 5-hydroxymethylfurfural (HMF) with hydrogen in a continuous flow reactor at a pressure in a range of about 50 psi to about 2000 psi in the presence of
(i) an organic solvent comprising less than about 25 weight % water, and
(ii) a heterogeneous reduction catalyst comprising Cu
to form the 2,5-bis-hydroxymethylfuran (BHMF) with at least about 90% selectivity and at least 85% 5-hydroxymethylfurfural (HMF) conversion.

77A. The process of embodiment 76A, wherein the organic solvent comprises dioxane.

78A. The process of embodiment 76A, wherein the organic solvent comprises isopropanol.

79A. The process of embodiment 76A, wherein the organic solvent comprises glyme.

80A. The process of any one of embodiments 76A-79A, wherein the organic solvent comprises from about 5 weight % to about 20 weight % water.

81A. The process of any one of embodiments 76A-80A, wherein the heterogeneous reduction catalyst further comprises an alumina catalyst support.

82A. A process for preparing 1,2,6-hexanetriol (HTO) from 5-hydroxymethylfurfural (HMF) comprising:
(a) reacting the 5-hydroxymethylfurfural (HMF) with hydrogen in a continuous flow reactor in the presence of
(i) a first organic solvent comprising less than about 25 weight % water, and
(ii) a first heterogeneous reduction catalyst comprising Cu
to form 2,5-bis-hydroxymethylfuran (BHMF);
(b) reacting the 2,5-bis-hydroxymethylfuran (BHMF) with hydrogen in the presence of
(i) a second organic solvent comprising less than about 25 weight % water, and
(ii) a second heterogeneous reduction catalyst comprising Ni to form 2,5-bis-hydroxymethyltetrahydrofuran (BHMTHF); and
(c) reacting the 2,5-bis-hydroxymethyltetrahydrofuran (BHMTHF) with hydrogen in the presence of
i) a third organic solvent comprising less than about 25 weight % water, and
(ii) a third heterogeneous reduction catalyst comprising Pt
to form the 1,2,6-hexanetriol (HTO).

83A. The process of embodiment 82A, wherein the 2,5-bis-hydroxymethylfuran (BHMF) is formed in a first reactor effluent stream or a first reactor zone effluent stream and is reacted with hydrogen without isolation or purification of the 2,5-bis-hydroxymethylfuran (BHMF) from the first reactor effluent stream or the first reactor zone effluent stream.

84A. The process of any one of embodiments 82A-83A, wherein the 2,5-bis-hydroxymethyltetrahydrofuran (BHMTHF) is formed in a second reactor effluent stream or a second reactor zone effluent stream and is reacted with hydrogen without isolation or purification of the 2,5-bis-hydroxymethyltetrahydrofuran (BHMTHF) from the second reactor effluent stream or the second reactor zone effluent stream.

85A. The process of any one of embodiments 82A-84A, wherein one or more of the first, second, and third organic solvents comprises dioxane.

86A. The process of embodiment 85A, wherein each of the first, second, and third organic solvents comprises dioxane.

87A. The process of claim any one of embodiments 82A-84A, wherein one or more of the first, second, and third organic solvents comprises isopropanol.

88A. The process of embodiment 87A, wherein each of the first, second, and third organic solvents comprises isopropanol.

89A. The process of embodiment 82A, wherein one or more of the first, second, and third organic solvents comprises glyme.

90A. The process of embodiment 89A, wherein each of the first, second, and third organic solvents comprises glyme.

91A. The process of any one of embodiments 82A-90A, wherein the third heterogeneous reduction catalyst further comprises tungsten.

92A. A process for preparing 1,6-hexanediol (HDO) from 5-hydroxymethylfurfural (HMF) comprising:
(a) reacting the 5-hydroxymethylfurfural (HMF) with hydrogen in a continuous flow reactor in the presence of
(i) a first organic solvent comprising less than about 25 weight % water, and
(ii) a first heterogeneous reduction catalyst comprising at least one metal selected from the group consisting of Co, Mn, Ni, and Cu or a combination thereof
to form 2,5-bis-hydroxymethyltetrahydrofuran (BHMTHF);
(b) reacting the 2,5-bis-hydroxymethyltetrahydrofuran (BHMTHF) with hydrogen in a continuous flow reactor the presence of
(i) a second organic solvent comprising less than about 25 weight % water, and
(ii) a second heterogeneous reduction catalyst comprising Pt
to form the 1,6-hexanetriol (HDO).

93A. The process of embodiment 92A, wherein the second heterogeneous reduction catalyst further comprises tungsten.

94A. The process of embodiment 92A or 93A, wherein the reaction of step (a) occurs within a first reaction zone and the reaction of step (b) occurs within a second reaction zone, wherein the first and second reaction zones are contained within the same continuous flow reactor.

95A. The process of embodiment 92A or 93A, wherein the reaction of step (a) occurs within a first continuous flow reactor, and the reaction of step (b) occurs within a second continuous flow reactor.

96A. The process of any one of embodiments 92A-95A, wherein the reaction of step (a) comprises formation of 2,5-bis-hydroxymethylfuran (BHMF), and at least a portion of the 2,5-bis-hydroxymethylfuran (BHMF) is reacted with hydrogen in the continuous flow reactor to form 2,5-bis-hydroxymethyltetrahydrofuran (BHMTHF).

97A. The process of any one of embodiments 92A-96A, wherein the reaction of step (b) comprises formation of 1,2,6-hexanetriol (HTO), and at least a portion of the 1,2,6-hexanetriol (HTO) is reacted with hydrogen in the continuous flow reactor to form 1,6-hexanediol (HDO).

98A. The process of any one of embodiments 92A-97A, wherein one or both of the first and second organic solvents comprises dioxane.

99A. The process of any one of embodiments 92A-97A, wherein one or both of the first and second organic solvents comprises isopropanol.

100A. The process of any one of embodiments 92A-97A, wherein one or both of the first and second organic solvents comprises glyme.

101A. The process of any one of embodiments 92A-100A, wherein the temperature in the reaction of step (b) is higher than the temperature in the reaction of step (a).

102A. The process of any one of embodiments 92A-101A, wherein the pressure in the reaction of step (b) is higher than the pressure in the reaction of step (a).

103A. A continuous conversion system for producing a reduction product, wherein the continuous conversion system comprises:

(i) a first contained area for the reduction of a first reactant in the presence of hydrogen and a heterogeneous reduction catalyst comprising Cu;

(ii) a second contained area for the reduction of a second reactant in the presence of hydrogen and a heterogeneous reduction catalyst comprising Ni; and (iii) a third contained area for the reduction of a third reactant in the presence of hydrogen and a heterogeneous reduction catalyst comprising Pt;

wherein the contained areas are sequentially coupled such that the second reactant comprises the product of the first reduction reaction and the third reactant comprises the product of the second reduction reaction.

104A. The continuous conversion system of embodiment 103A, wherein the first and second contained areas are contained within a single continuous flow reactor.

105A. The continuous conversion system of embodiment 103A or 104A, wherein the second and third contained areas are contained within a single continuous flow reactor.

106A. The continuous conversion system of any one of embodiments 103A-105A, wherein the reduction product comprises 1,2,6-hexanetriol (HTO).

107A. The continuous conversion system of any one of embodiments 103A-106A, wherein the first reactant comprises 5-hydroxymethylfurfural (HMF), the second reactant comprises 2,5-bis-hydroxymethylfuran (BHMF), and the third reactant comprises 2,5-bis-hydroxymethyltetrahydrofuran (BHMTHF).

108A. The continuous conversion system of any one of embodiments 103A-106A, further comprising a guard bed comprising a transition metal.

109A. The continuous conversion system of embodiment 108A, wherein the guard bed is coupled to the first contained area such that the first reactant can be fed through the guard bed to the first contained area.

EXAMPLES

Abbreviations

BET: Brunauer-Emmett-Teller method of determining surface area of materials, such as catalyst support Example 1. Conversion of HMF (1) to BHMF (2) in a Fixed Bed Reactor Preparation of 1 wt. % Pt; 0.02 wt. % Au on $Al_2O_3$ catalyst. Solutions containing $K_2Pt(OH)_6$ were prepared by the reaction of $Pt(OH)_2$ (Alfa) and KOH (Fisher). Solutions containing $KAuO_2$ were prepared by dissolving $Au(OH)_3$ (Alfa) in KOH solution at 70° C. for 3 hours with vigorous stirring. The $Al_2O_3$ support (BET surface area=30 m²/g) was obtained from Saint Gobain. 0.8 mL of $K_2Pt(OH)_6$ solution (122 mg Pt/mL) was mixed with 0.02 mL of $KAuO_2$ (102 mg Au/mL). The resultant mixture was diluted with 4 mL deionized water and added to 10 g of the $Al_2O_3$ support. The resultant material was dried at 120° C. for 15 minutes and then reduced at 250° C. with forming gas (5% $H_2$ in $N_2$) for 3 hours. The resultant catalyst was washed 5 times with 20 mL of deionized water and dried at 40° C. overnight.

1 g of the catalyst (1 g, 150-300 micron fraction) was placed into a fixed bed reactor tube with an internal diameter of 4.5 mm. A solution of 0.4 M HMF in isopropanol (6.3 wt. %) was fed to the reactor at 110° C. under a partial pressure of hydrogen of 1000 psi at a flow rate of 100 µL/min Results of the fixed bed run are presented in FIG. 1.

Example 2. Conversion of HMF (1) to BHMF (2) in a Fixed Bed Reactor with a Guard Bed Preparation of 1 wt. % Co; 5 wt. % Cu on $ZrO_2$ catalyst. Cobalt nitrate and copper nitrate solutions were prepared by dissolving $Co(NO_3)_2 \cdot 6H_2O$ (Sigma-Aldrich) and $Cu(NO_3)_2 \cdot 3H_2O$ (Sigma-Aldrich) in deionized water. The $ZrO_2$ support (BET surface area=40 m²/g) was obtained from Saint Gobain. 0.45 mL of cobalt nitrate solution (237 mg Co/mL) was mixed with 2 mL of copper nitrate solution (266 mg Cu/mL) to give a Co:Cu weight ratio of 1:5. This mixture was diluted with 0.55 mL of deionized water and added to 10 g of the $ZrO_2$ support. The resultant material was dried at 120° C. for 2 hours and calcined at 350° C. for 3 hours in air. After the calcination step the catalyst was reduced under forming gas flow at 350° C. for 3 hours.

Preparation of 5.1 wt. % Ag on $ZrO_2$ guard bed. Silver acetate solution was prepared by dissolving anhydrous silver acetate (Alfa) in 5 M $NH_4OH$. The $ZrO_2$ support (BET surface area=40 m²/g) was obtained from Saint Gobain. 3 mL of the silver acetate solution (180 mg Ag/mL) was added to 10 g of the ZrO2 support. The resultant material was dried at 120° C. for 2 hours and calcined at 250° C. for 3 hours in air. After the calcination step the guard bed material was reduced under forming gas flow at 300° C. for 3 hours.

Figure 2:
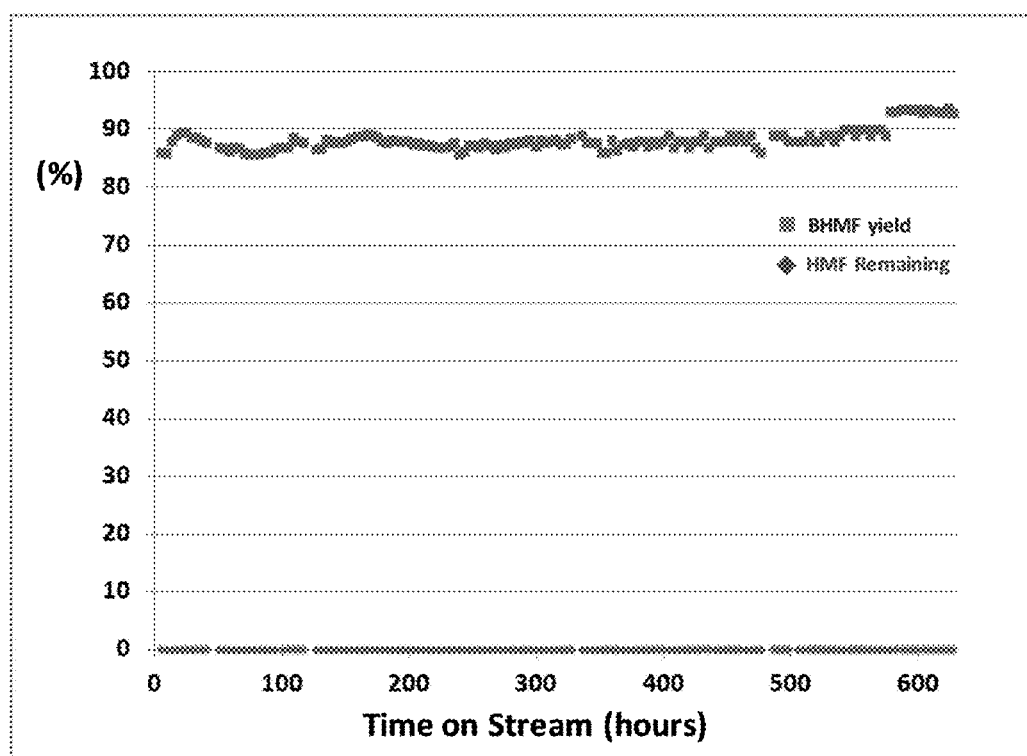
FIG. 2 depicts results (BHMF yield and HMF remaining as a function of time on-stream) for the conversion of HMF to BHMF in isopropanol in a fixed bed reactor with a guard bed (Ag on $ZrO_2$) using a Co—Cu catalyst on a $ZrO_2$ support, as described in Example 2.

1.35 g of the Co—Cu catalyst (150-300 micron fraction) was placed into a fixed bed reactor tube with an internal diameter of 4.5 mm. A guard bed reactor tube with an internal diameter of 4.5 mm was filled with 5 g of guard bed material (150-300 micron fraction) and placed in the front of catalyst bed reactor. A solution of 0.4 M HMF in isopropanol (6.3 wt. %) was fed to the guard bed at 30° C. and the reactor at 110° C. at a flow rate of 100 µL/min Both the guard bed and the reactor were under a partial pressure of hydrogen of 1000 psi. Results of the fixed bed run are presented in FIG. 2.

Comparative Example 3. Conversion of HMF (1) to BHMF (2) in a Fixed Bed Reactor without a Guard Bed Preparation of 1 wt. % Co, 5 wt. % Cu on ZrO2 catalyst. The catalyst was prepared according to the method described in Example 2.

Figure 3:
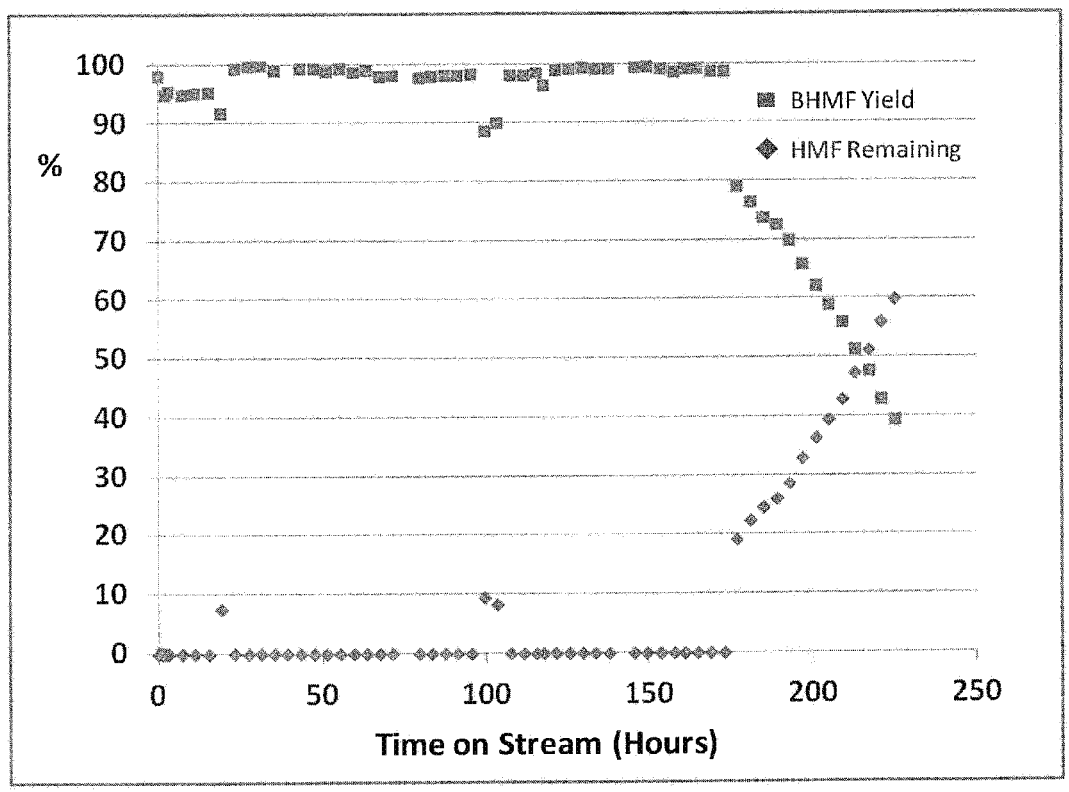
FIG. 3 depicts results (BHMF yield and HMF remaining as a function of time on-stream) for the conversion of HMF to BHMF in isopropanol in a fixed bed reactor without a guard bed using a Co—Cu catalyst on a $ZrO_2$ support, as described in Example 3.

1.35 g of the Co—Cu catalyst (150-300 micron fraction) was placed into a fixed bed reactor tube with an internal diameter of 4.5 mm. A solution of 0.4 M HMF in isopropanol (6.3 wt. %) was fed to the reactor at 110° C. under a partial pressure of hydrogen of 1000 psi at a flow rate of 100

μL/min. Results of the fixed bed run are presented in FIG. 3. After 170 hours on-stream the onset of catalyst deactivation was observed.

Comparative Example 4. Conversion of HMF (1) to BHMF (2) in a Fixed Bed Reactor Using Water as a Solvent Preparation of 1 wt. % Co; 5 wt. % Cu on $ZrO_2$ catalyst. The catalyst was prepared according to the method described in Example 2.

Figure 4:
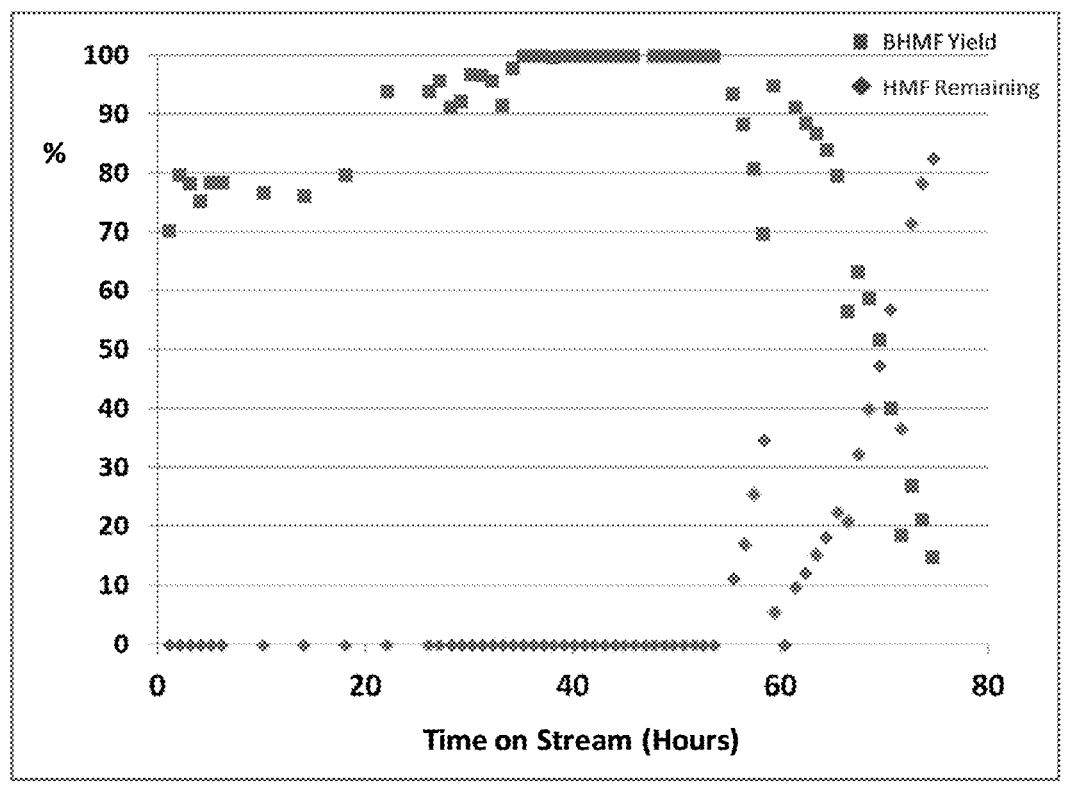
FIG. 4 depicts results (BHMF yield and HMF remaining as a function of time on-stream for the conversion of HMF to BHMF in water in a fixed bed reactor using a Co—Cu catalyst on a ZrO$_2$ support, as described in Example 4.

6 g of the Co—Cu catalyst (150-300 micron fraction) was placed into a fixed bed reactor tube with an internal diameter of 4.5 mm. A solution of 0.4 M HMF in water (5 wt. %) was fed to the reactor at 100° C. under a partial pressure of hydrogen of 1000 psi. The flow rate was varied between 150 μL/min and 400 μL/min during the course of the run. Results of the fixed bed run are presented in FIG. 4. At the onset of catalyst deactivation, the flow rate was reduced in an attempt to reach a stable condition. Catalyst deactivation continued to the point where no HMF conversion was observed.

Example 5. Conversion of HMF (1) to BHMF (2) in a Fixed Bed Reactor with a Guard Bed Preparation of 1 wt. % Pt, 0.02 wt. % Au on $Al_2O_3$ catalyst. The catalyst was prepared according to the method described in Example 1.

Preparation of 7.4 wt. % Cu on $ZrO_2$ guard bed. A copper nitrate solution was prepared by dissolving $Cu(NO_3)_2 \cdot 3H_2O$ (Sigma-Aldrich) in deionized water. The $ZrO_2$ support (BET surface area=40 $m^2/g$) was obtained from Saint Gobain. 3 mL of the copper nitrate solution (265 mg Cu/mL) was added to 10 g of the $ZrO_2$ support. The resultant material was dried at 120° C. for 2 hours, calcined in air at 350° C. for 3 hours and reduced under forming gas flow at 220° C. for 6 hours.

Figure 5:
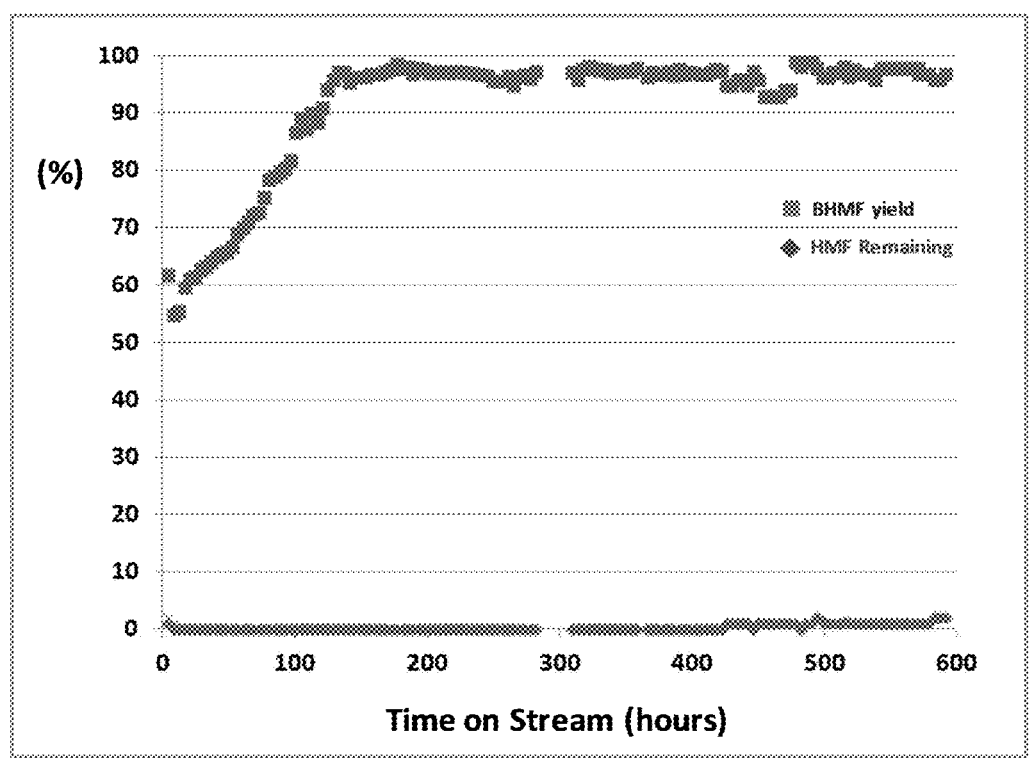
FIG. 5 depicts results (BHMF yield and HMF remaining as a function of time on-stream) for the conversion of HMF to BHMF in isopropanol in a fixed bed reactor with a guard bed (Cu on ZrO$_2$) using a Pt(Au) catalyst on a Al$_2$O$_3$ support, as described in Example 5.

The Pt—Au catalyst (2 g) was placed into a fixed bed reactor tube with an internal diameter of 4.5 mm. A guard bed reactor tube with an internal diameter of 4.5 mm was filled with 5 g of guard bed material (150-300 micron fraction) and this was placed in the front of catalyst bed reactor. A solution of 0.8 M HMF in isopropanol (12.5 wt. %) was fed to the guard bed at 100° C. and the reactor was held at 110° C. at a flow rate of 100 μL/min. Both the guard bed and the reactor were under a partial pressure of hydrogen of 1000 psi. Results of the fixed bed run are presented in FIG. 5.

Example 6. Conversion of HMF (1) to BHMF (2) in a Fixed Bed Reactor with a Guard Bed Preparation of 8.9 wt. % Ag on $Al_2O_3$ catalyst. The silver acetate solution was prepared by dissolving anhydrous silver acetate (Alfa) in 5 M $NH_4OH$. The $Al_2O_3$ support (BET surface area=260 $m^2/g$) was obtained from Saint Gobain. 2.87 mL of silver acetate solution (170 mg Ag/mL) was added to 5 g of the $Al_2O_3$ support. The resultant material was dried at 120° C. for 2 hours and calcined in air at 250° C. for 3 hours. The calcined material was reduced under forming gas flow at 300° C. for 3 hours.

Preparation of 7.0 wt. % Ag on $ZrO_2$ guard bed. The silver nitrate solution was prepared by dissolving silver nitrate (Alfa) in deionized water. The $ZrO_2$ support (BET surface area=40 $m^2/g$) was obtained from Saint Gobain. 1.48 mL of the silver nitrate solution (254 mg Ag/mL) was added to 5 g of the $ZrO_2$ support. The resultant material was dried at 120° C. for 2 hours and calcined at 400° C. for 3 hours in air. After the calcination step the guard bed material was reduced under nitrogen gas flow at 300° C. for 4 hours.

Figure 6:
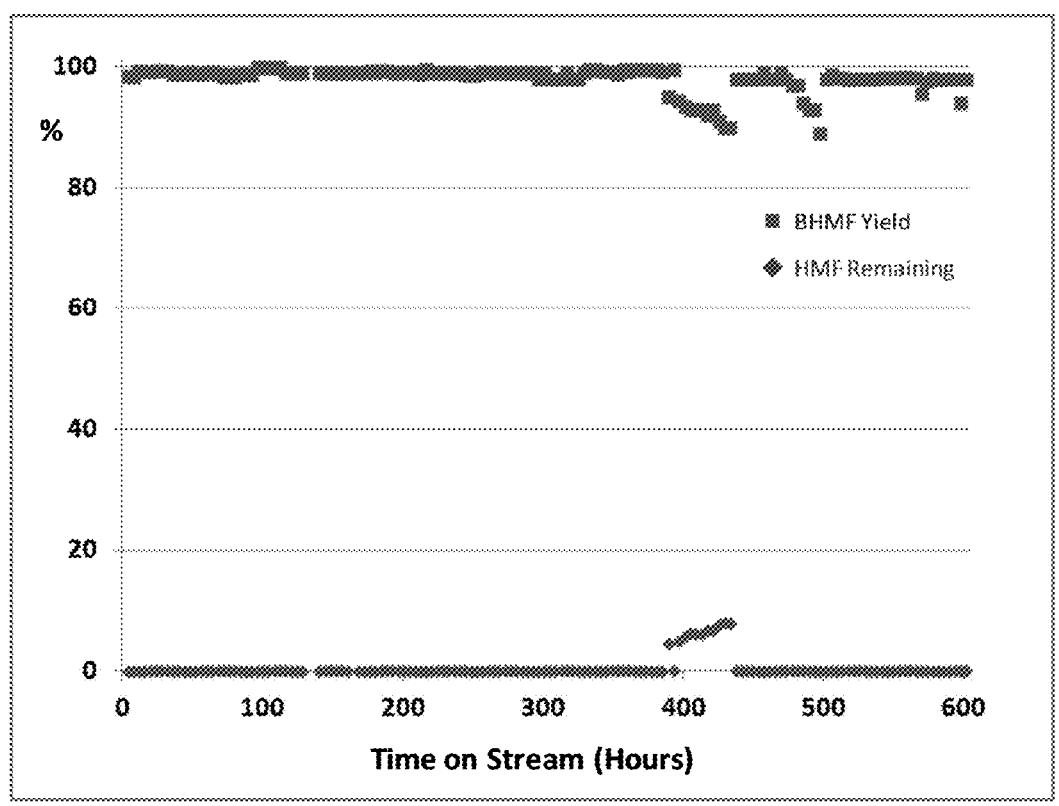
FIG. 6 depicts results (BHMF yield and HMF remaining as a function of time on-stream) for the conversion of HMF to BHMF in isopropanol in a fixed bed reactor with a guard bed (Ag on ZrO$_2$) using a Ag catalyst on a Al$_2$O$_3$ support, as described in Example 6.

2 g of silver catalyst (150-300 micron fraction) was placed into a fixed bed reactor tube with an internal diameter of 4.5 mm. A guard bed reactor tube with an internal diameter of 4.5 mm was filled with 3 g of guard bed material (150-300 micron fraction) and placed in the front of catalyst bed reactor. A solution of 0.4 M HMF in isopropanol (6.3 wt. %) was fed to the guard bed and the reactor at a flow rate of 100 μL/min. Both the guard bed and the reaction temperatures were 80° C. for 0 to 400 hours and 90° C. for 400 to 600 hours and both the guard bed and the reactor were under a partial pressure of hydrogen of 1000 psi. Results of the fixed bed run are presented in FIG. 6.

Example 7. Conversion of HMF (1) to BHMF (2) in a Fixed Bed Reactor with a Guard Bed Preparation of 10 wt. % Ag on $Al_2O_3$ catalyst. The silver nitrate solution was prepared by dissolving silver nitrate (Alfa) in deionized water. The $Al_2O_3$ support (BET surface area=160 $m^2/g$) was obtained from Sasol (Sasol 1/160). 4.37 mL of the silver nitrate solution (254 mg Ag/mL) was diluted with 2.13 mL of deionized water and added to 10 g of the $Al_2O_3$ support. The resultant material was dried at 120° C. for 2 hours and calcined in air at 400° C. for 3 hours. The calcined material was reduced under nitrogen flow at 300° C. for 3 hours.

Preparation of 7.0 wt. % Ag on $ZrO_2$ guard bed. The silver nitrate solution was prepared by dissolving silver nitrate (Alfa) in deionized water. The $ZrO_2$ support (BET surface area=40 $m^2/g$) was obtained from Saint Gobain. 1.48 mL of the silver acetate solution (254 mg Ag/mL) was added to 5 g of the $ZrO_2$ support. The resultant material was dried at 120° C. for 2 hours and calcined at 400° C. for 3 hours in air. After the calcination step the guard bed material was reduced under nitrogen gas flow at 300° C. for 4 hours.

Figure 7:
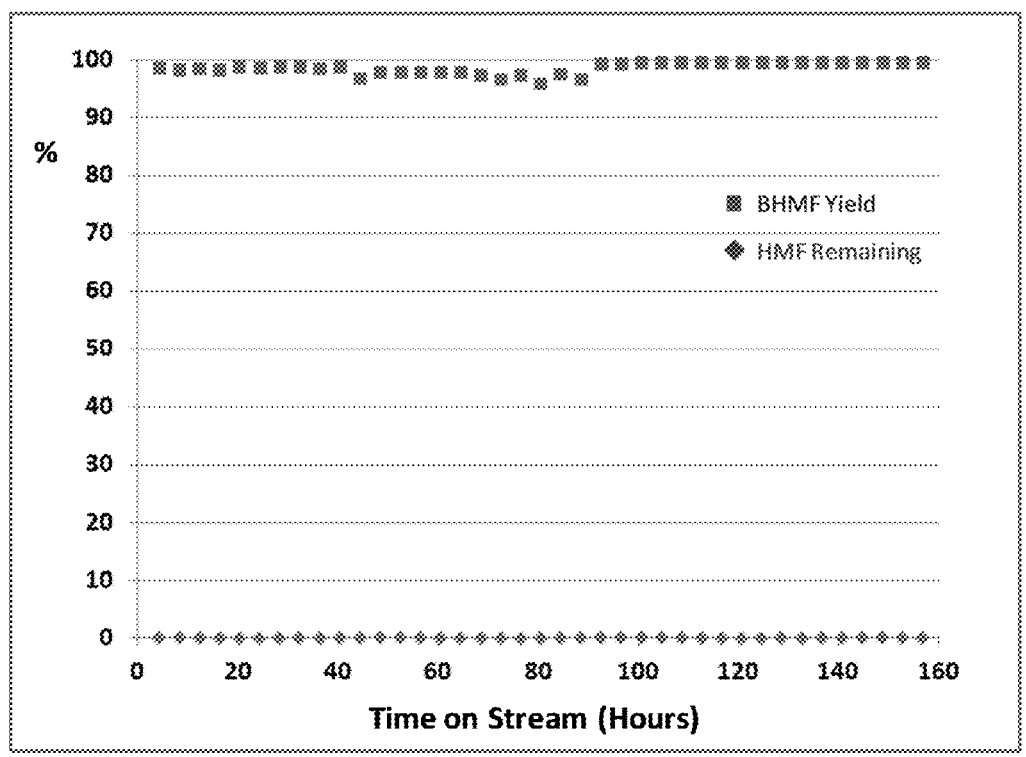
FIG. 7 depicts results (BHMF yield and HMF remaining as a function of time on-stream) for the conversion of HMF to BHMF in isopropanol in a fixed bed reactor with a guard bed (Ag on Al$_2$O$_3$) using a Ag catalyst on a ZrO$_2$ support, as described in Example 7.

4.8 g of silver catalyst (150-300 micron fraction) was placed into a fixed bed reactor tube with an internal diameter of 4.5 mm. A guard bed reactor tube with an internal diameter of 4.5 mm was filled with 3.5 g of guard bed material (150-300 micron fraction) and placed in the front of catalyst bed reactor. A solution of 0.8 M HMF in isopropanol (12.6 wt. %) was fed to the guard bed and the reactor at a flow rate of 100 μL/min. Both the guard bed and the reactor were at 80° C. and under a partial pressure of hydrogen of 1000 psi. Results of the fixed bed run are presented in FIG. 7.

Example 8. Consecutive Conversion of HMF (1) to BHMF (2) to BHMTHF (3) in a Fixed Bed Reactor with a Guard Bed Preparation of 3 wt. % Ni, 3 wt. % Cu on $ZrO_2$ catalyst. Nickel nitrate and copper nitrate solutions were prepared by dissolving $Ni(NO_3)_2 \cdot 6H_2O$ (Alfa) and $Cu(NO_3)_2 \cdot 3H_2O$ (Sigma-Aldrich) in deionized water. The $ZrO_2$ support (BET surface area=40 $m^2/g$) was obtained from Saint Gobain. 1.75 mL of nickel nitrate solution (181 mg Ni/mL) was mixed with 1.2 mL of copper nitrate solution (265 mg Cu/mL) to produce a solution with a weight ratio of 1:1. This solution was added to 10 g of the $ZrO_2$ support. The resultant material was dried at 120° C. for 2 hours, calcined in air at 350° C. for 3 hours and reduced under forming gas flow at 430° C. for 3 hours.

Preparation of 5.6 wt. % Ag on $ZrO_2$ guard bed. Silver acetate solution was prepared by dissolving silver acetate in 5M $NH_4OH$. The $ZrO_2$ support (BET surface area=40 $m^2/g$) was obtained from Saint Gobain. 3 mL of the solution (198 mg Ag/mL) was added to 10 g of the $ZrO_2$ support. The resultant material was dried at 120° C. for 2 hours, calcined in air at 250° C. for 3 hours and reduced under forming gas flow at 350° C. for 5 hours.

Figure 8:
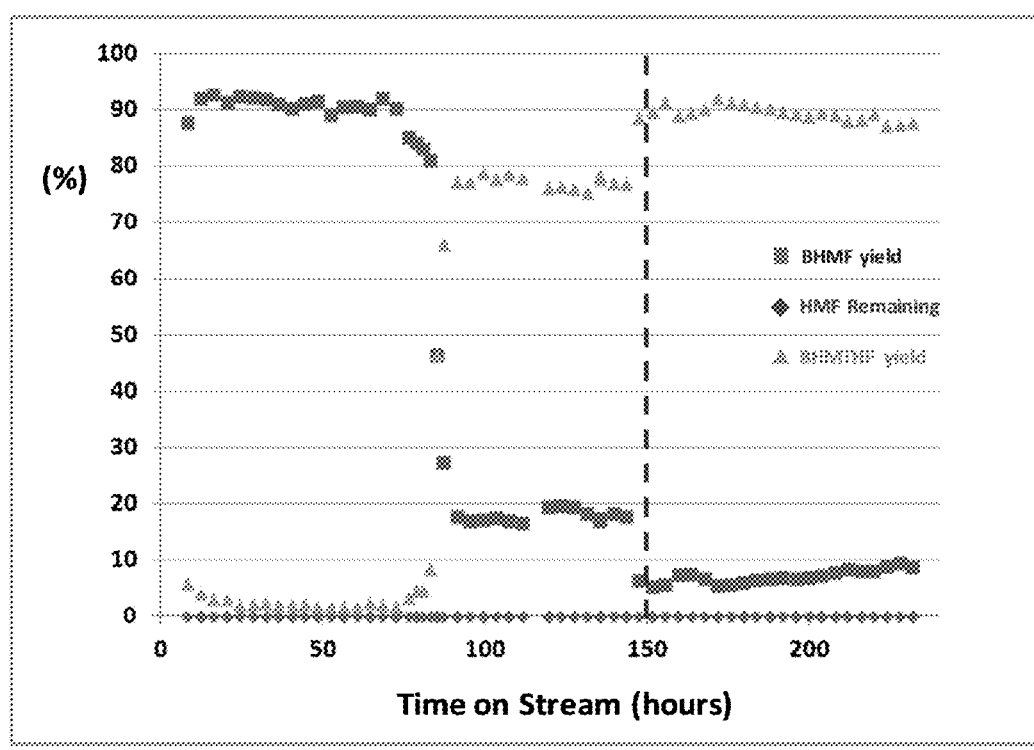
FIG. 8 depicts results (BHMF yield, BHMTHF yield and HMF remaining as a function of time on-stream) for the consecutive conversion of HMF to BHMF and BHMTHF in isopropanol in a fixed bed reactor with a guard bed (Ag on ZrO$_2$) using a Ni—Cu catalyst on a ZrO$_2$ support, as described in Example 8.

1.35 g of the Ni—Cu catalyst (150-300 micron fraction) was placed into a fixed bed reactor tube with an internal diameter of 4.5 mm. A guard bed reactor tube with an internal diameter of 4.5 mm was filled with 5 g of guard bed material (150-300 micron fraction) and placed in the front of catalyst bed reactor. A solution of 0.4 M HMF in isopropanol (6.3 wt. %) was fed to the guard bed at 80° C. and the reactor at 120° C. at a flow rate of 100 µL/min Both the guard bed and the reactor were under a partial pressure of hydrogen of 750 psi. Results of the fixed bed run are presented in FIG. 8 (illustrated from 150 hours onward in FIG. 8).

Example 9. Consecutive Conversion of HMF (1) to BHMF (2) to BHMTHF (3) in a Fixed Bed Reactor with a Guard Bed Preparation of 5.0 wt. % Ni on $ZrO_2$ catalyst. Nickel nitrate solution was prepared by dissolving $Ni(NO_3)_2.6H_2O$ (Alfa) in deionized water. The $ZrO_2$ support (BET surface area=40 $m^2/g$) was obtained from Saint Gobain. Nickel nitrate solution (2.9 mL, 181 mg Ni/mL) was added to 10 g of the $ZrO_2$ support. The resultant material was dried at 120° C. for 2 hours, calcined in air at 350° C. for 3 hours and reduced under forming gas flow at 430° C. for 3 hours.

Preparation of the 7.0 wt. % Ag on $ZrO_2$ guard bed. Silver nitrate solution was prepared by dissolving silver nitrate in deionized water. The $ZrO_2$ support (BET surface area=40 $m^2/g$) was obtained from Saint Gobain. 1.48 mL of the solution (254 mg Ag/mL) was added to 5 g of $ZrO_2$. The resultant material was dried at 120° C. for 2 hours, calcined at 400° C. for 3 hours in air and reduced under a $N_2$ flow at 300° C. for 4 hours.

Figure 9:
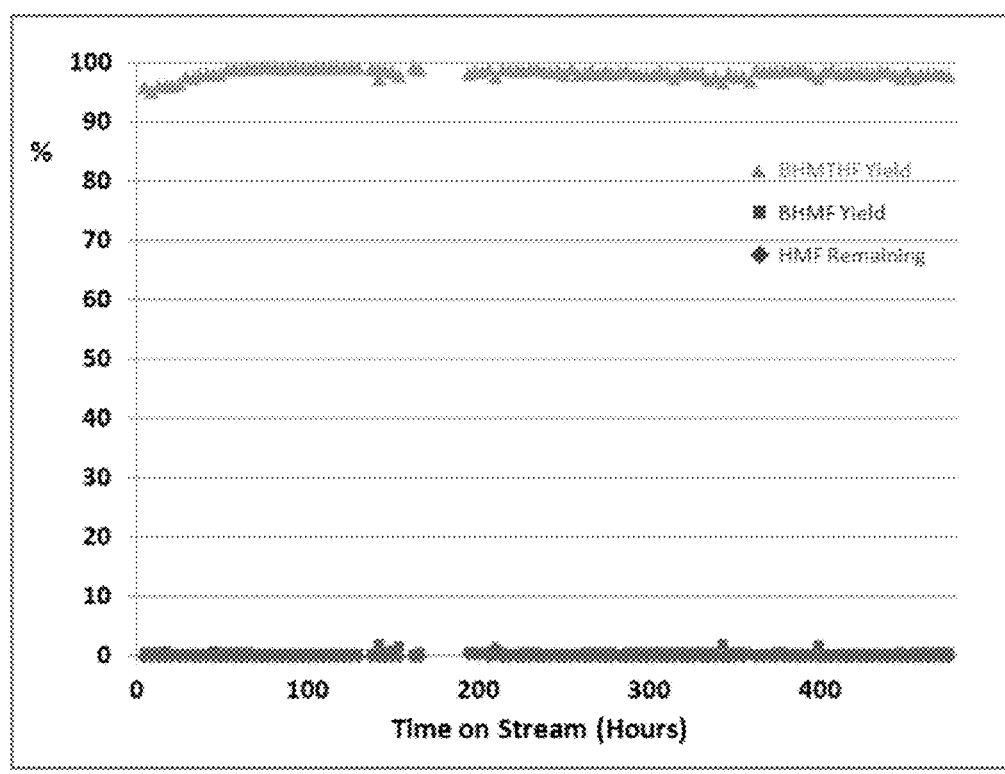
FIG. 9 depicts results (BHMF yield, BHMTHF yield and HMF remaining as a function of time on-stream) for the consecutive conversion of HMF to BHMF to BHMTHF in isopropanol in a fixed bed reactor with a guard bed (Ag on ZrO$_2$) using a Ni catalyst on a ZrO$_2$ support, as described in Example 9.

5 g of the Ni catalyst (150-300 micron fraction) was placed into a fixed bed reactor tube with an internal diameter of 4.5 mm. A guard bed reactor tube with an internal diameter of 4.5 mm was filled with 4.8 g of guard bed material (150-300 micron fraction) and this was placed in the front of catalyst bed reactor. A solution 0.4 M HMF in isopropanol (6.3 wt. %) was fed to the guard bed at 80° C. and the reactor at 90-110° C. at a flow rate of 100 µL/min. Both the guard bed and the reactor were under a partial pressure of hydrogen of 1000 psi. Results of the fixed bed run are presented in FIG. 9.

Example 10: Conversion of BHMTHF (3) to HTO (4) in a Fixed Bed Reactor

Using hydrogen and a Pt—W on $ZrO_2$ catalyst prepared, for example, according to the procedure described in International Publication No. WO 2013/109477, an aqueous BHMTHF solution (for example, ≥0.35M) can be converted into HTO in a fixed bed reactor over on-stream periods of 100 hours or more under conditions such as those described in International Publication No. WO 2013/109477.

Example 11: Consecutive Conversion of HMF (1) to BHMF (2) to HTO (4) in a Fixed Bed Reactor with a Guard Bed Preparation of 17.3 wt. % Cu on $Al_2O_3$ catalyst. Copper nitrate solution (3.95 mL, Sigma Aldrich) in DI water (265 mg Cu/mL) was added to 5 g of an $Al_2O_3$ support (XA 6175 BET surface area=260 $m^2/g$) obtained from Saint Gobain. The resultant material was dried at 120° C. for 2 hours, calcined in air at 350° C. for 3 hours and then reduced under forming gas flow at 220° C. for 6 hours.

Preparation of the 7.0 wt. % Ag on $ZrO_2$ guard bed. Silver nitrate solution was prepared by dissolving silver nitrate in deionized water. The $ZrO_2$ support (BET surface area=40 $m^2/g$) was obtained from Saint Gobain. 1.48 mL of the solution (254 mg Ag/mL) was added to 5 g of $ZrO_2$. The resultant material was dried at 120° C. for 2 hours, calcined at 400° C. for 3 hours in air and reduced under a $N_2$ flow at 300° C. for 4 hours.

2.5 g of the copper catalyst (150-425 micron fraction) was placed into a fixed bed reactor tube with internal diameter of 4.5 mm. A guard bed reactor tube with an internal diameter of 4.5 mm was filled with 4.8 g of guard bed material (150-425 micron fraction) and this was placed in the front of catalyst bed reactor. A solution of 0.4 M HMF in isopropanol (6.3 wt. %) was fed to the guard bed (temperature 80° C. for the first 100 hours, 30° C. from 100-170 hours), and the reactor (catalyst bed temperature 105-120° C.) at a flow rate of 100 µL/min. The temperature of the guard bed was reduced at about 100 hours on-stream in response to sample analysis. Both the guard bed and the reactor were under a partial pressure of hydrogen of 750-1100 psi. The hydrogen pressure was adjusted at specific time points in response to sample analysis. During the course of the 170 hour run, HMF was fully converted, BHMF was observed as intermediate and HTO was produced with a consistent yield. No BHMTHF was observed during the course of the 170 hour run indicating the direct conversion of BHMF to HTO.

Example 12: Consecutive Conversion of HMF (1) to BHMF (2) to BHMTHF (3) in a Fixed Bed Reactor with a Guard Bed Using an Extrudate Catalyst Preparation of 14 wt. % Ni on $Al_2O_3$ Extrudate. Nickel nitrate solution was prepared by dissolving $Ni(NO_3)_2.6H_2O$ (Alfa) in DI water. $Al_2O_3$ support (SA 31132, 1.5 mm extrudates, BET surface area=55 $m^2/g$) was obtained from Saint Gobain. Nickel nitrate solution (17.83 mL, 181 mg Ni/mL) was added to 20 g of the $Al_2O_3$ support. The resultant material was dried at 120° C. for 2 hours, calcined in air at 350° C. for 3 hours and then reduced under forming gas flow at 380° C. for 1 hour and subsequently 430° C. for 3 hours.

Preparation of 14 wt. % Ag on $Al_2O_3$ spheres guard bed. Silver nitrate solution was prepared by dissolving silver nitrate (Strem) in DI water. $Al_2O_3$ support (Sasol 1/160, 1.0 mm spheres, BET surface area=160 $m^2/g$) was obtained from Sasol. Silver nitrate solution (12.82 mL, 254 mg Ag/mL) was added to 20 g of the $Al_2O_3$ support. The resultant material was dried at 120° C. for 2 hours, calcined at 400° C. for 3 hours in air and then reduced under a $N_2$ flow at 300° C. for 4 hours.

Figure 10:
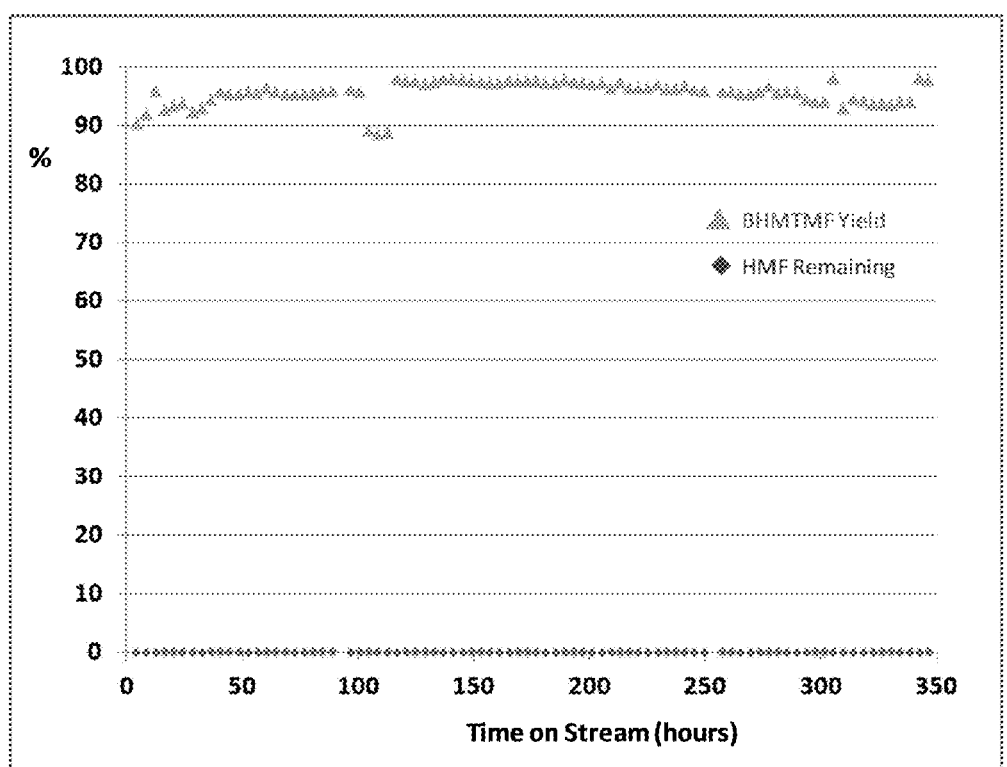
FIG. 10 depicts results (BHMTHF yield and HMF remaining as a function of time on-stream) for the consecutive conversion of HMF to BHMF to BHMTHF in isopropanol in a fixed bed reactor with a guard bed (Ag on Al$_2$O$_3$ spheres) using a Ni on Al$_2$O$_3$ catalyst extrudate, as described in Example 12.

11.3 g of the extrudate Ni catalyst was placed into a fixed bed reactor tube with an internal diameter of 10.2 mm. A guard bed reactor tube with an internal diameter of 10.2 mm was filled with 16 g of guard bed material and this was placed in the front of catalyst bed reactor. A solution of 0.4 M HMF in isopropanol (6.3 wt. %) was fed to the guard bed (temperature 80-90° C.) and the reactor/catalyst bed (temperature 110° C.) at a flow rate of 500 µL/min for 0-290 hours, followed by a solution of 0.8 M HMF in isopropanol (12.6 wt. %) for 290-350 hours. Both the guard bed and the reactor were under a partial pressure of hydrogen of 1000 psi. Results of the fixed bed run are presented in FIG. 10.

Example 13: Consecutive Conversion of HMF (1) to BHMF (2) in a Fixed Bed Reactor with a Guard Bed Using Catalyst Spheres Preparation of 14 wt. % Ag on $Al_2O_3$ catalyst spheres. Silver nitrate solution was prepared by dissolving silver nitrate (Strem) in DI water. $Al_2O_3$ support (Sasol 1/160, 1.0 mm spheres, BET surface area=160 $m^2$/g) was obtained from Sasol. Silver nitrate solution (26 mL, 253 mg Ag/mL) was added to 40 g of the $Al_2O_3$ support. The resultant material was dried at 120° C. for 2 hours, calcined in air at 400° C. for 3 hours and then reduced under $N_2$ flow at 300° C. for 3 hours.

Preparation of 14 wt. % Ag on $Al_2O_3$ guard bed spheres. Silver nitrate solution was prepared by dissolving silver nitrate (Strem) in DI water. $Al_2O_3$ support (Sasol 1/160, 1.0 mm spheres, BET surface area=160 $m^2$/g) was obtained from Sasol. Silver nitrate solution (26 mL, 253 mg Ag/mL) was added to 40 g of the $Al_2O_3$ support. The resultant material was dried at 120° C. for 2 hours, calcined in air at 400° C. for 3 hours and then reduced under $N_2$ flow at 300° C. for 3 hours.

Figure 11:
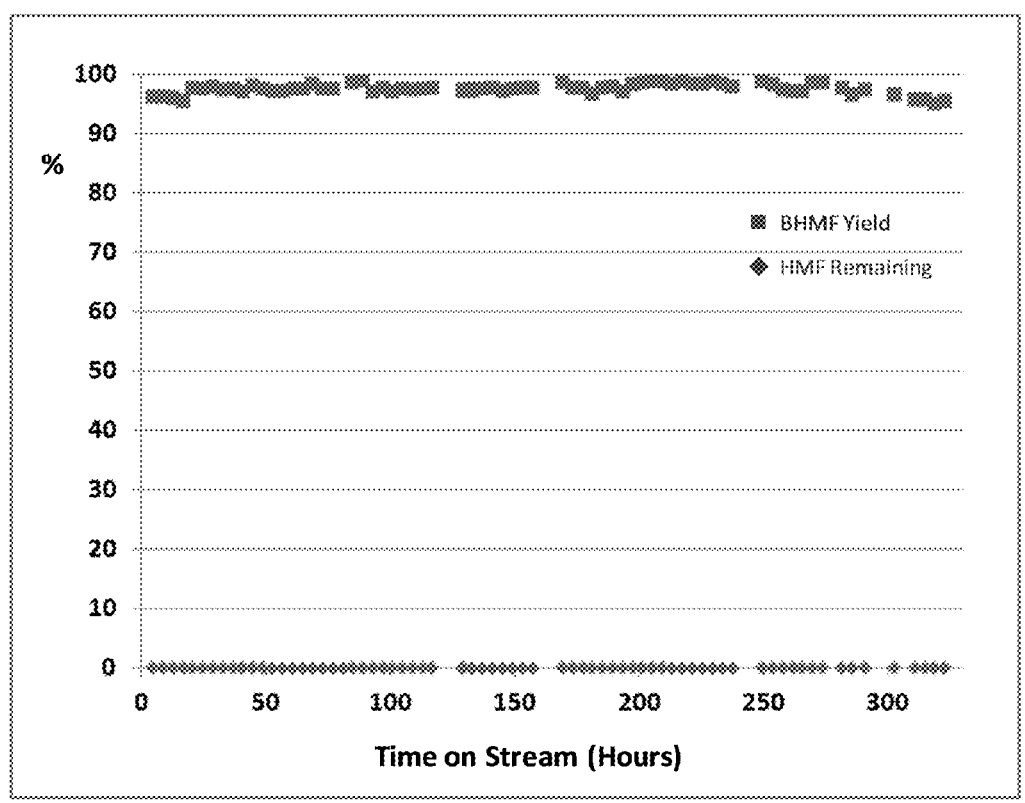
FIG. 11 depicts results (BHMF yield and HMF remaining as a function of time on-stream) for the conversion of HMF to BHMF in isopropanol in a fixed bed reactor with a guard bed (Ag on Al$_2$O$_3$ spheres) using a Ag catalyst on Al$_2$O$_3$ spheres, as described in Example 13.
Figure 12:
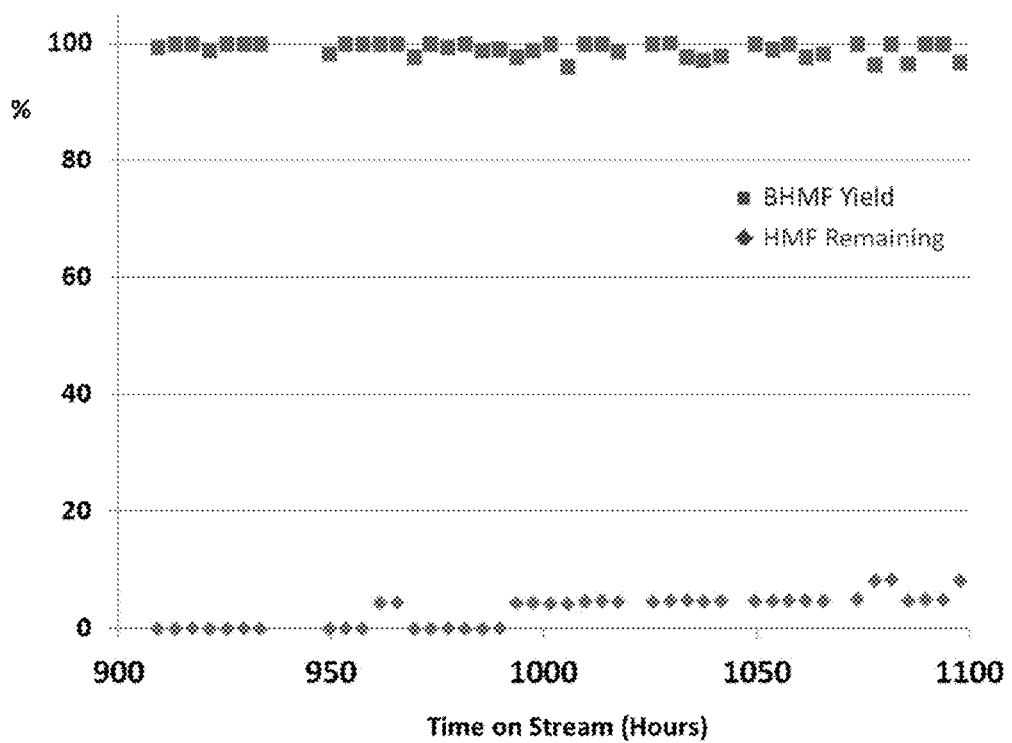
FIG. 12 depicts results (BHMF yield and HMF remaining as a function of time on stream) for the conversion of HMF to BHMF in an isopropanol/water mixture using a commercial Cu/Mn/Al$_2$O$_3$ catalyst, as described in Example 14. Data collected between 900-1100 hours on stream is displayed.
Figure 13:
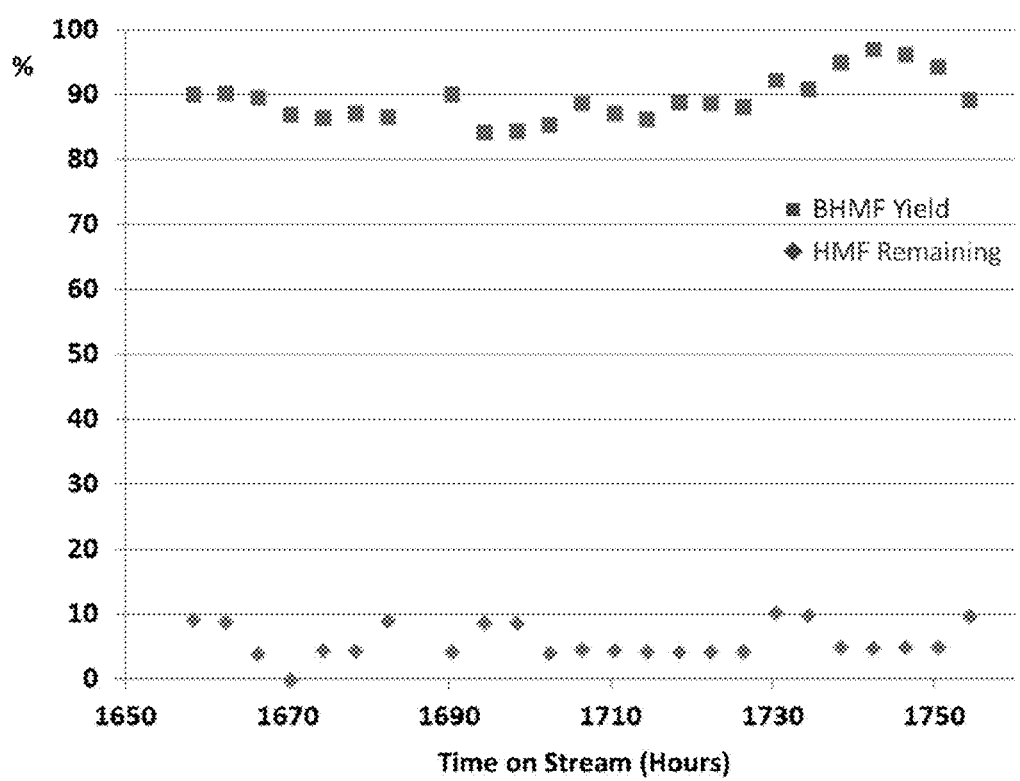
FIG. 13 depicts results (BHMF yield and HMF remaining as a function of time on stream) for the conversion of HMF to BHMF in a dioxane/water mixture using a commercial Cu/Mn/Al$_2$O$_3$ catalyst, as described in Example 14. Data collected between 1650-1750 hours on stream is displayed.

16 g of the Ag catalyst was placed into a fixed bed reactor tube with an internal diameter of 10.2 mm. A guard bed reactor tube with an internal diameter of 10.2 mm was filled with 16 g of guard bed material and this was placed in the front of catalyst bed reactor. A solution of 0.4 M HMF in isopropanol (6.3 wt. %) was fed to the guard bed (temperature 80° C.) and the reactor/catalyst bed (temperature 80° C.) at a flow rate of 500 μL/min for 0-265 hours, followed by a solution of 0.8 M HMF in isopropanol (12.6 wt. %) for 265-350 hours. Both the guard bed and the reactor were under a partial pressure of hydrogen of 1000 psi. Results of the fixed bed run are presented in FIG. 11.

Example 14: Conversion of HMF (1) to BHMF (2) in a Fixed Bed Reactor Using Various Solvent Compositions 17.6 g of a commercial Cu/Mn/$Al_2O_3$ catalyst (T-4874 supplied by Clariant; supplied as a 1/16" extrudate) was reduced in a tube furnace under a flow of 5% $H_2$ in $N_2$ for 6 hours and then brought to room temperature followed by exposure to a flow of 0.5% $O_2$ in $N_2$ for 1 hour. The resultant catalyst was placed into a fixed bed reactor tube with an internal diameter of 10.2 mm. A solution of 0.4 M HMF in a solvent mixture of 87:13 isopropanol:$H_2O$ (as a weight ratio) was fed to the reactor at a flow rate of 500 μL/min for a period of 1100 hours. The reactor was under a partial pressure of hydrogen of 1000 psi. The reactor temperature was set to 70° C., 75° C. and 80° C. at various stages during the 1100 hours. For the duration of the 1100 hours on stream, the HMF conversion was >90% and the selectivity to BHMF was >90%.

After 1100 hours on stream, the reactor feed was switched to a solution of 0.4 M HMF in a 82:18 Dioxane:$H_2O$ (as a weight ratio), which was fed to the reactor (reactor temperature 70° C., partial pressure of hydrogen 1000 psi) at a flow rate of 500 μL/min for a further period of 100 hours, during which the HMF conversion was >90% and the selectivity to BHMF was >85%.

What is claimed is:

1. A process for preparing 2,5-bis-hydroxymethylfuran (BHMF) from 5-hydroxymethylfurfural (HMF) comprising: reacting the 5-hydroxymethylfurfural (HMF) with hydrogen in a continuous flow reactor in the presence of an organic solvent and a heterogeneous reduction catalyst comprising Cu to form the 2,5-bis-hydroxymethylfuran (BHMF) over an on-stream period of at least 150 hours.

2. A process for preparing 2,5-bis-hydroxymethylfuran (BHMF) from 5-hydroxymethylfurfural (HMF) comprising: reacting the 5-hydroxymethylfurfural (HMF) with hydrogen in a continuous flow reactor in the presence of an organic solvent and a heterogeneous reduction catalyst comprising Pt to form the 2,5-bis-hydroxymethylfuran (BHMF) over an on-stream period of at least 150 hours.

3. The process of claim 1, wherein the heterogeneous reduction catalyst further comprises a modifier.

4. The process of claim 3, wherein the modifier is selected from the group consisting of Mn, Co, Au, W, Cu, Zn, Mo, Sb, Bi and Pb.

5. The process of claim 1, wherein the heterogeneous reduction catalyst comprises a combination of metals selected from the group consisting of Co—Cu and Ni—Cu.

6. The process of claim 1, wherein the heterogeneous reduction catalyst further comprises a catalyst support.

7. The process of claim 6, wherein the catalyst support is selected from the group consisting of carbons, aluminas, zirconias, silicas, alumina-silicas, titanias, alumina-titanias, silicon carbides and mixed phases thereof.

8. The process of claim 1, wherein the heterogeneous reduction catalyst further comprises an alumina catalyst support.

9. The process of claim 1 further comprising: feeding the 5-hydroxymethylfurfural (HMF) through a guard bed comprising a transition metal to the continuous flow reactor.

10. The process of claim 9, wherein the guard bed comprises at least one transition metal selected from the group consisting of Ag, Zn, Cu, Fe, Ni, Co and Pb or a salt or combination thereof.

11. The process of claim 9, wherein the guard bed comprises at least one transition metal selected from the group consisting of Ag, Zn, Cu and Pb or a salt or combination thereof.

12. The process of claim 1, wherein the process comprises feeding the 5-hydroxymethylfurfural (HMF) to the continuous flow reactor at a concentration of greater than about 6 weight percent in the organic solvent.

13. The process of claim 1, wherein the 2,5-bis-hydroxymethylfuran (BHMF) is formed with at least about 90% selectivity and at least 85% conversion of the 5-hydroxymethylfurfural (HMF).

14. The process of claim 1, wherein the process comprises forming the 2,5-bis-hydroxymethylfuran (BHMF) with at least about 90% selectivity and at least 90% 5-hydroxymethylfurfural (HMF) conversion.

15. The process of claim 1, wherein the process comprises forming the 2,5-bis-hydroxymethylfuran (BHMF) with at least about 95% selectivity and at least 90% 5-hydroxymethylfurfural (HMF) conversion.

16. The process of claim 1, wherein the organic solvent comprises less than about 25 weight % water.

17. The process of claim 1, wherein the organic solvent comprises from about 5 weight % to about 20 weight % water.

18. The process of claim 1, wherein the 5-hydroxymethylfurfural (HMF) is reacted with hydrogen at a temperature in a range of about 50° C. to about 150° C. and at a pressure in a range of about 50 psi to about 2000 psi.

19. The process of claim 1, wherein:
the 5-hydroxymethylfurfural (HMF) is reacted with hydrogen in the continuous flow reactor at a pressure in a range of about 50 psi to about 2000 psi;
the organic solvent comprises less than about 25 weight % water; and
the 2,5-bis-hydroxymethylfuran (BHMF) is formed with at least about 90% selectivity and at least 85% 5-hydroxymethylfurfural (HMF) conversion.

20. The process of claim 1, further comprising reacting the 2,5-bis-hydroxymethylfuran (BHMF) with hydrogen in a continuous flow reactor in the presence of a heterogeneous reduction catalyst comprising at least one metal selected from the group consisting of Ni, Co, Cu, Ag, Pd, Pt and Ru or a combination thereof to form 2,5-bis-hydroxymethyltetrahydrofuran (BHMTHF).

21. The process of claim 20, further comprising reacting the 2,5-bis-hydroxymethyltetrahydrofuran (BHMTHF) with hydrogen in a continuous flow reactor in the presence of a heterogeneous reduction catalyst comprising at least one metal selected from the group consisting of Ni, Co, Cu, Ag, Pt and Ru or a combination thereof to form 1,2,6-hexanetriol (HTO).

22. The process of claim 21, further comprising reacting the 1,2,6-hexanetriol (HTO) with hydrogen in a continuous flow reactor in the presence of a heterogeneous reduction catalyst comprising at least one metal selected from the group consisting of Ni, Co, Cu, Ag, Pt and Ru or a combination thereof to form 1,6-hexanediol (HDO).

23. The process of claim 1, further comprising reacting the 2,5-bis-hydroxymethylfuran (BHMF) with hydrogen in a continuous flow reactor in the presence of a heterogeneous reduction catalyst comprising at least one metal selected from the group consisting of Ni, Co, Cu, Ag, Pt, Pd and Ru or a combination thereof to form 1,2,6-hexanetriol (HTO).

24. The process of claim 23, further comprising reacting the 1,2,6-hexanetriol (HTO) with hydrogen in a continuous flow reactor in the presence of a heterogeneous reduction catalyst comprising at least one metal selected from the group consisting of Ni, Co, Cu, Ag, Pt and Ru or a combination thereof to form 1,6-hexanediol (HDO).

25. The process of claim 2, wherein the heterogeneous reduction catalyst further comprises a modifier.

26. The process of claim 25, wherein the modifier is selected from the group consisting of Mn, Co, Au, W, Cu, Zn, Mo, Sb, Bi and Pb.

27. The process of claim 2, wherein the heterogeneous reduction catalyst comprises a combination of metals which is Pt—Au.

28. The process of claim 2, wherein the heterogeneous reduction catalyst further comprises a catalyst support.

29. The process of claim 28, wherein the catalyst support is selected from the group consisting of carbons, aluminas, zirconias, silicas, alumina-silicas, titanias, alumina-titanias, silicon carbides and mixed phases thereof.

30. The process of claim 2, wherein the heterogeneous reduction catalyst further comprises an alumina catalyst support.

31. The process of claim 2 further comprising:
feeding the 5-hydroxymethylfurfural (HMF) through a guard bed comprising a transition metal to the continuous flow reactor.

32. The process of claim 31, wherein the guard bed comprises at least one transition metal selected from the group consisting of Ag, Zn, Cu, Fe, Ni, Co and Pb or a salt or combination thereof.

33. The process of claim 31, wherein the guard bed comprises at least one transition metal selected from the group consisting of Ag, Zn, Cu and Pb or a salt or combination thereof.

34. The process of claim 2, wherein the process comprises feeding the 5-hydroxymethylfurfural (HMF) to the continuous flow reactor at a concentration of greater than about 6 weight percent in the organic solvent.

35. The process of claim 2, wherein the 2,5-bis-hydroxymethylfuran (BHMF) is formed with at least about 90% selectivity and at least 85% conversion of the 5-hydroxymethylfurfural (HMF).

36. The process of claim 2, wherein the process comprises forming the 2,5-bis-hydroxymethylfuran (BHMF) with at least about 90% selectivity and at least 90% 5-hydroxymethylfurfural (HMF) conversion.

37. The process of claim 2, wherein the process comprises forming the 2,5-bis-hydroxymethylfuran (BHMF) with at least about 95% selectivity and at least 90% 5-hydroxymethylfurfural (HMF) conversion.

38. The process of claim 2, wherein the organic solvent comprises less than about 25 weight % water.

39. The process of claim 2, wherein the organic solvent comprises from about 5 weight % to about 20 weight % water.

40. The process of claim 2, wherein the 5-hydroxymethylfurfural (HMF) is reacted with hydrogen at a temperature in a range of about 50° C. to about 150° C. and at a pressure in a range of about 50 psi to about 2000 psi.

41. The process of claim 2, wherein:
the 5-hydroxymethylfurfural (HMF) is reacted with hydrogen in the continuous flow reactor at a pressure in a range of about 50 psi to about 2000 psi;
the organic solvent comprises less than about 25 weight % water; and
the 2,5-bis-hydroxymethylfuran (BHMF) is formed with at least about 90% selectivity and at least 85% 5-hydroxymethylfurfural (HMF) conversion.

42. The process of claim 2, further comprising reacting the 2,5-bis-hydroxymethylfuran (BHMF) with hydrogen in a continuous flow reactor in the presence of a heterogeneous reduction catalyst comprising at least one metal selected from the group consisting of Ni, Co, Cu, Ag, Pd, Pt and Ru or a combination thereof to form 2,5-bis-hydroxymethyltetrahydrofuran (BHMTHF).

43. The process of claim 42, further comprising reacting the 2,5-bis-hydroxymethyltetrahydrofuran (BHMTHF) with hydrogen in a continuous flow reactor in the presence of a heterogeneous reduction catalyst comprising at least one metal selected from the group consisting of Ni, Co, Cu, Ag, Pt and Ru or a combination thereof to form 1,2,6-hexanetriol (HTO).

44. The process of claim 43, further comprising reacting the 1,2,6-hexanetriol (HTO) with hydrogen in a continuous flow reactor in the presence of a heterogeneous reduction catalyst comprising at least one metal selected from the group consisting of Ni, Co, Cu, Ag, Pt and Ru or a combination thereof to form 1,6-hexanediol (HDO).

45. The process of claim 2, further comprising reacting the 2,5-bis-hydroxymethylfuran (BHMF) with hydrogen in a continuous flow reactor in the presence of a heterogeneous reduction catalyst comprising at least one metal selected from the group consisting of Ni, Co, Cu, Ag, Pt, Pd and Ru or a combination thereof to form 1,2,6-hexanetriol (HTO).

46. The process of claim 45, further comprising reacting the 1,2,6-hexanetriol (HTO) with hydrogen in a continuous flow reactor in the presence of a heterogeneous reduction catalyst comprising at least one metal selected from the group consisting of Ni, Co, Cu, Ag, Pt and Ru or a combination thereof to form 1,6-hexanediol (HDO).

\* \* \* \* \*